US011479558B2

(12) United States Patent
Scheidt et al.

(10) Patent No.: US 11,479,558 B2
(45) Date of Patent: Oct. 25, 2022

(54) SUBSTITUTED TETRAHYDROPYRANOINDOLES, DERIVATIVES THEREOF, AND THEIR METHODS OF SYNTHESIS AND USE

(71) Applicant: NORTHWESTERN UNIVERSITY, Evanston, IL (US)

(72) Inventors: Karl A. Scheidt, Evanston, IL (US); Mark A. Maskeri, Evanston, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 0 days.

(21) Appl. No.: 16/924,943

(22) Filed: Jul. 9, 2020

(65) Prior Publication Data

US 2021/0009603 A1 Jan. 14, 2021

Related U.S. Application Data

(60) Provisional application No. 62/872,214, filed on Jul. 9, 2019.

(51) Int. Cl.
*C07D 491/14* (2006.01)
*C07D 491/052* (2006.01)
*C07D 491/107* (2006.01)

(52) U.S. Cl.
CPC ..... *C07D 491/052* (2013.01); *C07D 491/107* (2013.01)

(58) Field of Classification Search
CPC ............................ C07D 491/14; A61K 31/407
USPC .......................................... 548/442; 514/411
See application file for complete search history.

(56) References Cited

U.S. PATENT DOCUMENTS

| 3,852,285 | A | * | 12/1974 | Demerson | ............ | C07D 209/08 544/80 |
|---|---|---|---|---|---|---|
| 7,851,640 | B2 | | 12/2010 | Scheidt | | |
| 8,912,341 | B2 | | 12/2014 | Scheidt | | |
| 9,260,564 | B2 | | 2/2016 | Lombardo | | |
| 9,309,217 | B2 | | 4/2016 | Scheidt | | |
| 9,334,297 | B2 | | 5/2016 | Scheidt | | |
| 9,512,146 | B2 | | 12/2016 | Scheidt | | |
| 9,527,812 | B2 | | 12/2016 | Scheidt | | |
| 9,624,190 | B2 | | 4/2017 | Scheidt | | |
| 9,643,947 | B2 | | 5/2017 | Scheidt | | |
| 9,840,487 | B2 | | 12/2017 | Scheidt | | |
| 9,981,968 | B2 | | 5/2018 | Schiltz | | |
| 10,308,624 | B2 | | 6/2019 | Scheidt | | |
| 10,323,039 | B2 | | 6/2019 | Scheidt | | |
| 10,654,865 | B2 | | 5/2020 | Scheidt | | |
| 10,781,172 | B2 | | 9/2020 | Scheidt | | |
| 2014/0206886 | A1 | | 7/2014 | Scheidt | | |
| 2015/0065703 | A1 | | 3/2015 | Scheidt | | |
| 2016/0002252 | A1 | | 1/2016 | Schiltz | | |
| 2019/0276458 | A1 | | 9/2019 | Schiltz | | |
| 2020/0181106 | A1 | | 6/2020 | Scheidt | | |
| 2020/0399241 | A1 | | 12/2020 | Scheidt | | |
| 2021/0009547 | A1 | | 1/2021 | Scheidt | | |
| 2021/0070725 | A1 | | 3/2021 | Scheidt | | |

OTHER PUBLICATIONS

Berettoni, et. al., International Electronic Conference on Synthetic Organic Chemistry, 17th, Nov. 1-30, 2013 (2013). (Abstract) (Year: 2013).*
Ascic, et. al., Chemistry—A European Journal (2014), 20(12), 3297-3300. (Year: 2014).*
Ascic E et al., Synthesis of oxacyclic scaffolds via dual ruthenium hydride/Brønsted acid-catalyzed isomerization/cyclization of allylic ethers. Chemistry 2014, 20, 3297.
Beesley, R. M., et al. "CXIX.—The formation and stability of spiro-compounds. Part I. spiro-Compounds from cyclo hexane." Journal of the Chemical Society, Transactions 107 (1915): 1080-1106.
Bhadra, S., et al. "Substrate directed asymmetric reactions." Chemical reviews 118.7 (2018): 3391-3446.
Chung, C.-P., et al. "Antiproliferative lactams and spiroenone from adlay bran in human breast cancer cell lines." Journal of agricultural and food chemistry 59.4 (2011): 1185-1194.
Davies, HML, et al. "C—H functionalization in organic synthesis." Chemical Society Reviews 40.4 (2011): 1855-1856.
Galliford, C. V., et al. "Pyrrolidinyl-spirooxindole natural products as inspirations for the development of potential therapeutic agents." Angewandte Chemie International Edition 46.46 (2007): 8748-8758.
Gao, Z.-H., et al. "Four new indole alkaloids from Plantago asiatica." Natural products and bioprospecting 2.6 (2012): 249-254.
Larghi, E. L., et al. "Synthesis of Oxacycles Employing the Oxa-Pictet-Spengler Reaction: Recent Developments and New Prospects." European Journal of Organic Chemistry 2011.27 (2011): 5195-5231.
Lee, M-Y et al, Isolation and characterization of new lactam compounds that inhibit lung and colon cancer cells from adlay (*Coix lachryma-jobi* L. var. *ma-yuen Stapf*) bran. Food and Chemical Toxicology 46, 1933-1939 (2008).
Lombardo, VM et al, A Tandem Isomerization/Prins Strategy: Iridium(III)/Brønsted Acid Cooperative Catalysis. Angew. Chem. Int. Ed. 52, 12910-12914 (2013).
Murauski, KJR, et al. "A Cooperative Ternary Catalysis System for Asymmetric Lactonizations of a-Ketoesters." Advanced synthesis & catalysis 359.21 (2017): 3713-3719.
Nasir, NM et al. "Strategies for the construction of tetrahydropyran rings in the synthesis of natural products." Organic & Biomolecular Chemistry 12.21 (2014): 3323-3335.

(Continued)

*Primary Examiner* — Jeffrey H Murray
(74) *Attorney, Agent, or Firm* — Quarles & Brady LLP

(57) ABSTRACT

Disclosed herein are tetrahydropyranoindole compounds and derivatives thereof, as well as their methods of synthesis and use. The disclosed compounds may be synthesized by methods that utilize a cooperative hydrogen bond donor/Brønsted acid system. The disclosed compounds may be useful for treating a disease, disorder, or a symptom thereof in a subject in need thereof, such as pain, swelling, and joint stiffness. The disclosed compounds also may be useful for treating cell proliferative diseases and disorders such as cancer.

27 Claims, 7 Drawing Sheets

(56) References Cited

OTHER PUBLICATIONS

Parmar, D., et al. "Complete field guide to asymmetric BINOL-phosphate derived Brønsted acid and metal catalysis: history and classification by mode of activation; Brønsted acidity, hydrogen bonding, ion pairing, and metal phosphates." Chemical reviews 114.18 (2014): 9047-9153.
Schreiner, P. R., et al. "H-bonding additives act like Lewis acid catalysts." Organic letters 4.2 (2002): 217-220.
Shavel, J. et al. "Oxindole Alkaloids. I. Oxidative-Rearrangement of Indole Alkaloids to their Oxindole Analogs." Journal of the American Chemical Society 84.7 (1962): 1320-1321.
Wang, M. H., et al. "Enantioselective β-protonation by a cooperative catalysis strategy." Journal of the American Chemical Society 137.18 (2015): 5891-5894.
Xu, H., et al. "Asymmetric cooperative catalysis of strong Brønsted acid-promoted reactions using chiral ureas." Science 327.5968 (2010): 986-990.
Zhang, Z. et al. "(Thio) urea organocatalysis—What can be learnt from anion recognition?." Chemical Society Reviews 38.4 (2009): 1187-1198.
Zhao, C. et al. "Direct formation of oxocarbenium Ions under weakly acidic conditions: catalytic enantioselective Oxa-Pictet-Spengler reactions." Journal of the American Chemical Society 138.29 (2016): 9053-9056.
Zhao, Y et al, Oxidative transformation of cyclic ethers/amines to lactones/lactams using a DIB/TBHP protocol. RSC Advances 3, 19765 (2013).
Zheng, C. et al. "Unified mechanistic understandings of Pictet-Spengler reactions." Chem 4.8 (2018): 1952-1966.

\* cited by examiner

| # | R | time | co-catalyst[b] | yield[c] | e.r. |
|---|---|---|---|---|---|
| 1[d] | H | 48 h | none | 27% | 51:49 |
| 2[d] | 2-HO-benzyl | 18 h | none | 52% | 53:47 |
| 3[d] | CONH-Ph | 18 h | none | 24% | 72:28 |
| 4 | CONH-Ar | 18 h | none | 67% | 68:32 |
| 5 | CONH-Ar | 18 h | Ar-NH-C(=S)-NH-Ar | 60% | 89:11 |
| 6 | CONH-Ar | 15 min | Ar-NH-C(=O)-NH-Ar | 89%[e] | 97:3 |
| 7 | H | 48 h | Ar-NH-C(=O)-NH-Ar | 19% | 52:48 |
| 8 | CONMe-Ar | 24 h | Ar-NH-C(=O)-NH-Ar | decomp. | - |

| HBD | Yield (%, NMR) | e.r. |
|---|---|---|
| A | 60 | 89:11 |
| B | 78 | 66:34 |
| C | 70 | 58:42 |
| D | 94 | 64:36 |
| E | 90 | 97:3 |
| F | 81 | 83:17 |

SUBSTITUTED TETRAHYDROPYRANOINDOLES, DERIVATIVES THEREOF, AND THEIR METHODS OF SYNTHESIS AND USE

CROSS-REFERENCE TO RELATED APPLICATIONS

This application claims the benefit of priority to U.S. Provisional Application Ser. No. 62/872,214 filed on Jul. 9, 2019, the entire contents of which are incorporated by reference herein

STATEMENT REGARDING FEDERALLY SPONSORED RESEARCH OR DEVELOPMENT

This invention was made with government support under GM073072 awarded by the National Institutes of Health. The government has certain rights in the invention.

BACKGROUND

The field of the present disclosure relates to substituted tetrahydropyranoindole compounds, and derivatives thereof, as well as their methods of use and synthesis. The disclosed tetrahydropyranoindole compounds may exhibit bioactivities, such as anti-inflammatory, analgesic, and/or antipyretic bioactivities.

Tetrahydropyranoindole compounds have been shown to be potent anti-inflammatory drugs with analgesic and antipyretic activities in animal models and in humans (Demerson, C. A. et. al. J. Med. Chem. 1976, 19, 391); (Martel, R. R. et. al. Can. J. Physiol. Pharmacol. 1976, 54, 245). Etodolac (Ultradol) (1, 1,8-diethyl-1,3,4,9-tetrahydropyrano [3,4-b]indole-1-acetic acid) is a known tetrahydropyranoindole compound and a nonsteroidal anti-inflammatory drug (NSAID) that is used to relieve pain, swelling, and joint stiffness that is associated with various conditions, such as arthritis. Pemedolac [cis-1-ethyl-1,3,4,9-tetrahydro-4-(phenylmethyl)-pyrano [3,4-b]indole-1-acetic acid; AY-30,715] is another known tetrahydropyranoindole compound that has exhibited potent analgesic effects against chemically induced pain in rats and mice and against inflammatory pain in rats. Currently, there is an interest in developing new molecules that have the potential for relieving pain, swelling, and joint stiffness.

Spirolactam derivatives of tetrahydropyranoindole compounds also have been shown to exhibit biological activities. For instance, coixspirolactam C, a natural product isolated from adlay bran has been demonstrated to exhibit mild inhibitor activity against lung and colon cancer cell lines (IC50=30=50 µg/mL). (See Lee, H. Y. et al., Food Chem. Toxicol. 2008, 46, 1933-1939; and Chung et al., J. Agric. Food Chem. 2011, 59, 1185-1194)

Here, the inventors disclose new tetrahydropyranoindole compounds and derivatives thereof. The disclosed tetrahydropyranoindole compounds may be prepared using a cooperative hydrogen bond donor/Brønsted acid system.

SUMMARY

Disclosed herein are tetrahydropyranoindole compounds and derivatives thereof, as well as their methods of use and synthesis. In some embodiments, the disclosed tetrahydropyranoindole compounds may have a formula as follows, or a salt, a hydrate, or a spirolactam derivative thereof:

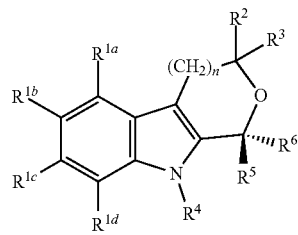

wherein: $R^{1a}$, $R^{1b}$, $R^{1c}$, and $R^{1d}$ are independently selected from hydrogen, alkyl, halo, haloalkyl, and alkoxy, wherein optionally at least one of $R^{1a}$, $R^{1b}$, $R^{1c}$, and $R^{1d}$ is not hydrogen; $R^2$ and $R^3$ are independently selected from hydrogen or alkyl, optionally wherein at least one of $R^2$ and $R^3$ is not hydrogen; $R^4$ is selected from hydrogen, alkyl, carboxy, carboxyalkyl, carboxamido, and carboxamidoaryl, which aryl substituent optionally is substituted at one or more positions with haloalkyl; $R^5$ and $R^6$ are independently selected from hydrogen and alkyl, wherein optionally at least one of $R^5$ and $R^6$ is not hydrogen; and n is an integer selected from 1 and 2.

Also disclosed are pharmaceutical compositions that comprise the disclosed tetrahydropyranoindole compounds with a carrier, diluent, or excipient. The compounds may comprise an effective amount of compounds (or salts thereof) for treating or preventing a disease, disorder, disorders, conditions, symptoms, such as, but not limited to relieving pain, swelling, and joint stiffness that is associated with various conditions, such as arthritis, and/or treating cell proliferative diseases and disorders such as cancer.

Also disclosed are methods of treating or preventing one of the aforementioned diseases or disorders that include administering the disclosed tetrahydropyranoindole compounds in an effective amount to a subject in need thereof in order to treat or prevent the disease or disorder. For example, the compound may be formulated in a pharmaceutical composition and administered to a subject having or at risk for developing pain, swelling, and joint stiffness and/or a subject having or at risk for developing cancer.

The disclosed tetrahydropyranoindole compounds may be used in pharmaceutical compositions and methods for treating diseases, disorders, or symptoms in a subject, such as but not limited to relieving pain, swelling, and joint stiffness that is associated with various conditions, such as arthritis. The disclosed compounds may be used in pharmaceutical compositions and methods for treating cell proliferative diseases and disorders which may include cancer.

DESCRIPTION OF THE DRAWINGS

The present invention is described herein using several definitions, as set forth below and throughout the application.

FIG. 2 is a schematic illustration of an exemplary reaction pathway and example tetrahydropyranoindole compounds in accordance with some embodiments of the present disclosure.

FIG. 7 is a schematic illustration of an exemplary reaction pathway and reaction data in accordance with some embodiments of the present disclosure.

DETAILED DESCRIPTION

Figure 1:
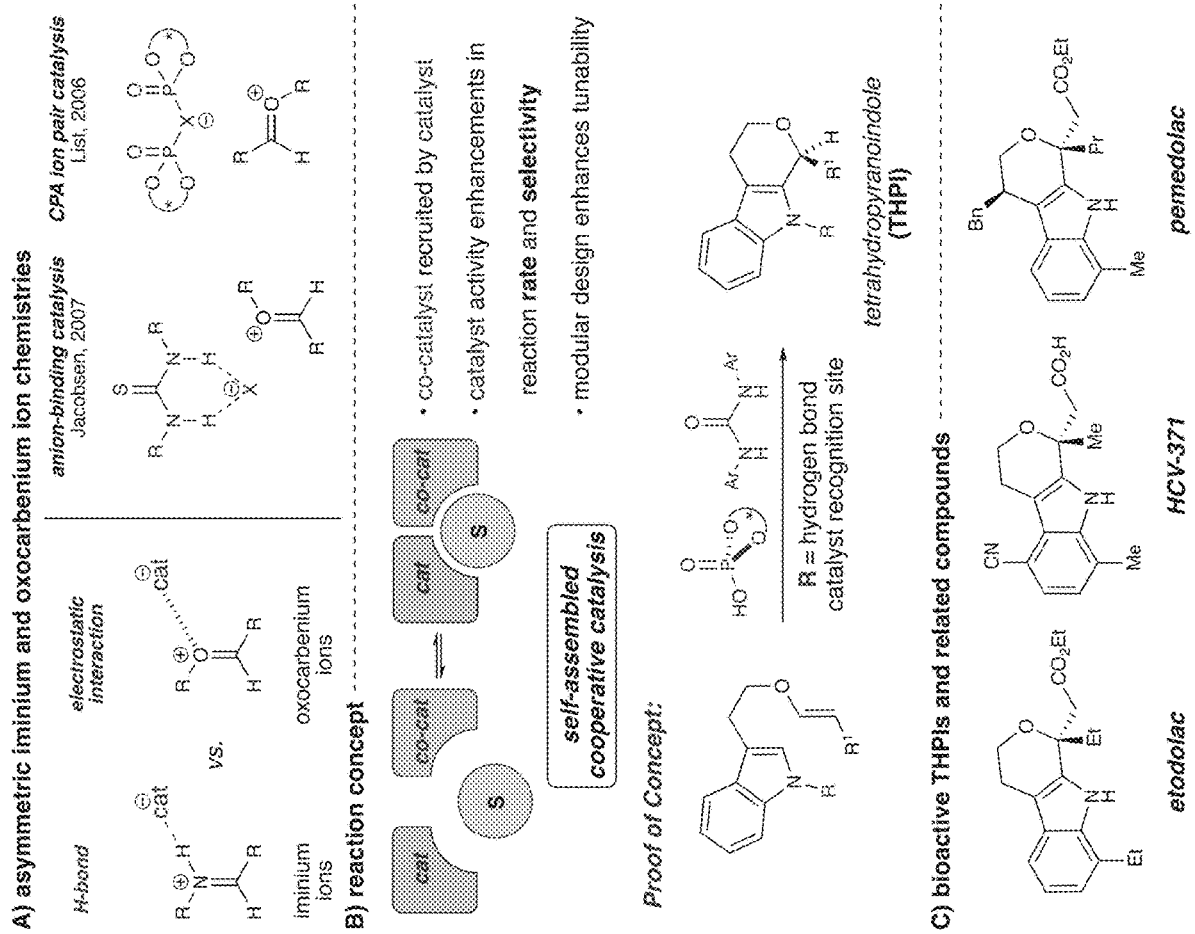
FIG. 1 is a schematic illustration of cooperative catalysis strategies for the control addition of facial selectivity to oxocarbenium ions.

The present invention is described herein using several definitions, as set forth below and throughout the application.

Definitions

The disclosed subject matter may be further described using definitions and terminology as follows. The definitions and terminology used herein are for the purpose of describing particular embodiments only, and are not intended to be limiting.

As used in this specification and the claims, the singular forms "a," "an," and "the" include plural forms unless the context clearly dictates otherwise. For example, the term "a substituent" should be interpreted to mean "one or more substituents," unless the context clearly dictates otherwise.

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

The phrase "such as" should be interpreted as "for example, including." Moreover, the use of any and all exemplary language, including but not limited to "such as", is intended merely to better illuminate the invention and does not pose a limitation on the scope of the invention unless otherwise claimed.

Furthermore, in those instances where a convention analogous to "at least one of A, B and C, etc." is used, in general such a construction is intended in the sense of one having ordinary skill in the art would understand the convention (e.g., "a system having at least one of A, B and C" would include but not be limited to systems that have A alone, B alone, C alone, A and B together, A and C together, B and C together, and/or A, B, and C together). It will be further understood by those within the art that virtually any disjunctive word and/or phrase presenting two or more alternative terms, whether in the description or figures, should be understood to contemplate the possibilities of including one of the terms, either of the terms, or both terms. For example, the phrase "A or B" will be understood to include the possibilities of "A" or 'B or "A and B."

All language such as "up to," "at least," "greater than," "less than," and the like, include the number recited and refer to ranges which can subsequently be broken down into ranges and subranges. A range includes each individual member. Thus, for example, a group having 1-3 members refers to groups having 1, 2, or 3 members. Similarly, a group having 6 members refers to groups having 1, 2, 3, 4, or 6 members, and so forth.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use and aspect of a described embodiment or feature contained in the same, or a definitive decision to use a specific skill regarding a described embodiment or feature contained in the same. In this latter context, the modal verb "may" has the same meaning and connotation as the auxiliary verb "can."

A "subject in need thereof" as utilized herein refers to a subject in need of treatment for a disease or disorder associated with a compound(s) disclosed herein, such as a substituted tetrahydropyranoindole. For example, a "subject in need thereof" may include a subject having a disease, disorder, or symptom associated with pain, swelling, and joint stiffness that is associated with various conditions, such as arthritis. A "subject in need thereof" may include a subject having or at risk for developing a cell proliferative disease or disorder such as cancer. The term "subject" may be used interchangeably with the terms "individual" and "patient" and includes human and non-human mammalian subjects.

Chemical Entities

New chemical entities and uses for chemical entities are disclosed herein. The chemical entities may be described using terminology known in the art and further discussed below.

As used herein, an asterisk "*" or a plus sign "+" may be used to designate the point of attachment for any radical group or substituent group.

The term "alkyl" as contemplated herein includes a straight-chain or branched alkyl radical in all of its isomeric forms, such as a straight or branched group of 1-12, 1-10, or 1-6 carbon atoms, referred to herein as C1-C12 alkyl, C1-C10-alkyl, and C1-C6-alkyl, respectively.

The term "alkylene" refers to a diradical of straight-chain or branched alkyl group (i.e., a diradical of straight-chain or branched $C_1$-C6 alkyl group). Exemplary alkylene groups include, but are not limited to —$CH_2$—, —$CH_2CH_2$—, —$CH_2CH_2CH_2$—, —$CH(CH_3)CH_2$—, —$CH_2CH(CH_3)$ $CH_2$—, —$CH(CH_2CH_3)CH_2$—, and the like.

The term "haloalkyl" refers to an alkyl group that is substituted with at least one halogen. For example, —$CH_2F$, —$CHF_2$, —$CF_3$, —$CH_2CF_3$, —$CF_2CF_3$, and the like.

The term "heteroalkyl" as used herein refers to an "alkyl" group in which at least one carbon atom has been replaced with a heteroatom (e.g., an O, N, or S atom). One type of heteroalkyl group is an "alkoxy" group.

The term "alkenyl" as used herein refers to an unsaturated straight or branched hydrocarbon having at least one carbon-carbon double bond, such as a straight or branched group of 2-12, 2-10, or 2-6 carbon atoms, referred to herein as C2-C12-alkenyl, C2-C10-alkenyl, and C2-C6-alkenyl, respectively.

The term "alkynyl" as used herein refers to an unsaturated straight or branched hydrocarbon having at least one carbon-carbon triple bond, such as a straight or branched group of 2-12, 2-10, or 2-6 carbon atoms, referred to herein as C2-C12-alkynyl, C2-C10-alkynyl, and C2-C6-alkynyl, respectively.

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "C4-8-cycloalkyl," derived from a cycloalkane. Unless specified otherwise, cycloalkyl groups are optionally substituted at one or more ring positions with, for example, alkanoyl, alkoxy, alkyl, haloalkyl, alkenyl, alkynyl, amido or carboxyamido, amidino, amino, aryl, arylalkyl, azido, carbamate, carbonate, carboxy, cyano, cycloalkyl, ester, ether, formyl, halo, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the cycloalkyl group is not substituted, i.e., it is unsubstituted.

The term "cycloheteroalkyl" refers to a monovalent saturated cyclic, bicyclic, or bridged cyclic hydrocarbon group of 3-12, 3-8, 4-8, or 4-6 carbons in which at least one carbon of the cycloalkane is replaced with a heteroatom such as, for example, N, O, and/or S.

The term "cycloalkylene" refers to a cycloalkyl group that is unsaturated at one or more ring bonds.

The term "partially unsaturated carbocyclyl" refers to a monovalent cyclic hydrocarbon that contains at least one double bond between ring atoms where at least one ring of the carbocyclyl is not aromatic. The partially unsaturated carbocyclyl may be characterized according to the number oring carbon atoms. For example, the partially unsaturated carbocyclyl may contain 5-14, 5-12, 5-8, or 5-6 ring carbon atoms, and accordingly be referred to as a 5-14, 5-12, 5-8, or 5-6 membered partially unsaturated carbocyclyl, respectively. The partially unsaturated carbocyclyl may be in the form of a monocyclic carbocycle, bicyclic carbocycle, tricyclic carbocycle, bridged carbocycle, spirocyclic carbocycle, or other carbocyclic ring system. Exemplary partially unsaturated carbocyclyl groups include cycloalkenyl groups and bicyclic carbocyclyl groups that are partially unsaturated. Unless specified otherwise, partially unsaturated carbocyclyl groups are optionally substituted at one or more ring positions with, for example, alkanoyl, alkoxy, alkyl, haloalkyl, alkenyl, alkynyl, amido or carboxyamido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the partially unsaturated carbocyclyl is not substituted, i.e., it is unsubstituted.

The term "aryl" is art-recognized and refers to a carbocyclic aromatic group. Representative aryl groups include phenyl, naphthyl, anthracenyl, and the like. The term "aryl" includes polycyclic ring systems having two or more carbocyclic rings in which two or more carbons are common to two adjoining rings (the rings are "fused rings") wherein at least one of the rings is aromatic and, e.g., the other ring(s) may be cycloalkyls, cycloalkenyls, cycloalkynyls, and/or aryls. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido or carboxyamido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. In certain embodiments, the aromatic ring is substituted at one or more ring positions with halogen, alkyl, hydroxyl, or alkoxyl. In certain other embodiments, the aromatic ring is not substituted, i.e., it is unsubstituted. In certain embodiments, the aryl group is a 6-10 membered ring structure.

The terms "heterocyclyl" and "heterocyclic group" are art-recognized and refer to saturated, partially unsaturated, or aromatic 3- to 10-membered ring structures, alternatively 3- to 7-membered rings, whose ring structures include one to four heteroatoms, such as nitrogen, oxygen, and sulfur. The number of ring atoms in the heterocyclyl group can be specified using 5 Cx-Cx nomenclature where x is an integer specifying the number of ring atoms. For example, a C3-C7 heterocyclyl group refers to a saturated or partially unsaturated 3- to 7-membered ring structure containing one to four heteroatoms, such as nitrogen, oxygen, and sulfur. The designation "C3-C7" indicates that the heterocyclic ring contains a total of from 3 to 7 ring atoms, inclusive of any heteroatoms that occupy a ring atom position.

The terms "amine" and "amino" are art-recognized and refer to both unsubstituted and substituted amines (e.g., mono-substituted amines or di-substituted amines), wherein substituents may include, for example, alkyl, cycloalkyl, heterocyclyl, alkenyl, and aryl.

The terms "alkoxy" or "alkoxyl" are art-recognized and refer to an alkyl group, as defined above, having an oxygen radical attached thereto. Representative alkoxy groups include methoxy, ethoxy, tert-butoxy and the like.

An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, and the like.

The term "carbonyl" as used herein refers to the radical —C(O)—.

The term "oxo" refers to a divalent oxygen atom —O—.

The term "carboxamido" as used herein refers to the radical —C(O)NRR', where R and R' may be the same or different. R and R', for example, may be independently hydrogen, alkyl, aryl, arylalkyl, cycloalkyl, formyl, haloalkyl, heteroaryl, or heterocyclyl.

The term "carboxy" or "carboxyl" as used herein refers to the radical —COOH or its corresponding salts, e.g. —COONa, etc.

The term "amide" or "amido" or "amidyl" as used herein refers to a radical of the form —R$^1$C(O)N(R$^2$)—, —R$^1$C(O)N(R$^2$)R$^3$—, —C(O)NR$^2$R$^3$, or —C(O)NH$_2$, wherein R$^1$, R$^2$ and R$^3$, for example, are each independently hydrogen, alkyl, alkoxy, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, or nitro.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," or "+" or "−" depending on the configuration of substituents around the stereogenic carbon atom and or the optical rotation observed. The present invention encompasses various stereo isomers of these compounds and mixtures thereof. Stereoisomers include enantiomers and diastereomers. Mixtures of enantiomers or diastereomers may be designated (±)" in nomenclature, but the skilled artisan will recognize that a structure may denote a chiral center implicitly. It is understood that graphical depictions of chemical structures, e.g., generic chemical structures, encompass all stereoisomeric forms of the specified compounds, unless indicated otherwise. Also contemplated herein are compositions comprising, consisting essentially of, or consisting of an enantiopure compound, which composition may comprise, consist essential of, or consist of at least about 50%, 60%, 70%, 80%, 90%, 95%, 96%, 97%, 98%, 99%, or 100% of a single enantiomer of a given compound (e.g., at least about 99% of an R enantiomer of a given compound).

Pharmaceutical Compositions and Formulations

The compounds employed in the compositions and methods disclosed herein may be administered as pharmaceutical compositions and, therefore, pharmaceutical compositions incorporating the compounds are considered to be embodiments of the compositions disclosed herein. Such compositions may take any physical form which is pharmaceutically acceptable; illustratively, they can be orally administered pharmaceutical compositions. Such pharmaceutical compositions contain an effective amount of a disclosed compound, which effective amount is related to the daily dose of the compound to be administered. Each dosage unit may contain the daily dose of a given compound or each dosage unit may contain a fraction of the daily dose, such as one-half or one-third of the dose. The amount of each compound to be contained in each dosage unit can depend, in part, on the identity of the particular compound chosen for the therapy and other factors, such as the indication for which it is given. The pharmaceutical compositions disclosed herein may be formulated so as to provide quick, sustained, or delayed release of the active ingredient after administration to the patient by employing well known procedures.

The compounds for use according to the methods of disclosed herein may be administered as a single compound or a combination of compounds. For example, a compound that modulates the tetrahydropyranoindoles activity may be administered as a single compound or in combination with another compound that modulates tetrahydropyranoindoles activity or that has a different pharmacological activity.

As indicated above, pharmaceutically acceptable salts of the compounds are contemplated and also may be utilized in the disclosed methods. The term "pharmaceutically acceptable salt" as used herein, refers to salts of the compounds which are substantially non-toxic to living organisms. Typical pharmaceutically acceptable salts include those salts prepared by reaction of the compounds as disclosed herein with a pharmaceutically acceptable mineral or organic acid or an organic or inorganic base. Such salts are known as acid addition and base addition salts. It will be appreciated by the skilled reader that most or all of the compounds as disclosed herein are capable of forming salts and that the salt forms of pharmaceuticals are commonly used, often because they are more readily crystallized and purified than are the free acids or bases.

Acids commonly employed to form acid addition salts may include inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of suitable pharmaceutically acceptable salts may include the sulfate, pyrosulfate, bisulfate, sulfite, bisulfate, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleat-, butyne-.1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, α-hydroxybutyrate, glycolate, tartrate, methanesulfonate, propanesulfonate, naphthalene-1-sulfonate, naphthalene-2-sulfonate, mandelate, and the like.

Base addition salts include those derived from inorganic bases, such as ammonium or alkali or alkaline earth metal hydroxides, carbonates, bicarbonates, and the like. Bases useful in preparing such salts include sodium hydroxide, potassium hydroxide, ammonium hydroxide, potassium carbonate, sodium carbonate, sodium bicarbonate, potassium bicarbonate, calcium hydroxide, calcium carbonate, and the like.

The particular counter-ion forming a part of any salt of a compound disclosed herein is may not be critical to the activity of the compound, so long as the salt as a whole is pharmacologically acceptable and as long as the counterion does not contribute undesired qualities to the salt as a whole. Undesired qualities may include undesirably solubility or toxicity.

Pharmaceutically acceptable esters and amides of the compounds can also be employed in the compositions and methods disclosed herein. Examples of suitable esters include alkyl, aryl, and aralkyl esters, such as methyl esters, ethyl esters, propyl esters, dodecyl esters, benzyl esters, and the like. Examples of suitable amides include unsubstituted amides, monosubstituted amides, and disubstituted amides, such as methyl amide, dimethyl amide, methyl ethyl amide, and the like.

In addition, the methods disclosed herein may be practiced using solvate forms of the compounds or salts, esters, and/or amides, thereof. Solvate forms may include ethanol solvates, hydrates, and the like.

The pharmaceutical compositions may be utilized in methods of treating a disease or disorder associated with the substituted tetrahydropyranoindole's activity. As used herein, the terms "treating" or "to treat" each mean to alleviate symptoms, eliminate the causation of resultant symptoms either on a temporary or permanent basis, and/or to prevent or slow the appearance or to reverse the progression or severity of resultant symptoms of the named disease or disorder. As such, the methods disclosed herein encompass both therapeutic and prophylactic administration.

An effective amount can be readily determined by the attending diagnostician, as one skilled in the art, by the use of known techniques and by observing results obtained under analogous circumstances. In determining the effective amount or dose of compound administered, a number of factors can be considered by the attending diagnostician, such as: the species of the subject; its size, age, and general health; the degree of involvement or the severity of the disease or disorder involved; the response of the individual subject; the particular compound administered; the mode of administration; the bioavailability characteristics of the preparation administered; the dose regimen selected; the use of concomitant medication; and other relevant circumstances.

A typical daily dose may contain from about 0.01 mg/kg to about 100 mg/kg (such as from about 0.05 mg/kg to about 50 mg/kg and/or from about 0.1 mg/kg to about 25 mg/kg) of each compound used in the present method of treatment.

Compositions can be formulated in a unit dosage form, each dosage containing from about 1 to about 500 mg of each compound individually or in a single unit dosage form, such as from about 5 to about 300 mg, from about 10 to about 100 mg, and/or about 25 mg. The term "unit dosage form" refers to a physically discrete unit suitable as unitary dosages for a patient, each unit containing a predetermined quantity of active material calculated to produce the desired therapeutic effect, in association with a suitable pharmaceutical carrier, diluent, or excipient.

Oral administration is an illustrative route of administering the compounds employed in the compositions and methods disclosed herein. Other illustrative routes of administration include transdermal, percutaneous, intravenous, intramuscular, intranasal, buccal, intrathecal, intracerebral, or intrarectal routes. The route of administration may be varied in any way, limited by the physical properties of the compounds being employed and the convenience of the subject and the caregiver.

As one skilled in the art will appreciate, suitable formulations include those that are suitable for more than one route of administration. For example, the formulation can be one that is suitable for both intrathecal and intracerebral administration. Alternatively, suitable formulations include those that are suitable for only one route of administration as well as those that are suitable for one or more routes of administration, but not suitable for one or more other routes of administration. For example, the formulation can be one that is suitable for oral, transdermal, percutaneous, intravenous, intramuscular, intranasal, buccal, and/or intrathecal administration but not suitable for intracerebral administration.

The inert ingredients and manner of formulation of the pharmaceutical compositions are conventional. The usual methods of formulation used in pharmaceutical science may be used here. All of the usual types of compositions may be used, including tablets, chewable tablets, capsules, solutions, parenteral solutions, intranasal sprays or powders, troches, suppositories, transdermal patches, and suspensions. In general, compositions contain from about 0.5% to about 50% of the compound in total, depending on the desired doses and the type of composition to be used. The amount of the compound, however, is best defined as the "effective amount", that is, the amount of the compound which provides the desired dose to the patient in need of such treatment. The activity of the compounds employed in the compositions and methods disclosed herein are not believed to depend greatly on the nature of the composition, and, therefore, the compositions can be chosen and formulated primarily or solely for convenience and economy.

Capsules are prepared by mixing the compound with a suitable diluent and filling the proper amount of the mixture in capsules. The usual diluents include inert powdered substances (such as starches), powdered cellulose (especially crystalline and microcrystalline cellulose), sugars (such as fructose, mannitol and sucrose), grain flours, and similar edible powders.

Tablets are prepared by direct compression, by wet granulation, or by dry granulation. Their formulations usually incorporate diluents, binders, lubricants, and disintegrators (in addition to the compounds). Typical diluents include, for example, various types of starch, lactose, mannitol, kaolin, calcium phosphate or sulfate, inorganic salts (such as sodium chloride), and powdered sugar. Powdered cellulose derivatives can also be used. Typical tablet binders include substances such as starch, gelatin, and sugars (e.g., lactose, fructose, glucose, and the like). Natural and synthetic gums can also be used, including acacia, alginates, methylcellulose, polyvinylpyrrolidine, and the like. Polyethylene glycol, ethylcellulose, and waxes can also serve as binders.

Tablets can be coated with sugar, e.g., as a flavor enhancer and sealant. The compounds also may be formulated as chewable tablets, by using large amounts of pleasant-tasting substances, such as mannitol, in the formulation. Instantly dissolving tablet-like formulations can also be employed, for example, to assure that the patient consumes the dosage form and to avoid the difficulty that some patients experience in swallowing solid objects.

A lubricant can be used in the tablet formulation to prevent the tablet and punches from sticking in the die. The lubricant can be chosen from such slippery solids as talc, magnesium and calcium stearate, stearic acid, and hydrogenated vegetable oils.

Tablets can also contain disintegrators. Disintegrators are substances that swell when wetted to break up the tablet and release the compound. They include starches, clays, celluloses, algins, and gums. As further illustration, corn and potato starches, methylcellulose, agar, bentonite, wood cellulose, powdered natural sponge, cation-exchange resins, alginic acid, guar gum, citrus pulp, sodium lauryl sulfate, and carboxymethylcellulose can be used.

Compositions can be formulated as enteric formulations, for example, to protect the active ingredient from the strongly acid contents of the stomach. Such formulations can be created by coating a solid dosage form with a film of a polymer which is insoluble in acid environments and soluble in basic environments. Illustrative films include cellulose acetate phthalate, polyvinyl acetate phthalate, hydroxypropyl methylcellulose phthalate, and hydroxypropyl methylcellulose acetate succinate.

Transdermal patches can also be used to deliver the compounds. Transdermal patches can include a resinous composition in which the compound will dissolve or partially dissolve; and a film which protects the composition and which holds the resinous composition in contact with the skin. Other, more complicated patch compositions can also be used, such as those having a membrane pierced with a plurality of pores through which the drugs are pumped by osmotic action.

As one skilled in the art will also appreciate, the formulation can be prepared with materials (e.g., actives excipients, carriers (such as cyclodextrins), diluents, etc.) having properties (e.g., purity) that render the formulation suitable for administration to humans. Alternatively, the formulation can be prepared with materials having purity and/or other properties that render the formulation suitable for administration to non-human subjects, but not suitable for administration to humans.

Substituted Tetrahydropyranoindoles, Derivatives Thereof, and Their Methods of Synthesis and Use Disclosed herein are tetrahydropyranoindole compounds and derivatives thereof, as well as their methods of use and synthesis. The disclosed tetrahydropyranoindole compounds may have a formula as follows or a salt, a hydrate, or a spirolactam derivative thereof:

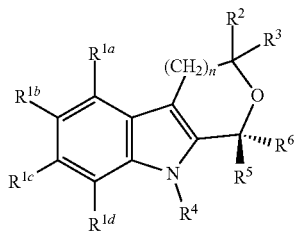

wherein: $R^{1a}$, $R^{1b}$, $R^{1c}$, and $R^{1d}$ are independently selected from hydrogen, alkyl, halo, haloalkyl, and alkoxy, wherein optionally at least one of $R^{1a}$, $R^{1b}$, $R^{1c}$, and $R^{1d}$ is not hydrogen; $R^2$ and $R^3$ are independently selected from hydrogen or alkyl, optionally wherein at least one of $R^2$ and $R^3$ is not hydrogen; $R^4$ is selected from hydrogen, alkyl, carboxy, carboxyalkyl, carboxamido, and carboxamidoaryl, which aryl substituent optionally is substituted with haloalkyl (e.g., trifluoromethyl such as 3,5-bis(trifluoromethyl)phenyl); $R^5$ and $R^6$ are independently selected from hydrogen and alkyl, wherein optionally at least one of $R^5$ and $R^6$ is not hydrogen; and n is an integer selected from 1 and 2.

In some embodiments of the disclosed tetrahydropyranoindole compounds, at least one of $R^{1a}$, $R^{1b}$, $R^{1c}$, and $R^{1d}$ is a branched or unbranched $C_{1-6}$-alkyl, such as methyl. In some embodiments, at least one of $R^{1a}$, $R^{1b}$, $R^{1c}$, and $R^{1d}$ is halo, for example, wherein at least one of $R^{1a}$, $R^{1b}$, $R^{1c}$, and $R^{1d}$ is selected from fluoro, chloro, and bromo. In some embodiments, at least one of $R^{1a}$, $R^{1b}$, $R^{1c}$, and $R^{1d}$ is haloalkyl, for example, wherein at least one of $R^{1a}$, $R^{1b}$, $R^{1c}$, and $R^{1d}$ is trifluoromethyl. In some embodiments, at least one of $R^{1a}$, $R^{1b}$, $R^{1c}$, and $R^{1d}$ is a branched or unbranched $C_{1-6}$-alkoxy, such as methoxy. In some embodiments, all of $R^{1a}$, $R^{1b}$, $R^{1c}$, and $R^{1d}$ are hydrogen.

In some embodiments of the disclosed tetrahydropyranoindole compounds, at least one of $R^2$ and $R^3$ is a branched or unbranched $C_{1-6}$-alkyl, such as methyl. In some embodiments, each of $R^2$ and $R^3$ is a branched or unbranched $C_{1-6}$-alkyl, such as methyl. In further embodiments, at least one of $R^2$ and $R^3$ hydrogen. In even further embodiments, each of $R^2$ and $R^3$ is hydrogen.

In the disclosed tetrahydropyranoindole compounds, $R^4$ is selected from alkyl, carboxy, carboxyalkyl, carboxamido, and carboxamidoaryl, which aryl substituent optionally is substituted with haloalkyl. In some embodiments, $R^4$ is a branched or unbranched $C_{1-6}$-alkyl. In further embodiments, $R^4$ is a branched or unbranched carboxy-$C_{1-6}$-alkyl. In some embodiments, $R^4$ is —C(O)NR$_7$R$_8$ where $R^7$ and $R^8$ are independently selected from hydrogen, alkyl, and aryl, and which aryl optionally is substituted with haloalkyl. In some embodiments, at least one of $R^7$ and $R^8$ is aryl optionally substituted with haloalkyl, such as branched or unbranched halo-$C_{1-6}$-alkyl. In some non-limiting examples, the branched or unbranched halo-$C_{1-6}$-alkyl is trifluromethyl, for example wherein at least one of $R^7$ and $R^8$ is 3,5-bis(trifluoromethyl)phenyl.

In the disclosed tetrahydropyranoindole compounds, $R^5$ and $R^6$ are independently selected from hydrogen and alkyl. In some embodiments, $R^5$ and $R^6$ are independently selected from branched or unbranched $C_{1-6}$-alkyl, such as methyl or ethyl. In some embodiments, at least one of $R^5$ and $R^6$ is not hydrogen.

In some embodiments of the disclosed subject matter, the compound of formula I is present in an enantiopure composition, where the composition does not comprise a compound having as stereochemistry that differs from the compound of formula I. In other embodiments, the compound of formula I is present in a composition comprising a racemic mixtures of enantiomeric compounds where the compound of formula is the dominant enantiomer in the mixture enantiomeric compounds. In some embodiments, the compound of formula I represents at least about 50%, or at least 60%, or at least 70% or at least 80%, or at least 90%, or at least 95%, or at least 98%, or at least 99%, or more of the enantiomeric compounds in the racemic mixture.

Exemplary tetrahydropyranoindole compounds as contemplated herein may include, but are not limited to compounds having a formula selected from the following or a salt, a hydrate, or a spirolactam derivative thereof:

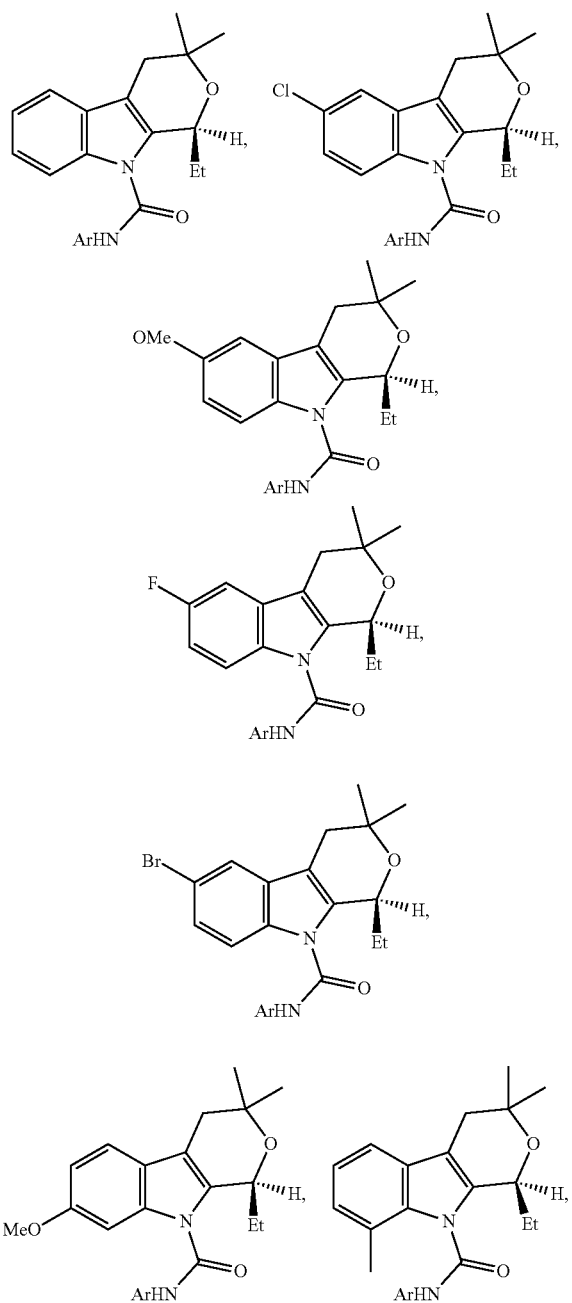

-continued

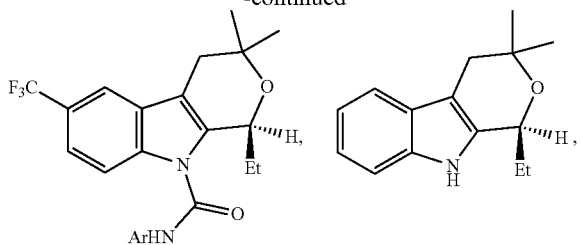

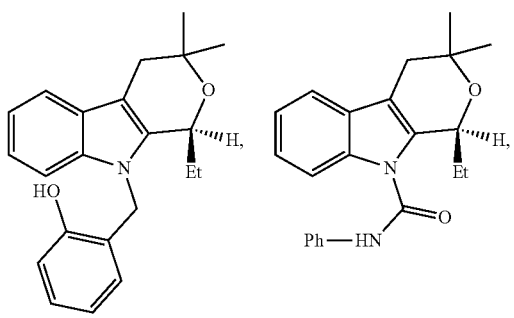

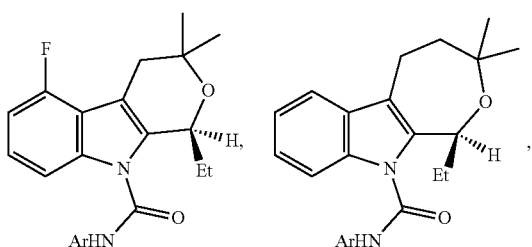

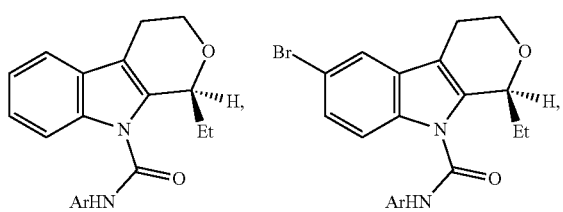

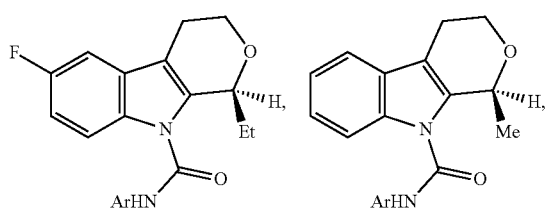

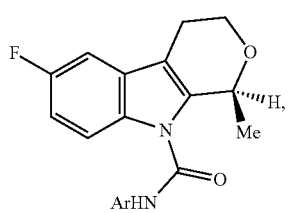

and wherein Ar is 3,5-bis(trifluoromethyl)phenyl.

In some embodiments, the disclosed compounds may include spirolactam derivatives of the tetrahydropyranoindole compounds having a formula as follows:

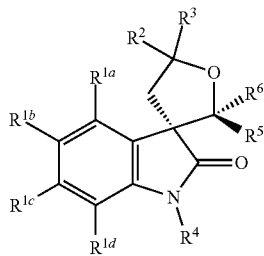

or oxidized derivatives having a formula,

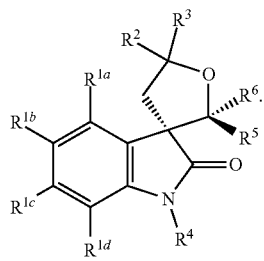

or a salt or a hydrate thereof.

The disclosed tetrahydropyranoindole compounds may be synthesized by methods that utilize a cooperative hydrogen bond donor/Brønsted acid system. In some embodiments, the disclosed tetrahydropyranoindole compounds may be synthesized by methods that include reacting:
(a) a compound of a formula:

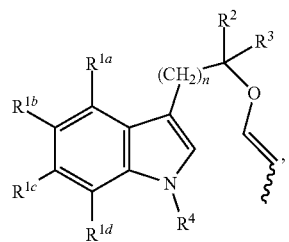

wherein $R^9$ is hydrogen or alkyl;
(b) a chiral phosphoric acid (CPA); and
(c) a substituted urea, optionally an aryl substituted urea, optionally 1,3-bis(3,5-bis(trifluoromethyl)phenyl)urea; thereby forming the disclosed tetrahydropyranoindole compounds.

The disclosed tetrahydropyranoindole compounds, salts, hydrates, and spirolactam derivatives thereof may be formulated as pharmaceutical compositions comprising the compounds, salts, hydrates, and spirolactam derivatives, in a pharmaceutically acceptable carrier, diluent, or excipient. The pharmaceutical compositions may be formulated for treating diseases, disorders, or symptoms in a subject in need thereof, such as but not limited to relieving pain, swelling, and joint stiffness that is associated with various conditions, such as arthritis. The pharmaceutical compositions also may be formulated for treating cell proliferative diseases and disorders such as cancer. In some embodiments, the disclosed tetrahydropyranoindole compounds may be used for treating a subject in need of treatment. The method includes administering the disclosed compound(s) to the subject in an effective amount to treat the disease or disorder or the symptom thereof.

ILLUSTRATED EMBODIMENTS

The following Embodiments are illustrative and should not be interpreted to limit the claimed subject matter.

Embodiment 1. A compound of the following formula or a salt, a hydrate, or a spirolactam derivative thereof:

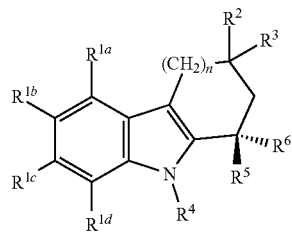

wherein $R^{1a}$, $R^{1b}$, $R^{1c}$, and Rd are independently selected from hydrogen, alkyl, halo, haloalkyl, and alkoxy, wherein optionally at least one of $R^{1a}$, $R^{1b}$, $R^{1c}$, and $R^{1d}$ is not hydrogen, $R^2$ and $R^3$ are independently selected from hydrogen or alkyl, optionally wherein at least one of $R^2$ and $R^3$ is not hydrogen, $R^4$ is selected from hydrogen, alkyl, carboxy, carboxyalkyl, carboxamido, and carboxamidoaryl, which aryl substituent optionally is substituted with haloalkyl, $R^5$ and $R^6$ are independently selected from hydrogen and alkyl, wherein optionally at least one of $R^5$ and $R^6$ is not hydrogen, and n is an integer selected from 1 and 2.

Embodiment 2. The compound of embodiment 1, wherein at least one of $R^{1a}$, $R^{1b}$, $R^{1c}$, and $R^{1d}$ is is fluoro.

Embodiment 3. The compound of embodiment 1, wherein at least one of $R^{1a}$, $R^{1b}$, $R^{1c}$, and $R^{1d}$ is bromo.

Embodiment 4. The compound of embodiment 1, wherein at least one of $R^{1a}$, $R^{1b}$, $R^{1c}$, and $R^{1d}$ is a branched or unbranched $C_{1-6}$-alkyl.

Embodiment 5. The compound of embodiment 4, wherein at least one of $R^{1a}$, $R^{1b}$, $R^{1c}$, and $R^{1d}$ is methyl.

Embodiment 6. The compound of embodiment 1, wherein at least one of $R^{1a}$, $R^{1b}$, $R^{1c}$, and $R^{1d}$ is a branched or unbranched $C_{1-6}$-alkoxy.

Embodiment 7. The compound of embodiment 6, wherein at least one of $R^{1a}$, $R^{1b}$, $R^{1c}$, and $R^{1d}$ is methoxy.

Embodiment 8. The compound of embodiment 1, wherein at least one of $R^{1a}$, $R^{1b}$, $R^{1c}$, and $R^{1d}$ is haloalkyl.

Embodiment 9. The compound of embodiment 8, wherein at least one of $R^{1a}$, $R^{1b}$, $R^{1c}$, and $R^{1d}$ is —$CF_3$.

Embodiment 10. The compound of embodiment 1, wherein at least one of $R^2$ and $R^3$ is branched or unbranched $C_{1-6}$-alkyl.

Embodiment 11. The compound of embodiment 1, wherein each of $R^2$ and $R^3$ are branched or unbranched $C_{1-6}$-alkyl.

Embodiment 12. The compound of embodiment 1, wherein each of $R^2$ and $R^3$ is methyl.

Embodiment 13. The compound of embodiment 1, wherein at least one of $R^5$ and $R^6$ is hydrogen.

Embodiment 14. The compound of embodiment 1, wherein at least one of $R^5$ and $R^6$ is a branched or unbranched $C_{1-6}$-alkyl.

Embodiment 15. The compound of embodiment 14, wherein at least one of $R^5$ and $R^6$ is ethyl.

Embodiment 16. The compound of embodiment 14, wherein at least one of $R^5$ and $R^6$ is methyl.

Embodiment 17. The compound of embodiment 1, wherein $R^4$ is —$C(O)NR^7(R^8)$, wherein $R^7$ is hydrogen and $R^8$ is aryl optionally substituted at one or more positions with trifluoromethyl.

Embodiment 18. The compound of embodiment 17, wherein $R^8$ is 3,5-bis(trifluoromethyl)phenyl.

Embodiment 19. The compound of embodiment 1, wherein the compound is selected from the group consisting of:

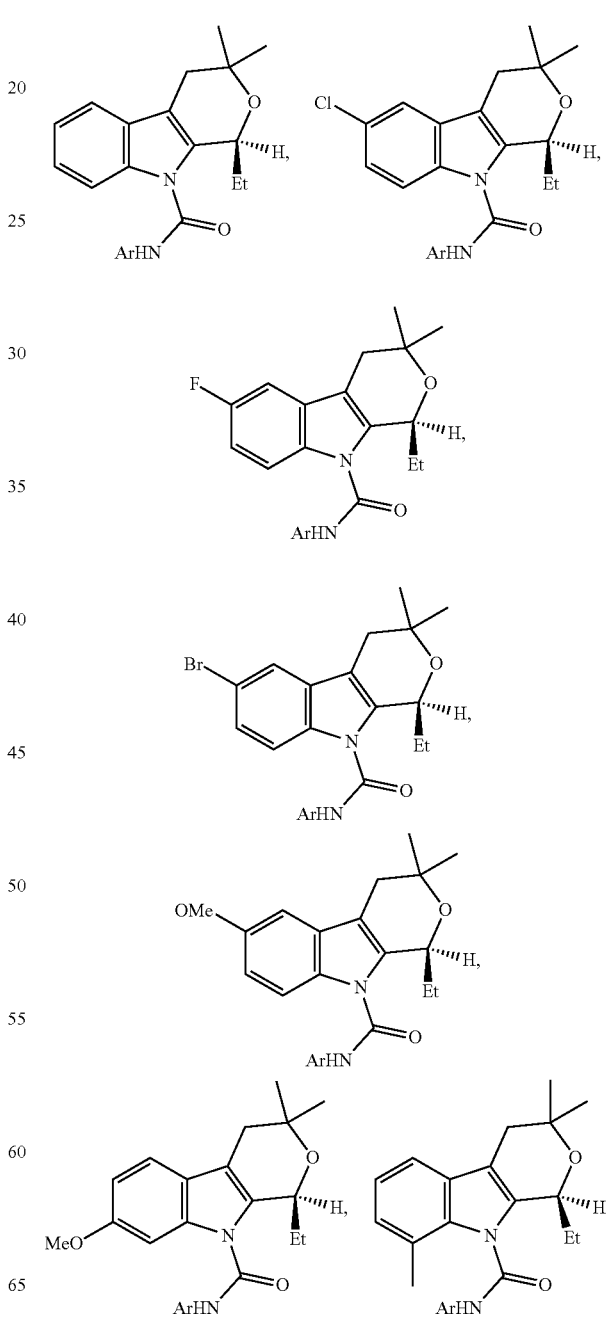

-continued

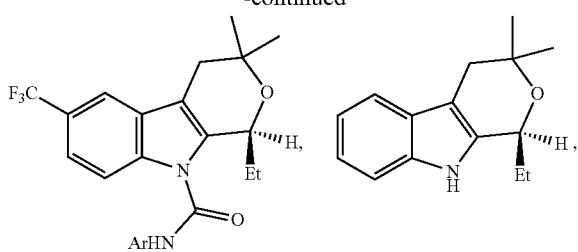

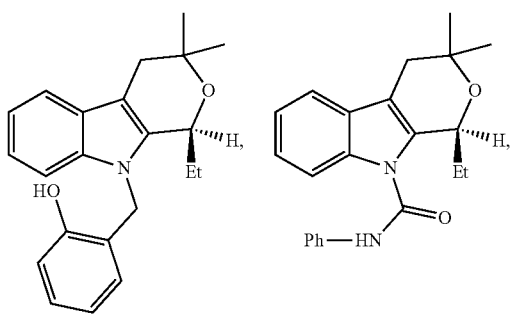

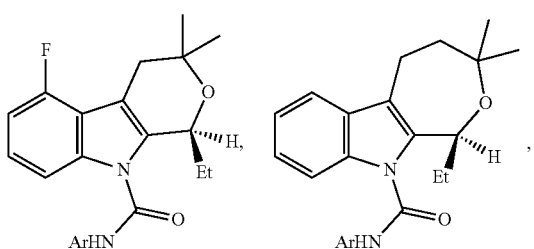

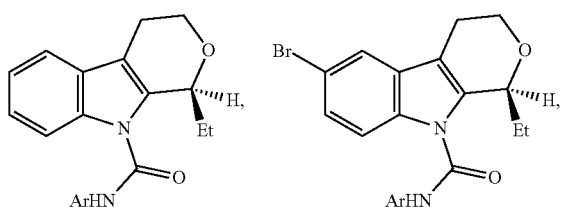

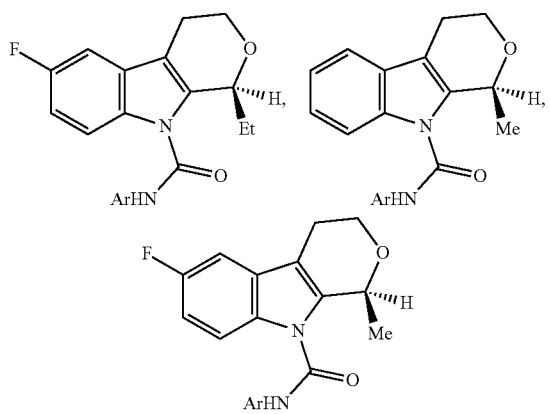

and wherein Ar is 3,5-bis(trifluoromethyl)phenyl.

Embodiment 20. A spirolactam derivative of any of the foregoing compounds having a formula:

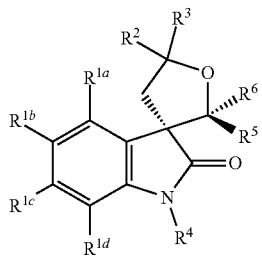

Embodiment 21. An oxidized form of the spirolactam derivative of embodiment 18 having a formula:

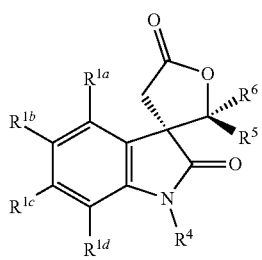

Embodiment 22. An enantiomerically pure composition comprising or consisting of the compound of any of the foregoing embodiments.

Embodiment 23. A racemic mixture of compounds comprising the compound of any of the foregoing embodiments, wherein the compound represents at least about 80%, 85%, 90%, 95%, 96%, 97%, 98%, or 99% of the racemic mixture of compounds.

Embodiment 24. A pharmaceutical composition comprising: (a) an effective amount of: (i) the compound of any of embodiments 1-23; (ii) the enantiomerically pure composition of embodiment 20; and/or (iii) the racemic mixture of embodiment 21; and (b) at least one of a carrier, excipient, or diluent.

Embodiment 25. A method of treating a subject having a disease or disorder and in need of treatment, the method comprising administering to the subject the pharmaceutical composition of embodiment 24.

Embodiment 26. A method of synthesizing any of the compounds of embodiments of embodiments 1-25, the method comprising reacting:

(a) a compound of a formula:

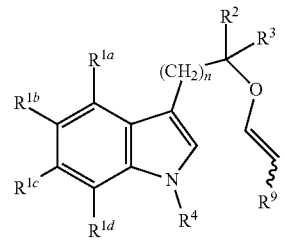

wherein $R^9$ is hydrogen or alkyl, (b) a chiral phosphoric acid (CPA), and (c) a substituted urea, optionally an aryl substituted urea, optionally 1,3-bis(3,5-bis(trifluoromethyl)phenyl)urea.

EXAMPLES

The following Examples are illustrative and are not intended to limit the scope of the claimed subject matter.

Reference is made to the manuscript Maskeri et al., "A Cooperative Hydrogen Bond Donor/Brønsted Acid System for the Enantioselective Synthesis of Tetrahydropyrans," Angew Chem Int Ed Enl. 2018 Dec. 21; 57(52):17225-17229; the content of which is incorporated herein by reference in its entirety.

Abstract

Carbocations stabilized by adjacent oxygen atoms are useful reactive intermediates involved in fundamental chemical transformations. These oxocarbenium ions typically lack sufficient electron density to engage established chiral Brønsted or Lewis acid catalysts, presenting a major challenge to their widespread application in asymmetric catalysis. Leading methods for selectivity operate primarily through electrostatic pairing between the oxocarbenium ion and a chiral counterion. A general approach to new enantioselective transformations of oxocarbenium ions requires novel strategies that address the weak binding capabilities of these intermediates. We demonstrate herein a novel cooperative catalysis system for selective reactions with oxocarbenium ions. This new strategy has been applied to a highly selective and rapid oxa-Pictet-Spengler reaction and highlights a powerful combination of an achiral hydrogen bond donor with a chiral Brønsted acid.

Introduction

Oxygen-stabilized carbocations—oxocarbenium ions—are highly reactive intermediates in many established chemical transformations. These potent electrophiles are typically formed in situ, and the control of asymmetric induction in reactions of prochiral oxocarbenium ions remains a significant challenge in chemical synthesis. Unlike their nitrogen-stabilized counterparts—iminium ions—to which nucleophilic addition is typically governed by the dual application of hydrogen bonding and catalyst-substrate electrostatic interactions,[1] oxocarbenium ions have been manipulated predominantly via electrostatic interactions (FIG. 1A).[2] Prevailing perceptions regarding the relatively weak electrostatic interaction between organic oxocarbenium/counterion complexes have contributed to a dearth of methods for asymmetric oxocarbenium ion chemistry, though these notions have been challenged in recent years.[3]

Pioneering work by Jacobsen detailed the ability of urea-based chiral anion-receptor catalysts to promote the enantioselective addition of silyl ketene acetals to oxocarbenium ions generated in situ.[4] This report has been followed by several applications of chiral anion-binding catalysts in asymmetric reactions invoking oxocarbenium ion intermediates, though these reports are only known to be compatible with substrates that produce stabilized, conjugated ionic intermediates (e.g., benzylic or aromatic (pyrylium)-type intermediates).[5]

Brønsted and Lewis acid catalysis are alternative approaches to generate chiral oxocarbenium ions, though the majority of these have similar limitations as anion-binding catalysis, or are constrained to cyclic frameworks.[6] Notable exceptions include the use of highly constrained chiral imidodiphosphate-derived Brønsted acid catalysts pioneered by List, which uniquely engage non-stabilized oxocarbenium precursors in some cases through sequestration of the reactive intermediate.[7] Several advances have also been made employing chiral nucleophiles with achiral oxocarbenium ion precursors.[8]

Discussion

In some embodiments, presented herein is an alternative strategy to induce stereocontrol in oxocarbenium additions may be achieved by augmenting the presumed weak electrostatic ion-pairing interactions with favourable hydrogen bonds proximal to the oxocarbenium ion (FIG. 1B). This approach would enable the substrate to recruit chiral co-catalysts[10] in a self-assembled motif, ultimately controlling the oxocarbenium ion geometry. To this end, we present a reaction design including a hydrogen-bonding co-catalyst geared to cooperatively enhance, define, and prolong the lifetime of substrate-catalyst interactions.

For our initial investigations, we selected the oxa-Pictet-Spengler reaction[11] as a test platform for our hypotheses. To date, only two examples of enantioselective oxa-Pictet-Spengler reactions have been reported.[12] While highly selective, these reactions require several days to achieve acceptable conversions, which is likely attributable to the stability of on-cycle intermediates relative to the higher-energy oxocarbenium ions.[12b] We recently developed a cooperative catalysis approach to generate oxocarbenium ions through the tandem isomerization-protonation of allyl ethers.[13] Building on this approach, we set out to develop an asymmetric oxa-Pictet-Spengler reaction using tethered ethers as oxocarbenium ion precursors and aryl nucleophiles possessing hydrogen-bonding sites.

Herein, we describe a cooperative catalytic system that exploits the hydrogen bonding capabilities of ureas in conjunction with a simple chiral phosphoric acid (CPA) catalyst [14] to facilitate an exceptionally rapid, mild, and enantioselective intramolecular oxa-Pictet-Spengler reaction. This reaction provides novel strategic routes to chiral, heterocyclic motifs that are prevalent in bioactive small molecules (FIG. 1C),[15] exemplified by the application to the concise total synthesis of the natural product coixspirolactam C.[16]

Our initial studies of tetrahydropyranoindole (THPI) precursor indole vinyl ethers examined the cyclization of the N—H species catalyzed by a CPA (FIG. 2, entry 1). These early studies found the resulting THPI was produced in low yield (27%), and the product exhibited little-to-no enantioenrichment (51:49 enantiomeric ratio [e.r.]). Based on early work demonstrating the hydrogen-bonding capabilities of CPAs,[14a] we hypothesized the possibility of mapping the hydrogen bonding observed in iminium ion chemistries to oxocarbenium ions through the use of a pendent hydrogen bond donor (HBD). Initial screens including hydrogen bonding motifs on substrates showed promise (entries 2-3), and the use of R=bis-3,5-(trifluoromethyl)carboxamide on gem-dimethyl substrates led to an increased e.r. and yield of the product (67%, 68:32; entry 4).

With a new method established to recruit an optimal CPA via hydrogen bonding, we began to explore the capabilities of small molecule co-catalysts to modulate the presumed CPA/substrate complex. Given the Lewis basicity of the CPA phosphate, we anticipated that an exogenous HBD might coordinate to the CPA,[17] allowing us to readily alter the steric and electronic parameters of the CPA.[18] Gratifyingly, a screen of hydrogen-bonding additives furnished 1,3-bis(3,5-bis(trifluoromethyl) phenyl)urea,[19] which afforded the product in 89% yield with 97:3 e.r. (entry 6). Notably, the optimal reaction was complete in under 15 minutes (vs 12+h for the non-HBD processes). Omission of the substrate-bound carboxamide is substantially detrimental to this cyclization, dramatically reducing yield and selectivity, (entry 7) whereas blocking the H-bonding site of the indole N-carboxamide with a methyl group shut down the reaction altogether (entry 8), underscoring the importance of hydrogen bonding for the efficacy of this process.

Figure 3:
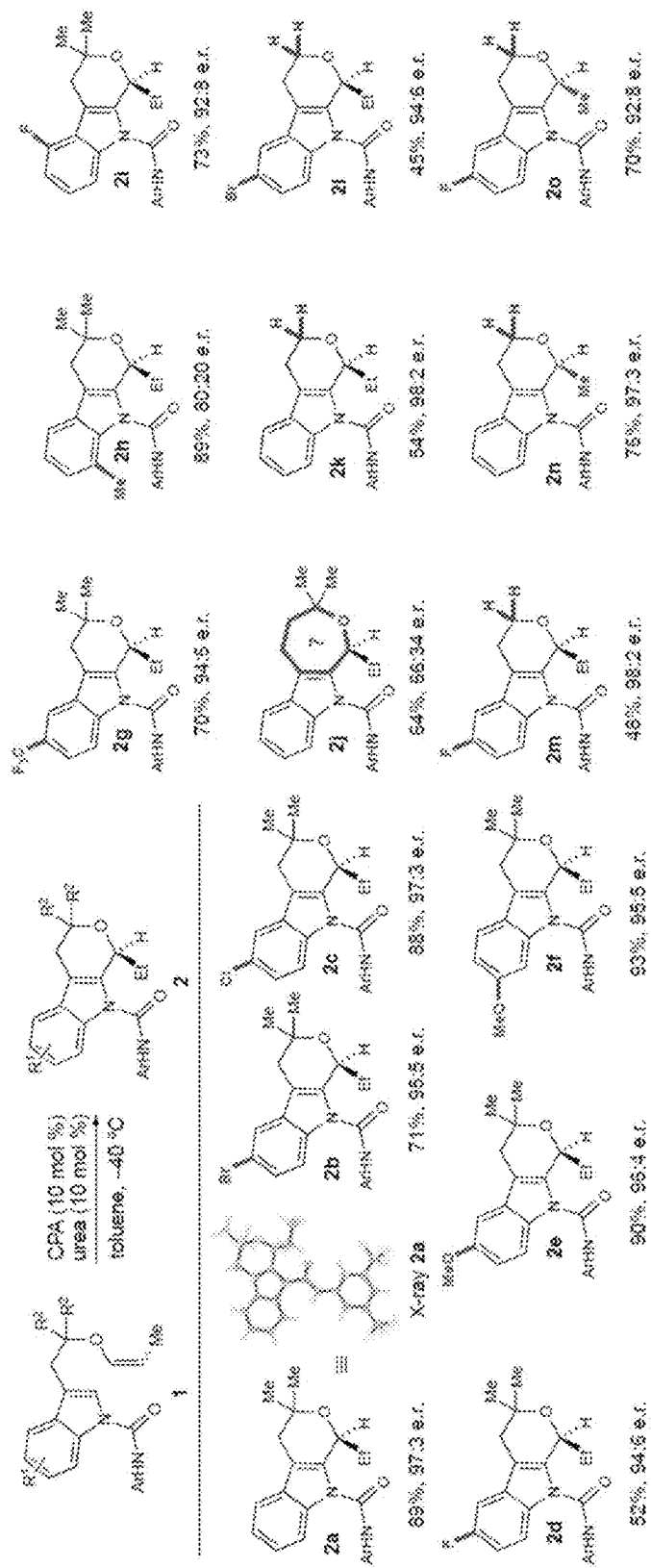
FIG. 3 is a schematic illustration of an exemplary reaction pathway and example tetrahydropyranoindole compounds in accordance with some embodiments of the present disclosure.
Figure 4:
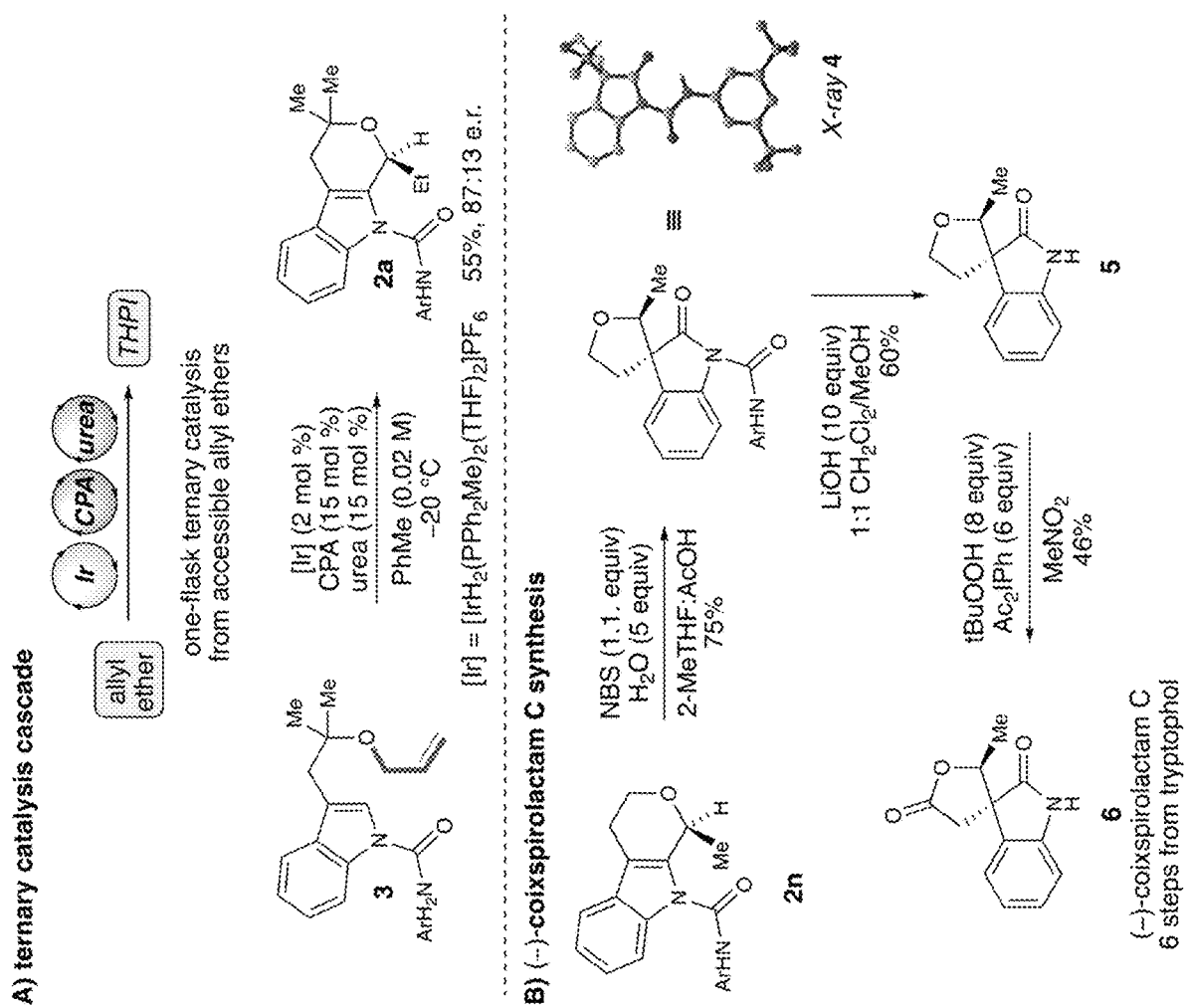
FIG. 4 is a schematic illustration of an exemplary reaction pathway for producing example tetrahydropyranoindole and spirolactam compounds in accordance with some embodiments of the present disclosure. A) ternary catalysis cascade; B) (−)-coixspirolactam C synthesis.

With these optimal reaction conditions, we explored the scope of this method (FIG. 3). Halogen-substituted, electron-donating, and electron-deficient indoles were well tolerated in this cyclization exhibiting good to excellent yields with excellent e.r. It is important to note that (5-F)- and (5-CF$_3$)-substituted indole substrates (2g and 2m) performed admirably, as these electron-withdrawn substitutions have not been shown to generate the corresponding products using other enantioselective approaches.[12a, 20] Similarly, the 7-methyl product 2h and oxepine 2j were smoothly synthesized, though with reduced e.r. We were additionally pleased to find that our optimized conditions efficiently promoted the formation of desmethyl products 2k-2m with no erosion in enantioselectivity, though with diminished yield presumably due to the absence of Thorpe-Ingold angle compression.[21] Finally, subjecting terminal vinyl ether analogues of 1 to the cyclization likewise afforded methyl-substituted pyranoindoles in good yield and excellent e.r. (2n, 2o). This cyclization chemistry can also operate in tandem with other synthetic operations, permitting a one-pot ternary catalytic transformation of allyl ether 3 to 2a via the intermediacy of an iridium hydride catalyst, in 55% yield with 87:13 e.r. (FIG. 4A). While isomerization proceeds at the reaction temperature, the cyclization was found to be slow; it is possible that the urea and CPA coordinate to the iridium catalyst at these temperatures, disrupting the critical H-bonding interactions and reducing reaction efficacy.

We recognized compound 2n as a potential precursor to coixspirolactam C (6)—a natural product isolated from adlay bran that demonstrates mild inhibitory activity against lung and colon cancer cell lines (IC50=30-50 μg/mL).[16] As THPI 2n exhibits all of the requisite carbon atoms of coixspirolactam C— and most of the desired connectivity— we envisioned a concise synthetic route to the product enabled by our cooperative methodology. Subjecting 2n (synthesized from tryptophol in 3 steps) to N-bromosuccinimide under acidic conditions furnished a 20:1 mixture of spirocycles 4 and 5 as single diastereomers.[22] Acylated spirocycle 4 was smoothly converted to the free spirooxindole (5) by application of lithium hydroxide in CH2Cl2/MeOH. X-ray analysis confirmed the desired relative stereochemistry of the molecule, and established the absolute stereochemistry of the intermediate (FIG. 4B). This heterocyclic substructure is also present in several bioactive products,[23] yet there are surprisingly few published methods to access these spirooxindole derivatives.[24] Studies to oxidize 2n directly to the natural product through C—H functionalization logic[25] required examination of multiple oxidation conditions. Ultimately, subjecting 5 to tert-butyl hydroperoxide and diacetoxyiodobenzene in nitromethane oxidized the substrate to the desired lactone (6, 46% yield)[26] which matched the spectra (NMR, HRMS) reported for the natural product, but with opposite optical rotation value ([α]D25-20.1° (c=0.074, MeOH) vs reported +5.9°), thus supporting the absolute stereochemical assignment of the natural product.[27] The overall route comprises the first synthesis of coixspirolactam C in only 6 steps and confirms the reported connectivity.[16a]

Figure 5:
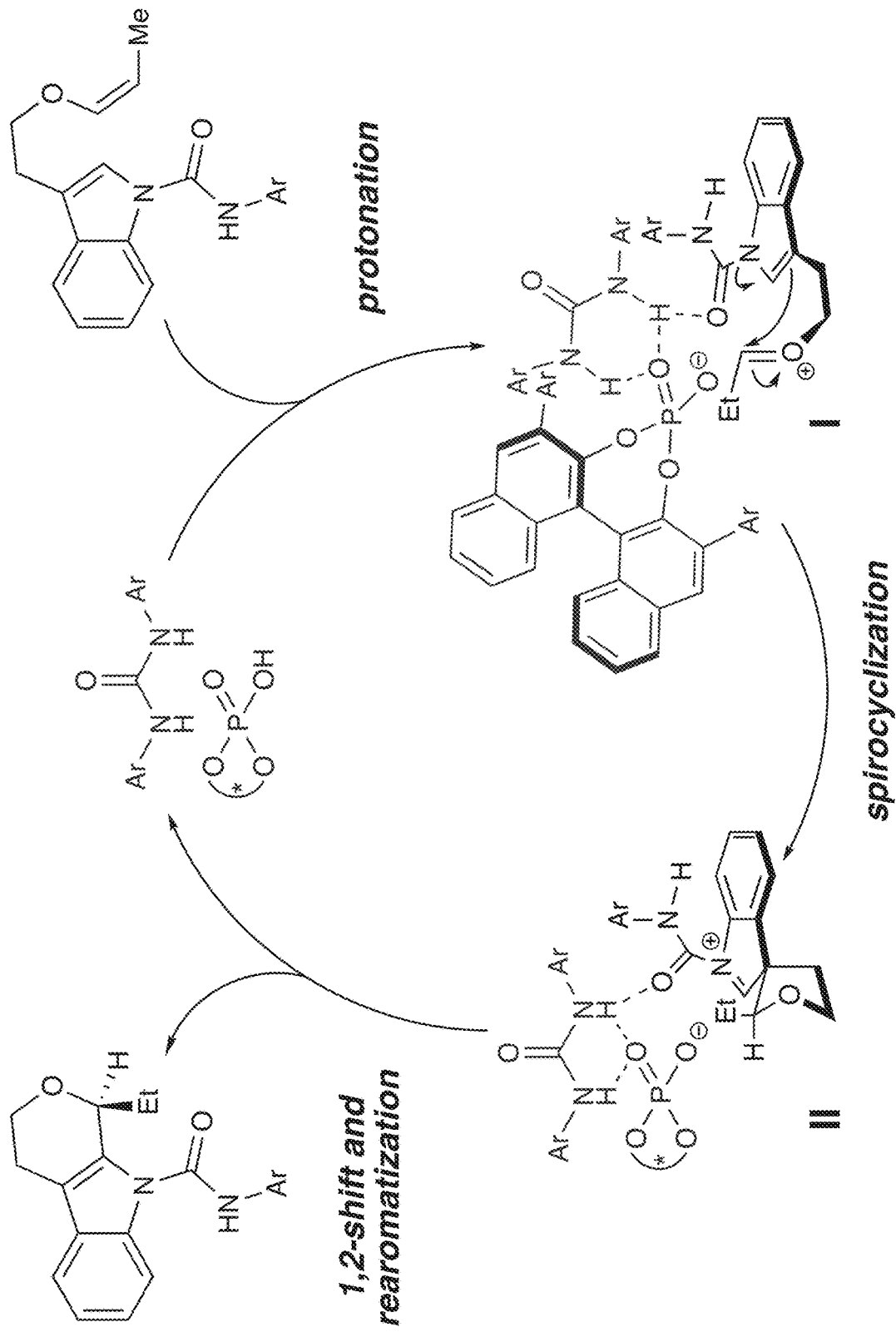
FIG. 5 is a schematic illustration of an exemplary catalytic cycle in accordance with some embodiments of the present disclosure.

As a result of our experimental observations that the inclusion of a hydrogen bonding urea provides dramatic enhancements to yield, selectivity, and rate, we propose the following reaction pathway (FIG. 5). The substrate recruits the urea and CPA by hydrogen bonding to form a proto-assembled complex. Subsequently, the CPA protonates the substrate enol ether, producing an oxocarbenium ion I that is rapidly trapped by the indole C3 position for form spirocyclic intermediate II.[28] Spirocyclic intermediate II undergoes a cationic 1,2-shift to produce the final connectivity through the indole C2 position. Deprotonation of the resulting tricycle restores aromaticity and furnishes the THPI product.

The CPA-urea co-catalyst system reported here provides both a greater reactivity and higher levels of selectivities for this transformation involving an oxocarbenium ion. The overall reaction provides access to a family of THPIs that can be further elaborated to achieve syntheses of members of a pharmacologically active family of spirooxindole natural products.[16b, 23] This reaction manifold represents a new application of cooperative catalysis, and holds potential for new and selective asymmetric transformation involving oxocarbenium ions.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

Materials/Methods

All reactions were carried out under an argon atmosphere in oven-dried glassware with magnetic stirring. Reagents were purified prior to use following the guidelines of Perrin and Armarego unless otherwise stated.i Purification of select reaction products was carried out by flash chromatography using a Biotage Isolera instrument (230-400 mesh silica). Analytical thin layer chromatography was performed on EM Reagent 0.25 mm silica gel 60-F plates. Visualization was accomplished with UV light and ceric ammonium nitrate stain, anisaldehyde stain, or potassium permanganate stain followed by heating. Infrared spectra were recorded on a Bruker Tensor 37 FTIR spectrometer and a Thermo Scientific Nicolet iS5 FTIR spectrometer. 1H-NMR spectra were recorded on a Bruker Avance 500 MHz with direct cryoprobe (500 MHz) spectrometer and an Agilent DD2 500 MHz spectrometer and are reported in ppm using solvent as an internal standard (CDCl3 at 7.26 ppm, CD3OD at 3.31 ppm, toluene-d8 at 2.08 ppm). Data are reported as (ap=apparent, s=singlet, d=doublet, t=triplet, q=quartet, m=multiplet, br=broad; coupling constant(s) in Hz; integration). Proton-decoupled 13C-NMR spectra were recorded on a Bruker Avance 500 MHz with direct cryoprobe (126 MHz) spectrometer and are reported in ppm using solvent as an internal standard (CDCl3 at 77.0 ppm, CD3OD at 49.0 ppm, toluene-d8 at 20.43 ppm). 31P-NMR spectra were recorded on an Agilent DD2 500 MHz spectrometer and are reported in ppm. Optical rotation data was obtained with an AUTOPOL VI polarimeter using the 589 nm sodium D line. Mass spectra data were obtained on a Varian 1200 Quadrupole Mass Spectrometer and Micromass Quadro II Spectrometer.

Indoles were purchased from commercial sources (MilliporeSigma/Sigma-Aldrich, Acros Organics, Fisher Scientific, Oakwood Chemical, Combi-Blocks, etc.) and used as received. Ethyl diazoacetate was purchased from Sigma-Aldrich, and used as received. Ethyl vinyl ether, stabilized with 0.1% KOH, was purchased from Sigma-Aldrich and used immediately as received. Allyl alcohol was dried over potassium carbonate and distilled prior to use. Trifluoromethanesulfonic acid was fractionally distilled from trifluoromethanesulfonic anhydride prior to use. Toluene was dried by passing through activated alumina and stored under dry argon prior to use. Deuterated solvents were purchased from Cambridge Isotope Laboratories (toluene-d8, methanol-d4, chloroform-d) and Sigma-Aldrich (toluene-d8); chloroform-d was stored over potassium carbonate, methanol-d4 and toluene-d8 were used as received. [(1,5-cyclooctadiene)(Ph2MeP)2Ir](PF6) was purchased from Alfa Aesar and stored and handled in a nitrogen glovebox. Chiral Brønsted acids and hydrogen bond donors were prepared in accordance with the literature.

General Procedure A: Synthesis of gem-Dimethyl Enol Ether Substrates[2,3]

(0.05 equiv). The resulting solution was cooled to 0° C., and ethyl diazoacetate (EDA, 1.1 equiv) as an 87% solution in dichloromethane was added dropwise (CAUTION: vigorous gas evolution). After addition was completed, the solution was permitted to warm to room temperature for one hour. The solvent was removed under partial pressure, and the residue was subjected to flash column chromatography to afford an inseparable mixture of C3-monoinsertion (desired, major) and C3,C2-diinsertion products (minor), which was used in the subsequent step without further purification.

To the round bottom flask containing the EDA insertion products was added THF (0.3 M), which was then cooled to 0° C. under an argon atmosphere. Methylmagnesium bromide (3.2 equiv) as a 3 M solution in ethyl ether was then slowly added with vigorous stirring due to the formation of precipitates. The ice bath was removed, and the reaction was permitted to warm to room temperature with monitoring by thin-layer silica chromatography (TLC). On completion, the reaction was quenched by the slow addition of saturated ammonium chloride solution, and extracted with ethyl acetate (2×100 mL). The collected organic layers were washed with 100 mL brine, dried over magnesium sulfate, filtered, and the solvent removed under partial pressure. The residue was subjected to flash column chromatography, yielding gem-dimethyl tertiary alcohols 6x.

To furnish the allyl ether 7x, the corresponding tertiary alcohol 6x (10 mmol, 1 equiv) was stirred in allyl alcohol (20 equiv) under an argon atmosphere. The solution was cooled to 0° C., and trifluoromethanesulfonic acid (1.2

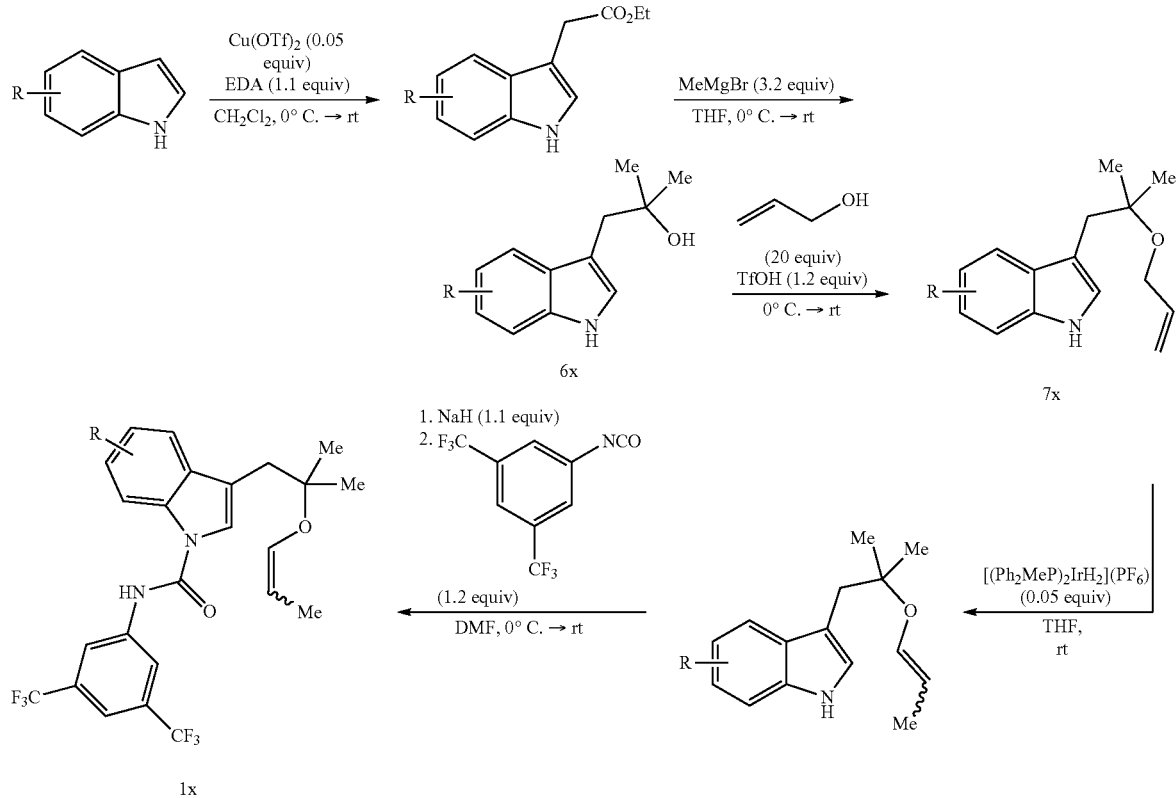

To a stirred solution of substituted indole (30 mmol, 1 equiv) in dichloromethane (0.5 M) under an argon atmosphere was added copper(II) trifluoromethanesulfonate equiv) was added dropwise, generating a rapid pale yellow to blood-red color change. The ice bath was removed, and the solution permitted to stir to room temperature until completed by TLC. On completion, the reaction was quenched by the slow addition of saturated sodium bicarbonate solution and extracted twice into ethyl acetate (2×100 mL). The collected organics were washed with 100 mL brine, dried over magnesium sulfate, filtered, and the solvent removed under partial pressure. The residue was subjected to flash column chromatography, yielding allyl ethers 7x.

A stirred solution of allyl ether 7x (1 equiv) was prepared in THF (0.17 M) under argon atmosphere. Iridium hydride precatalyst [(1,5-cyclooctadiene)(Ph2MeP)2Ir](PF6) (0.05 equiv) was suspended in THF (0.03M to 7x), and sparged wise, and the reaction was warmed to room temperature for one hour. The reaction was quenched by the dropwise addition of saturated ammonium chloride solution, and extracted thrice into ethyl acetate (3×100 mL). The collected organics were washed vigorously six times with 20× volumes of water and brine, dried over magnesium sulfate, filtered, and the solvent was removed under partial pressure. The residue was subjected to flash column chromatography to furnish gem-dimethyl indole carboxamide substrates 1x.

General Procedure B: Synthesis of Ethyl-Linker Enol Ether Substrates[3]

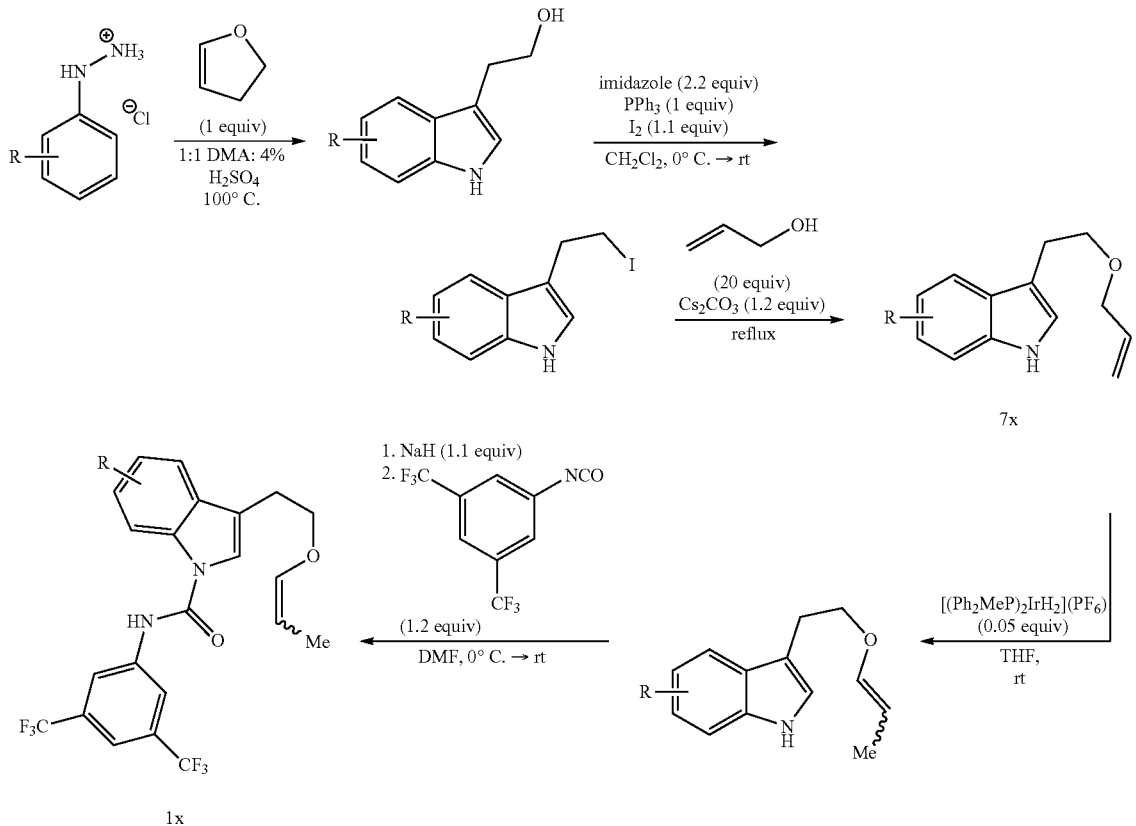

with H2; the red precatalyst dissolved to afford a pale yellow solution of activated catalyst (approx. 15 minutes). The catalyst solution was sparged with argon for 15 minutes, then transferred via syringe to the prepared solution of 7x. Isomerization of the allyl ether to enol ether was monitored by TLC/1H NMR (if Rfs were indistinguishable). On completion of the reaction, the reaction mixture was filtered through a plug of silica gel, and the solvent removed under partial pressure to yield the enol ether corresponding to 7x, which was used in the subsequent step without further purification.

A stirred solution of enol ether (5 mmol, 1 equiv) in DMF (0.5 M) under argon was cooled to 0° C. for 15 minutes. Sodium hydride (1.1 equiv) as a 60% dispersion in mineral oil was added portionwise to the solution (CAUTION: vigorous gas evolution), and the suspension was permitted to stir to room temperature for one hour. After one hour, the suspension had deepened substantially in color, and was cooled back to 0° C. Freshly-filtered 3,5-bis(trifluoromethyl)phenyl isocyanate (1.2 equiv) was then added drop- To a solution of phenyl hydrazine hydrochloride (50 mmol, 1 equiv) in 1:1 DMA:4% H2SO4 (0.5M) was added dihydrofuran (1 equiv). The resulting solution was heated to 100° C. for two hours or until the reaction was complete by TLC analysis. On completion, the solution was permitted to stir to room temperature, and then was extracted twice with ethyl acetate (2×100 mL). The collected organics were washed repeatedly with water and brine (5×400 mL), dried over magnesium sulfate, filtered, and concentrated under reduced pressure. The resulting tryptophols were used in the subsequent step without further purification.

To the round bottom flask containing the substituted tryptophol (1 equiv) was added dichloromethane (0.1 M), and at 0° C. imidazole (2.2 equiv), triphenylphosphine (1 equiv), and iodine (1.1 equiv). The resulting suspension was permitted to stir in the dark until the reaction was complete by TLC. The reaction was quenched by the addition of saturated sodium thiosulfate solution, and extracted twice with ethyl acetate. The collected organics were washed quickly with brine, dried over magnesium sulfate, filtered, and concentrated under reduced pressure before subjecting the residue to silica flash column chromatography to produce the primary iodide precursors to ethyl-linked allyl ethers 7x.

To produce ethyl-linked allyl ethers 7x, cesium carbonate (2 equiv) was added to a solution of the corresponding primary iodide (30 mmol, 1 equiv) in allyl alcohol (20 equiv). The suspension was heated to reflux until the reaction was complete by TLC. After completion, the reaction was cooled to room temperature, quenched by the slow addition of saturated ammonium chloride solution, and extracted twice into ethyl acetate (2×100 mL). The collected organics were washed with water and brine (2×100 mL), dried over magnesium sulfate, filtered, and concentrated under reduced pressure. Subjecting the residue to silica flash column chromatography furnished ethyl-linked allyl ethers 7x.

The ethyl-linked enol ether substrates 1x were produced from the corresponding ethyl-linked allyl ethers 7x via the same procedure as for the gem-dimethyl enol ether substrates (vide supra, General Procedure A); iridium hydride isomerization followed by aryl carboxamidization with sodium hydride and 1,5-bis(trifluoromethyl)phenyl isocyanate furnished the desired compounds.

General Procedure C: Synthesis of Ethyl-Linker Vinyl Ether Substrates[4]

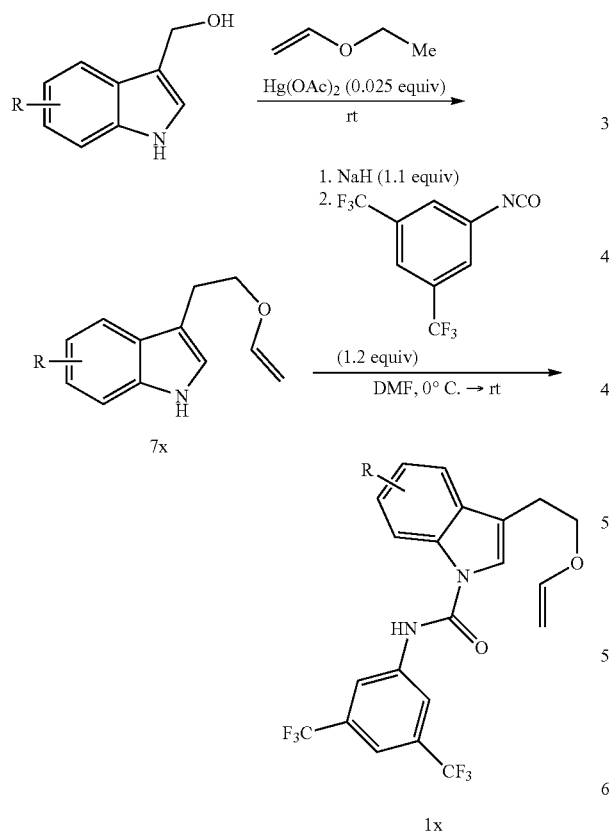

To a stirred suspension of substituted tryptophol (30 mmol, 1 equiv) in ethyl vinyl ether (1 M) was added mercury(II) acetate (0.025 equiv); the suspension homogenized, and was stirred at room temperature for 24 hours. The solvent was then removed under partial pressure, and the residue reconstituted in fresh ethyl vinyl ether (1 M). Another portion (0.025 equiv) of mercury(II) acetate was added, and the reaction was permitted to stir at room temperature for 24 hours with monitoring by TLC. On completion of the reaction, the reaction was quenched by the slow addition of triethylamine (0.1 equiv), and was partitioned between aqueous potassium carbonate and ether (200 mL). The organic layer was washed with brine (100 mL), dried over magnesium sulfate, and concentrated under reduced pressure. The residue was subjected to silica flash column chromatography to yield ethyl-linker vinyl ether indoles 7x.

The corresponding vinyl ether indole carboxamide substrates 1x were synthesized from the corresponding N—H vinyl ethers 7x via the same carboxamidization conditions as for the gem-dimethyl enol ether substrates and the ethyl-linker enol ether substrates (vide supra, General Procedure A).

Procedure for Synthesis of 1j[5]

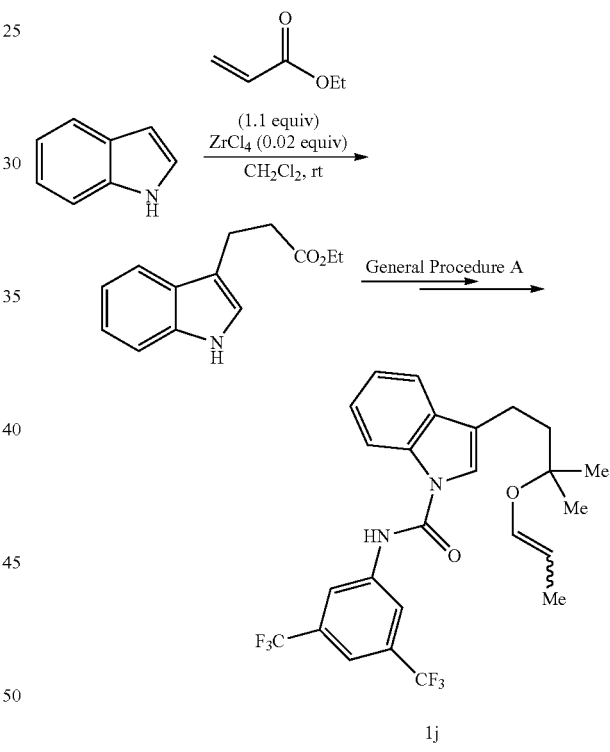

To a stirred solution of indole (50 mmol, 1 equiv) and ethyl acrylate (1.1 equiv) in dichloromethane (0.5 M) was added zirconium(IV) chloride (0.02 equiv). The solution was permitted to stir at room temperature with monitoring by TLC until complete. On completion, the reaction was partitioned with water and extracted twice into ethyl acetate (2×100 mL). The collected organics were washed with brine (100 mL), dried over sodium sulfate, filtered, and concentrated under reduced pressure. The residue was subjected to flash column chromatography to yield the ester precursor to 1j. The substrate was completed by subjecting this precursor to the subsequent steps of General Procedure A: Grignard addition, acid-mediated allylation, iridium hydride isomerization, and carboxamidization.

Procedure for Synthesis of 3

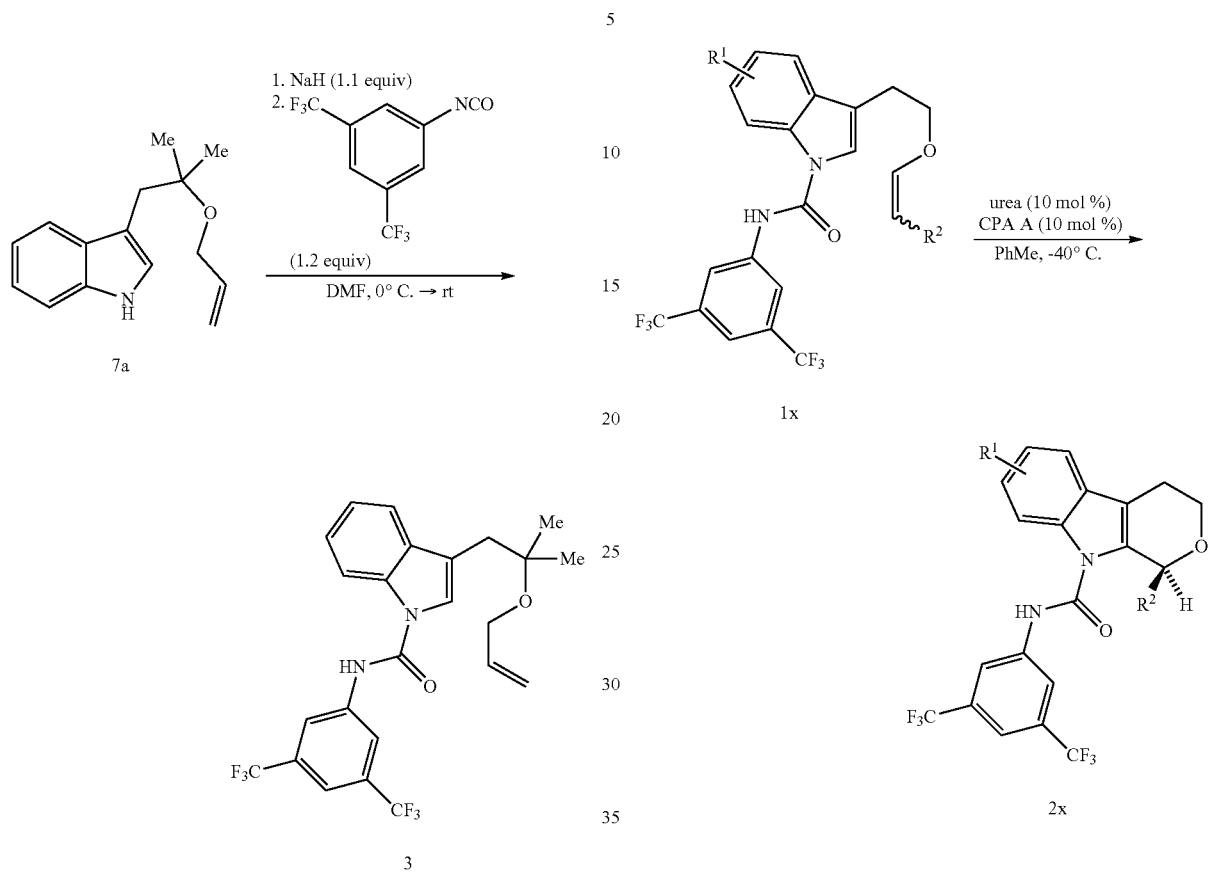

General Procedure D: Procedure for CPA/Urea-Catalyzed Cyclization

A stirred solution of allyl ether 7a (2 mmol, 1 equiv) in DMF (0.5 M) under argon was cooled to 0° C. for 15 minutes. Sodium hydride (1.1 equiv) as a 60% dispersion in mineral oil was added portionwise to the solution (CAUTION: vigorous gas evolution), and the suspension was permitted to stir to room temperature for one hour. After one hour, the suspension had deepened substantially in color, and was cooled back to 0° C. Freshly-filtered 3,5-bis(trifluoromethyl)phenyl isocyanate (1.2 equiv) was then added dropwise, and the reaction was warmed back to room temperature for one hour. The reaction was quenched by the dropwise addition of saturated ammonium chloride solution, and extracted thrice into ethyl acetate (3×100 mL). The collected organics were washed vigorously with water (5×500 mL) and brine (100 mL), dried over magnesium sulfate, filtered, and the solvent was removed under partial pressure. The residue was subjected to flash column chromatography to furnish allyl gem-dimethyl indole carboxamide substrate 3.

To an oven-dried reaction tube equipped with stirbar was added indole carboxamide substrate 1x (0.04 mmol, double azeotroped from toluene), 3,5-bis(trifluoromethylphenyl) urea (urea, 10 mol %), and dry toluene (1.5 mL). The tube was sealed, and cooled to −40° C. (unless otherwise noted). A solution of CPA (10 mol %) in dry toluene (0.5 mL) was prepared, and added to the reaction tube containing 1x and the suspended urea. The solution rapidly homogenized, and was left to stir at −40° C. until complete by TLC (15 min to 2 hours); a pale yellow coloring was observed for most solutions at or near completion. On completion, the solvent was removed under partial pressure, and the residue subjected to silica flash column chromatography to yield enantioenriched pyranoindoles 2x.

Procedure for Spirocyclization

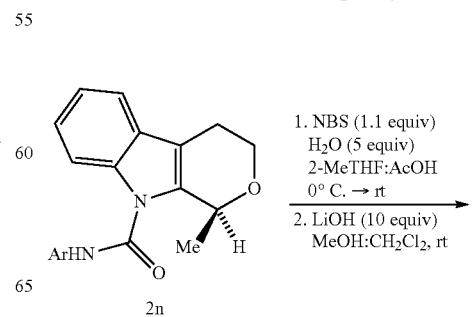

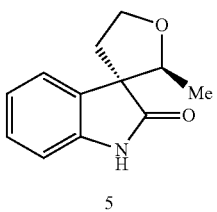

To a stirred solution of 2n (0.3 mmol, 0.05 M) in 6:1 2-Me THF:AcOH was added H2O (5 equiv) in darkness. The resulting solution was cooled to 0° C., and recrystallized N-bromosuccinimide (1.25 equiv) was added in a single portion, and the slowly-homogenizing suspension was permitted to stir to room temperature for 18 hours. After the reaction was complete by TLC, the solution was quenched by the dropwise addition of saturated sodium bicarbonate. The biphasic mixture was extracted with ethyl acetate (3×50 mL), and the collected organics were washed with brine (20 mL), dried over magnesium sulfate, filtered, and concentrated under reduced pressure. The resulting residue was subjected to flash column chromatography to yield the N-carboxamide spirocycle 4. Crystals suitable for X-ray diffraction were grown by slow diffusion of dichloromethane and hexanes.

The resulting N-carboxamide spirocycle 4 (0.05M) was dissolved in 1:1 MeOH:CH2Cl2, and lithium hydroxide (10 equiv) was added. On completion of the reaction by TLC, the solution was quenched by the slow dropwise addition of saturated ammonium chloride; the resulting biphasic mixture was extracted with ethyl acetate, and the collected organics were dried over magnesium chloride and the solvent removed under partial pressure. The residue was subjected to flash column chromatography to yield N—H spirocycle 5.

Procedure for Oxidation[6]

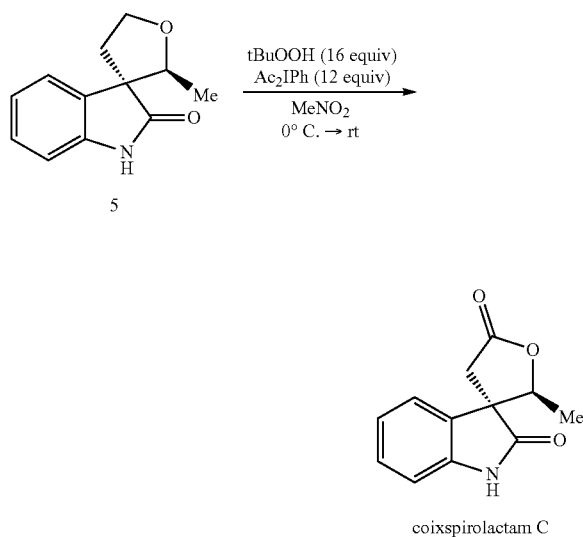

To a stirred solution of 5 in nitromethane (0.18 mmol, 0.05 M) was added diacetoxyiodobenzene (12 equiv). The resulting suspension was cooled to 0° C., and tert-butyl hydroperoxide (5.5 M in decane; 16 equiv) was added dropwise over 30 minutes. On completion of addition, the cooling bath was removed and the yellow homogenous solution was permitted to stir to room temperature for 18 hours. The reaction was then quenched by the addition of saturated aqueous sodium sulfite, extracted into ethyl acetate, and washed with brine (3×50 mL). The collected organics were then dried over magnesium sulfate, filtered, and concentrated under partial pressure to yield crude yellow oil. The oil was subjected to flash column chromatography to furnish coixspirolactam C in 46% yield.

Procedure for Ternary Catalyst Cyclization Cascade

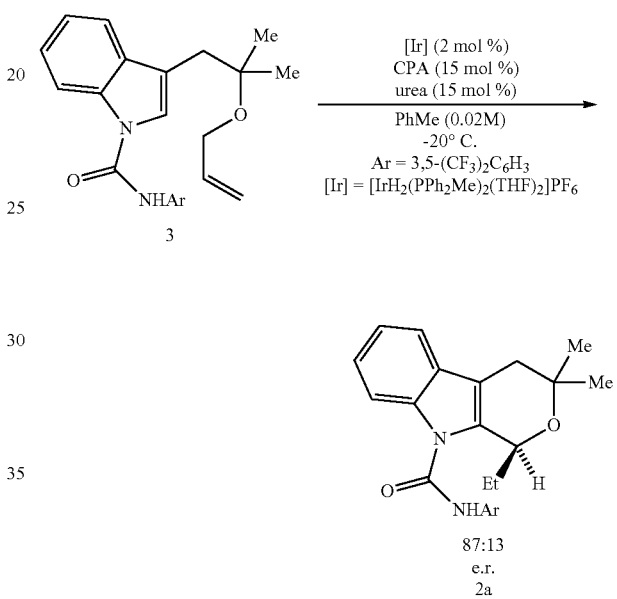

A stirred solution of allyl ether 3 (0.04 mmol), CPA (15 mol %), and urea (15 mol %) was prepared in toluene (0.02 M) at −20° C. under argon atmosphere. Iridium hydride precatalyst [(1,5-cyclooctadiene)(Ph2MeP)2Ir](PF6) (2 mol %) was suspended in THF and sparged with H2; the red precatalyst dissolved to afford a pale yellow solution of activated catalyst (approx. 15 minutes). The catalyst solution was sparged with argon for 15 minutes, then transferred via syringe to the prepared solution of 3. Isomerization of the allyl ether to enol ether, and subsequent cyclization to the THPI, was monitored by TLC. On completion of the reaction, the reaction was filtered through a plug of silica gel, and the solvent removed under partial pressure to yield 2a (55%, 87:13 e.r.). No reaction was observed prior to the addition of activated iridium hydride catalyst.

Figure 6:
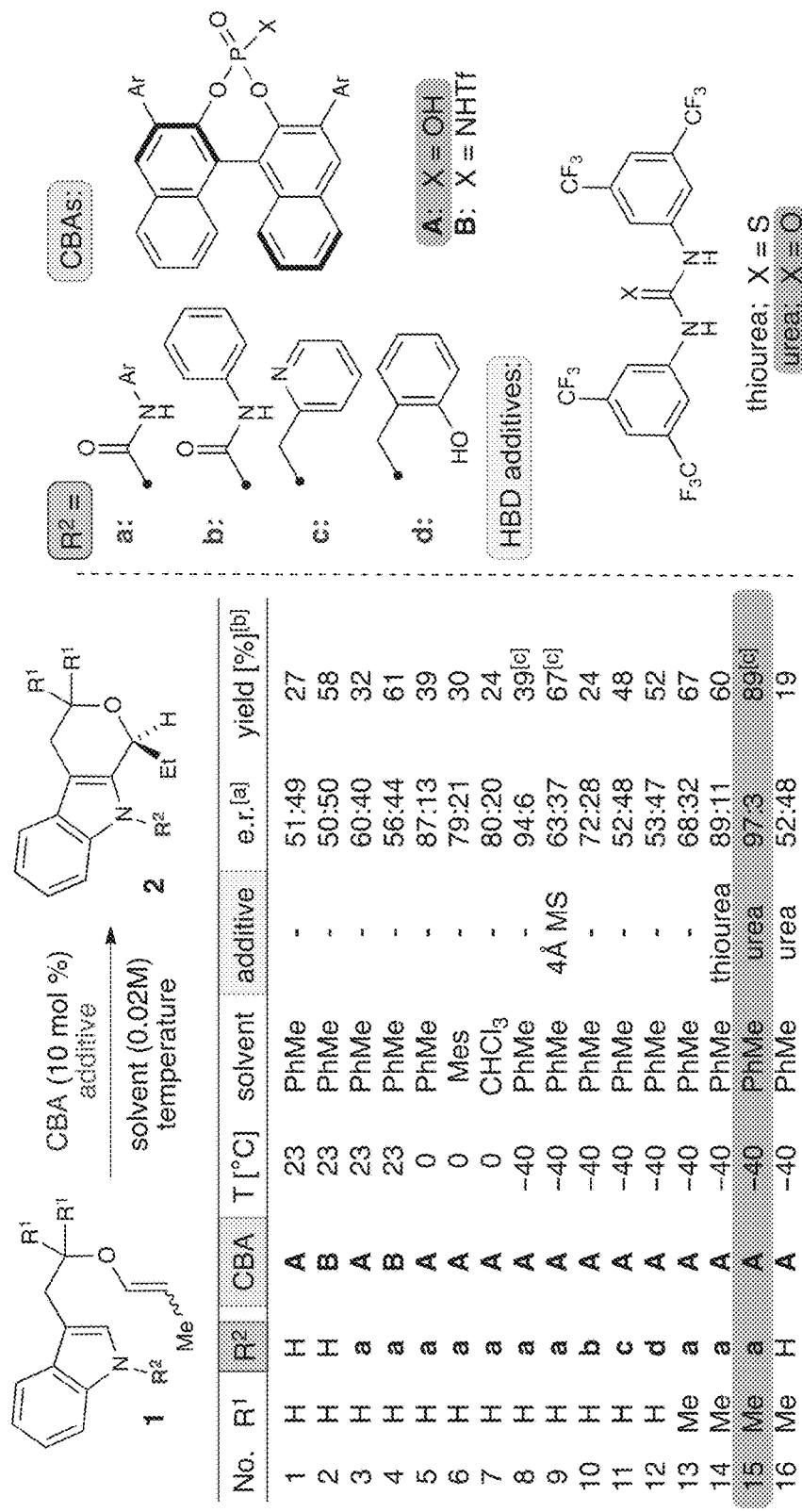
FIG. 6 is a schematic illustration of an exemplary reaction pathway and example tetrahydropyranoindole compounds in accordance with some embodiments of the present disclosure.

FIG. 6 illustrates selected optimization data. Selected reaction optimization experiments. [a] e.r. determined by chiral SFC or HPLC. [b] yield determined by NMR using trimethoxybenzene as an internal standard unless noted. [c] isolated yield.

FIG. 7 illustrates selected hydrogen bond donor optimization data.

Tabulated Spectral Data

Tertiary Alcohols (6)

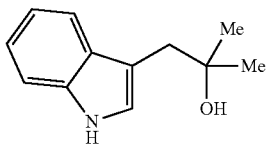

6a 1-(1H-indol-3-yl)-2-methylpropan-2-ol (6a). Prepared according to General Procedure A from indole, isolated as an off-white solid (2.8 g, 50% over two steps). Analytical data for 6a: 1H NMR (500 MHz, CDCl$_3$) δ 8.16 (s, 1H), 7.66 (dd, J=7.9, 1.2 Hz, 1H), 7.38 (dd, J=8.1, 1.0 Hz, 1H), 7.21 (ddd, J=8.2, 7.0, 1.2 Hz, 1H), 7.14 (ddd, J=8.0, 7.0, 1.1 Hz, 1H), 7.08 (d, J=2.3 Hz, 1H), 2.94 (s, 2H), 1.68 (s, 1H), 1.30 (s, 6H). 13C NMR (126 MHz, CDCl3) δ 134.7, 130.2, 124.9, 124.6, 122.1, 112.9, 112.5, 111.9, 70.9, 38.9, 29.2. FTIR (ATR) cm−1 3496, 3300, 3279, 3253, 3050, 2971, 1664, 1615, 1455, 1424, 1376, 1357, 1343, 1321, 1259, 1236, 1214, 1153, 1113, 1007, 967, 907, 777, 758. HRMS (ESI): Mass calculated for C12H15NNaO [M+Na]+: 212.1046; found 212.1047.

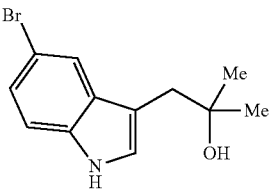

6b 1-(5-bromo-1H-indol-3-yl)-2-methylpropan-2-ol (6b). Prepared according to General Procedure A from 5-bromoindole, isolated as an off-white solid (3.6 g, 46% over two steps). Analytical data for 6b: 1H NMR (500 MHz, CDCl3) δ 8.17 (s, 1H), 7.76 (s, 1H), 7.27 (dd, J=9.0, 2.2 Hz, 1H), 7.24 (dd, J=8.6 Hz, 1H), 7.09 (d, J=2.3 Hz, 1H), 2.87 (s, 2H), 1.56 (s, 1H), 1.28 (s, 6H). 13C NMR (126 MHz, CDCl3) δ 134.7, 130.2, 124.9, 124.6, 122.1, 112.9, 112.5, 111.9, 70.9, 38.9, 29.2. FTIR (ATR) cm-1 3548, 3300, 3250, 3212, 2970, 2901, 1649, 1563, 1470, 1450, 1383, 1353, 1295, 1232, 1210, 1130, 1108, 965, 900, 889, 877, 793, 768, 659, 610. HRMS (ESI): Mass calculated for C12H14BrNNaO [M+Na]+: 290.0151; found 290.0154.

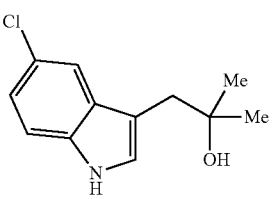

6c 1-(5-chloro-1H-indol-3-yl)-2-methylpropan-2-ol (6c). Prepared according to General Procedure A from 5-chlorindole, isolated as a white solid (2.3 g, 35% over two steps). Analytical data for 6c: 1H NMR (500 MHz, CDCl$_3$) δ 8.14 (s, 1H), 7.61 (d, J=2.0 Hz, 1H), 7.28 (d, J=8.6 Hz, 1H), 7.15 (dd, J=8.6, 2.0 Hz, 1H), 7.11 (d, J=2.4 Hz, 1H), 2.88 (s, 2H), 1.55 (s, 1H), 1.28 (s, 6H). 13C NMR (126 MHz, CDCl3) δ 134.4, 129.5, 125.4, 124.8, 122.3, 119.0, 112.0, 112.0, 70.9, 38.9, 29.2. FTIR (ATR) cm-1 3540, 3303, 3212, 2977, 2901, 1648, 1567, 1469, 1452, 183, 1372, 1295, 1231, 1208, 1138, 1129, 1108, 966, 895, 858, 794, 726, 768, 673, 618. Mass calculated for C12H14CNNaO [M+Na]+: 246.0662; found 246.0665.

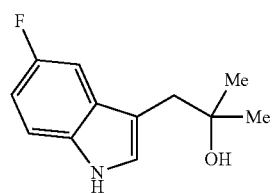

6d 1-(5-fluoro-1H-indol-3-yl)-2-methylpropan-2-ol (6d). Prepared according to General Procedure A from 5-fluoroindole, isolated as an off-white solid (2.5 g, 41% over two steps). Analytical data for 6d: 1H NMR (500 MHz, CDCl3) δ 8.30 (s, 1H), 7.29 (dd, J=7.8, 2.1 Hz, 1H), 7.27 (d, J=4.6 Hz, 1H), 7.11 (d, J=2.4 Hz, 1H), 6.95 (ddd, J=9.0, 9.0, 2.5 Hz, 1H), 2.89 (s, 2H), 1.72 (s, 1H), 1.30 (s, 6H). 13C NMR (126 MHz, CDCl3) δ 157.9 (d, JC-F=234.4 Hz), 132.6, 128.8 (d, J=9.6 Hz), 125.3, 112.1 (d, JC-F=4.7 Hz), 111.7 (d, JC-F=9.7 Hz), 110.4 (d, JC-F=26.4 Hz), 104.4 (d, JC-F=23.5 Hz), 71.1, 39.1, 29.2. FTIR (ATR) cm−1 3504, 3274, 2979, 1626, 1582, 1485, 1454, 1346, 1250, 1233, 1209, 1176, 1110, 1047, 968, 938, 903, 886, 652, 803, 771, 715, 634. HRMS (ESI): Mass calculated for C12H14FNNaO [M+Na]+: 230.0952; found 230.0956.

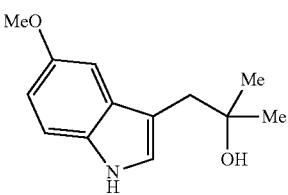

6e 1-(5-methoxy-1H-indol-3-yl)-2-methylpropan-2-ol (6e). Prepared according to General Procedure A from 5-methoxyindole, isolated as an off-white solid (2.8 g, 44% over two steps). Analytical data for 6e: 1H NMR (500 MHz, CDCl3) δ 8.52 (s, 1H), 7.23 (d, J=8.8 Hz, 1H), 7.14 (d, J=2.4 Hz, 1H), 7.00 (d, J=2.4 Hz, 1H), 6.90 (dd, J=8.7, 2.4 Hz, 1H), 3.88 (s, 3H), 2.93 (s, 2H), 2.03 (s, 1H), 1.33 (s, 6H). 13C NMR (126 MHz, CDCl3) δ 154.0, 131.5, 128.8, 124.7, 112.1, 112.0, 111.3, 101.4, 71.5, 56.0, 39.2, 29.2. FTIR (ATR) cm−1 3420, 2968, 2901, 2836, 1723, 1626, 1550, 1500, 1456, 1373, 1346, 1304, 1244, 1197, 1154, 1026, 902, 801, 764. HRMS (ESI): Mass calculated for C13H18NO2 [M+H]+: 220.1332; found 220.1332.

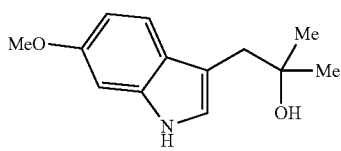

1-(6-methoxy-1H-indol-3-yl)-2-methylpropan-2-ol (6f). Prepared according to General Procedure A from 6-methoxyindole, isolated as an off-white solid (2.1 g, 32% over two steps). Analytical data for 6f: 1H NMR (500 MHz, CDCl3) δ 8.06 (s, 1H), 7.50 (d, J=8.7 Hz, 1H), 6.95 (d, J=2.2 Hz, 1H), 6.85 (d, J=2.2 Hz, 1H), 6.81 (dd, J=8.7, 2.3 Hz, 1H), 3.85 (s, 3H), 2.89 (s, 2H), 1.72 (s, 1H), 1.28 (s, 6H). 13C NMR (126 MHz, CDCl$_3$) δ 156.5, 136.9, 122.8, 122.1, 120.2, 111.9, 109.6, 94.4, 70.8, 55.6, 39.1, 29.2. FTIR (ATR) cm−1 3437, 3344, 2980, 2969, 2888, 1623, 1579, 1545, 1502, 1452, 1414, 1374, 1343, 1303, 1237, 1199, 1158, 1133, 1090, 1018, 974, 941, 912, 877, 800, 763. HRMS (ESI): Mass calculated for C13H18NO2 [M+H]+: 220.1332; found 220.1335.

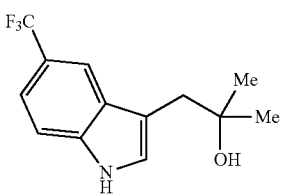

1-(5-trifluoromethyl-1H-indol-3-yl)-2-methylpropan-2-ol (6g). Prepared according to General Procedure A, isolated as an off-white solid (1.7 g, 23% over two steps). Analytical data for 6g: 1H NMR (500 MHz, CDCl3) δ 8.41 (s, 1H), 8.00 (s, 1H), 7.50 (s, 1H), 7.30 (d, J=32.3 Hz, 1H), 3.01 (s, 2H), 1.65 (bs, 1H), 1.36 (s, 6H). 13C NMR (126 MHz, CDCl3) δ 137.4, 127.8, 126.4 (q, JC-F=271.0 Hz), 125.0, 122.1 (q, JC-F=32.1 Hz), 118.7 (q, JC-F=3.5 Hz), 117.3 (q, JC-F=4.4 Hz), 113.2, 111.3, 71.0, 38.8, 29.2. FTIR (ATR) cm−1 3392, 2971, 2918, 2850, 1328, 1260, 1159, 1111, 1069, 1044, 905, 891, 808, 668, 649. HRMS (ESI): Mass calculated for C13H14F3NNaO [M+Na]+: 280.0920; found 280.0926.

6h

1-(7-methyl-1H-indol-3-yl)-2-methylpropan-2-ol (6h). Prepared according to General Procedure A from 7-methylindole, isolated as an off-white solid (1.9 g, 32% over two steps). Analytical data for 6h: 1H NMR (500 MHz, CDCl3) δ 8.22 (s, 1H), 7.54 (d, J=7.9 Hz, 1H), 7.11 (t, J=7.5 Hz, 1H), 7.06 (d, J=2.8 Hz, 1H), 7.04 (d, J=7.2 Hz, 1H), 2.97 (s, 2H), 2.51 (s, 3H), 1.84 (s, 1H), 1.33 (s, 6H). 13C NMR (126 MHz, CDCl3) δ 135.8, 128.0, 123.4, 122.5, 120.3, 119.8, 117.3, 112.3, 71.1, 39.3, 29.2, 16.6. FTIR (ATR) cm−1 3541, 3239, 2980, 1653, 1615, 1495, 1449, 1374, 1346, 1312, 1236, 1153, 1134, 1111, 1079, 988, 900, 828, 787, 771, 753, 732, 630. HRMS (ESI): Mass calculated for C13H17NNaO [M+Na]+: 226.1202; found 226.1205.

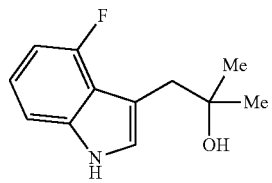

1-(4-fluoro-1H-indol-3-yl)-2-methylpropan-2-ol (6i). Prepared according to General Procedure A from 4-fluoroindole, isolated as an off-white solid (3.4 g, 56% over two steps). Analytical data for 6i: 1H NMR (500 MHz, CDCl3) δ 8.41 (s, 1H), 7.12 (d, J=8.1 Hz, 1H), 7.08 (ddd, J=8.0, 7.9, 4.9 Hz, 1H), 6.99 (d, J=2.4 Hz, 1H), 6.75 (ddd, J=11.6, 7.6, 1.0 Hz, 1H), 3.04 (s, 2H), 1.78 (s, 1H), 1.29 (s, 6H). 13C NMR (126 MHz, CDCl3) δ 157.2 (d, JC-F=246.1 Hz), 138.9 (d, JC-F=11.4 Hz), 123.5, 122.4 (d, JC-F=8.1 Hz), 117.2 (d, JC-F=18.6 Hz), 110.2 (d, JC-F=3.0 Hz), 107.3 (d, JC-F=3.6 Hz), 104.8 (d, JC-F=20.0 Hz), 71.0, 39.7 (d, JC-F=2.2 Hz), 28.8. FTIR (ATR) cm−1 3542, 3252, 3239, 2980, 2884, 1629, 1579, 1504, 1446, 1374, 1348, 1227, 1152, 1134, 1111, 1078, 1034, 900, 786, 751, 729, 629. HRMS (ESI): Mass calculated for C12H14FNNaO [M+Na]+: 230.0952; found 230.0951.

6j

1-(1H-indol-3-yl)-2-methylbutan-2-ol (6j). Prepared according to above procedure for the synthesis of 1j/General Procedure A from indole, isolated as an off-white solid (3.0 g, 50% over two steps). Analytical data for 6j: 1H NMR (500 MHz, CDCl$_3$) δ 8.22 (s, 1H), 7.89 (d, J=7.9 Hz, 1H), 7.61 (ddd, J=8.2, 0.9, 0.9 Hz, 1H), 7.46 (ddd, J=8.2, 7.0, 1.2 Hz, 1H), 7.39 (ddd, J=8.0, 6.9, 1.1 Hz, 1H), 7.26-7.23 (m, 1H), 3.24-3.04 (m, 2H), 2.26-2.13 (m, 2H), 1.67 (s, 1H), 1.61 (s, 6H). 13C NMR (126 MHz, CDCl3) δ 136.4, 127.4, 122.0, 120.8, 119.1, 118.8, 116.6, 111.1, 71.1, 44.0, 29.3, 20.0. FTIR (ATR) cm−1 3526, 3244, 2963, 2908, 2851, 1678, 1491, 1455, 1435, 1388, 1374, 1354, 1340, 1251, 1234, 1145, 1102, 1066, 1009, 981, 901, 796, 739, 623, 584. HRMS (ESI): Mass calculated for C13H17NNaO [M+Na]+: 226.1202; found 226.1203.

Allyl Ethers (7)

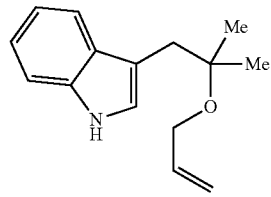

7a 3-(2-(allyloxy)-2-methylpropyl)-1H-indole (7a). Prepared according to General Procedure A from 6a, isolated as a pale yellow solid (2.1 g, 96%). Analytical data for 7a: 1H NMR (500 MHz, CDCl$_3$) δ 8.06 (s, 1H), 7.67 (d, J=7.8 Hz, 1H), 7.46-7.27 (m, 1H), 7.25-7.18 (m, 1H), 7.16 (ddd, J=8.0, 7.0, 1.1 Hz, 1H), 6.03 (ddt, J=17.1, 10.6, 5.4 Hz, 1H), 5.36 (dd, J=17.1, 1.8 Hz, 1H), 5.19 (dd, J=10.3, 1.7 Hz, 1H), 4.08 (dt, J=5.4, 1.5 Hz, 2H), 3.01 (s, 2H), 1.28 (s, 6H). 13C NMR (126 MHz, CDCl3) δ 136.2, 135.8, 128.6, 123.4, 121.6, 119.3, 119.2, 115.7, 112.4, 111.0, 76.3, 63.1, 36.0, 25.5. FTIR (ATR) cm-1 3414, 3307, 3055, 2971, 2915, 1645, 1617, 1489, 1455, 1421, 1381, 1363, 1339, 1273, 1221, 1132, 1117, 1094, 1010, 991, 919, 865, 818, 737. HRMS (ESI): Mass calculated for C15H19NNaO [M+Na]+: 252.1359; found 252.1352.

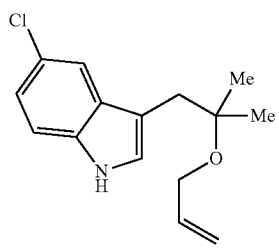

7c 3-(2-(allyloxy)-2-methylpropyl)-5-chloro-1H-indole (7c). Prepared according to General Procedure A from 6c, isolated as a viscous yellow oil (1.1 g, 45%). Analytical data for 7c: 1H NMR (500 MHz, CDCl$_3$) δ 8.21 (s, 1H), 7.64 (d, J=2.0 Hz, 1H), 7.20 (d, J=8.6 Hz, 1H), 7.13 (dd, J=8.6, 2.0 Hz, 1H), 7.05 (d, J=2.4 Hz, 1H), 6.01 (ddt, J=17.2, 10.6, 5.4 Hz, 1H), 5.35 (dq, J=17.1, 1.7 Hz, 1H), 5.19 (dq, J=10.4, 1.6 Hz, 1H), 4.06 (dt, J=5.5, 1.6 Hz, 2H), 2.93 (s, 2H), 1.26 (s, 5H). 13C NMR (126 MHz, CDCl3) δ 136.0, 134.1, 129.7, 124.9, 124.9, 121.8, 118.9, 116.0, 112.1, 112.0, 76.1, 63.1, 36.0, 25.4. FTIR (ATR) cm-1 3420, 3280, 2971, 2915, 1645, 1568, 1461, 1421, 1364, 1316, 1259, 1220, 1171, 1138, 1124, 1095, 1042, 991, 921, 892, 862, 793, 761, 678, 612, 586. HRMS (ESI): Mass calculated for C15H18ClNNaO [M+Na]+: 286.0969; found 286.0974.

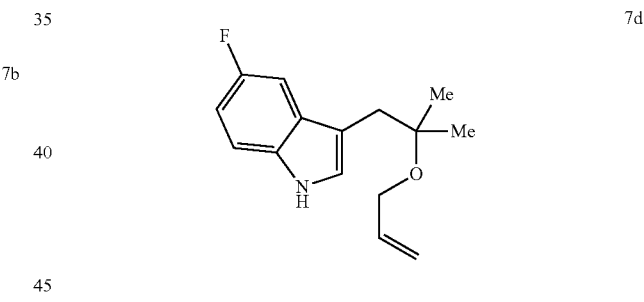

3-(2-(allyloxy)-2-methylpropyl)-5-bromo-1H-indole (7b). Prepared according to General Procedure A from 6b, isolated as a viscous yellow oil (2.0 g, 66%). Analytical data for 7b: 1H NMR (500 MHz, CDCl$_3$) δ 8.22 (s, 1H), 7.84 (d, J=1.9 Hz, 1H), 7.31 (dd, J=8.6, 1.9 Hz, 1H), 7.23 (d, J=8.6 Hz, 1H), 7.11 (d, J=2.4 Hz, 1H), 6.05 (ddt, J=17.3, 10.5, 5.3 Hz, 1H), 5.40 (dq, J=17.1, 1.8 Hz, 1H), 5.24 (dq, J=10.3, 1.6 Hz, 1H), 4.10 (dt, J=5.5, 1.7 Hz, 2H), 2.98 (s, 2H), 1.30 (s, 6H). 13C NMR (126 MHz, CDCl3) δ 136.0, 134.4, 130.4, 124.7, 124.3, 122.0, 115.9, 112.5, 112.4, 112.1, 75.9, 63.1, 36.1, 25.4. FTIR (ATR) cm-1 3412, 3280, 2971, 2907, 1715, 1645, 1565, 1459, 1422, 1381, 1363, 1312, 1286, 1259, 1220, 1123, 1042, 991, 921, 881, 793, 761, 663, 606, 584. HRMS (ESI): Mass calculated for C15H18BrNNaO [M+Na]+: 330.0464; found 330.0458.

3-(2-(allyloxy)-2-methylpropyl)-5-fluoro-1H-indole (7d). Prepared according to General Procedure A from 6d, isolated as a pale yellow oil (1.3 g, 56%). Analytical data for 7d: 1H NMR (500 MHz, CDCl$_3$) δ 8.33 (s, 1H), 7.46 (dd, J=9.9, 2.5 Hz, 1H), 7.36 (dd, J=8.8, 4.4 Hz, 1H), 7.24 (d, J=2.4 Hz, 1H), 7.09 (td, J=9.0, 2.5 Hz, 1H), 6.17 (ddt, J=17.2, 10.5, 5.4 Hz, 1H), 5.51 (dq, J=17.2, 1.8 Hz, 1H), 5.34 (dq, J=10.4, 1.6 Hz, 1H), 4.22 (dt, J=5.5, 1.6 Hz, 2H), 3.09 (s, 2H), 1.42 (s, 6H). 13C NMR (126 MHz, CDCl3) δ 157.8 (d, JC-F=233.6 Hz), 136.1, 132.3, 129.0 (d, JC-F=9.5 Hz), 125.4, 115.9, 112.5 (d, JC-F=4.7 Hz), 111.6 (d, JC-F=9.6 Hz), 109.9 (d, JC-F=26.4 Hz), 104.2 (d, JC-F=23.3 Hz), 76.2, 63.1, 36.2, 25.4. FTIR (ATR) cm-1 3847, 3421, 3294, 2969, 2924, 2867, 1657, 1628, 1581, 1548, 1484, 1451, 1383, 1364, 1313, 1294, 1264, 1229, 1177, 1116, 1093, 1040, 993, 935, 848, 828, 794, 760, 718. HRMS (ESI): Mass calculated for C15H18FNNaO [M+Na]+: 270.1265; found 270.1269.

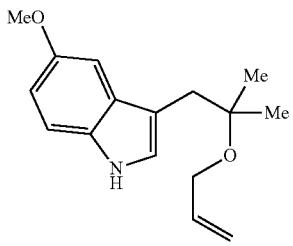

7e 3-(2-(allyloxy)-2-methylpropyl)-5-methoxy-1H-indole (7e). Prepared according to General Procedure A from 6e, isolated as an orange/brown viscous oil (1.0 g, 40%). Analytical data for 7e: 1H NMR (500 MHz, tol-d8) δ 7.20 (d, J=2.3 Hz, 1H), 7.00 (dd, J=8.7, 2.4 Hz, 1H), 6.93 (d, J=8.7 Hz, 1H), 6.70 (d, J=2.3 Hz, 1H), 5.97 (ddt, J=17.3, 10.1, 4.9 Hz, 1H), 5.36 (dq, J=17.1, 2.0 Hz, 1H), 5.10 (dt, J=10.5, 1.8 Hz, 1H), 3.88 (dt, J=5.0, 1.8 Hz, 2H), 3.64 (s, 3H), 2.92 (s, 2H), 1.18 (s, 6H). 13C NMR (126 MHz, tol-d8) δ 154.2, 136.7, 131.2, 129.2, 123.9, 114.2, 111.9, 111.8, 111.4, 101.2, 75.6, 62.6, 54.9, 36.7, 24.9. FTIR (ATR) cm−1 3412, 3309, 2971, 2929, 2833, 1678, 1622, 1564, 1552, 1471, 1439, 1362, 1327, 1273, 1209, 1171, 1068, 1051, 919, 885, 831, 796, 760, 741, 680, 634. HRMS (ESI): Mass calculated for C16H21NNaO2 [M+Na]+: 282.1465; found 282.1471.

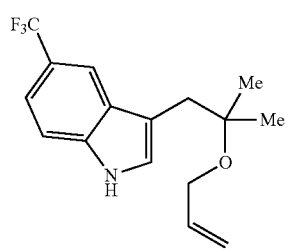

7f 3-(2-(allyloxy)-2-methylpropyl)-6-methoxy-1H-indole (7f). Prepared according to General Procedure A from 6f, isolated as a viscous yellow-orange oil (1.7 g, 66%). Analytical data for 7f: 1H NMR (500 MHz, CDCl3) δ 7.90 (s, 1H), 7.48 (d, J=8.6 Hz, 1H), 6.94 (d, J=2.2 Hz, 1H), 6.82 (d, J=2.2 Hz, 1H), 6.78 (dd, J=8.7, 2.3 Hz, 1H), 5.97 (ddt, J=17.1, 10.5, 5.4 Hz, 1H), 5.30 (dq, J=17.3, 1.8 Hz, 1H), 5.13 (dq, J=10.4, 1.6 Hz, 1H), 4.02 (dt, J=5.4, 1.6 Hz, 2H), 3.83 (s, 3H), 2.92 (s, 2H), 1.22 (s, 6H). 13C NMR (126 MHz, CDCl3) δ 156.2, 136.4, 136.2, 123.0, 122.1, 119.9, 115.7, 112.4, 109.1, 94.4, 76.1, 63.0, 55.6, 36.1, 25.4. FTIR (ATR) cm−1 3404, 3078, 2967, 2923, 2851, 1720, 1626, 1501, 1458, 1344, 1304, 1226, 1198, 1158, 1136, 1028, 920, 869, 800. HRMS (ESI): Mass calculated for C16H21NNaO2 [M+Na]+: 282.1465; found 282.1473.

7g 3-(2-(allyloxy)-2-methylpropyl)-5-trifluoromethyl-1H-indole (7g). Prepared according to General Procedure A from 6g, isolated as a pale yellow oil (1.3 g, 46%). Analytical data for 7g: 1H NMR (500 MHz, CDCl3) δ 8.11 (s, 1H), 7.81 (s, 1H), 7.28-7.21 (m, 2H), 7.02 (d, J=2.2 Hz, 1H), 5.82 (ddt, J=17.2, 10.5, 5.3 Hz, 1H), 5.15 (dq, J=17.3, 1.8 Hz, 1H), 5.00 (dq, J=10.3, 1.5 Hz, 1H), 3.87 (dt, J=5.4, 1.6 Hz, 2H), 2.83 (s, 2H), 1.09 (s, 6H). 13C NMR (126 MHz, CDCl3) δ 137.1, 136.0, 128.0, 125.5 (q, JC-F=271.6 Hz), 125.0, 121.6 (q, JC-F=31.7 Hz), 118.3 (q, JC-F=3.5 Hz), 117.3 (q, JC-F=4.4 Hz), 115.8, 113.5, 111.1, 75.8, 63.1, 36.2, 25.3. FTIR (ATR) cm−1 3297, 2979, 2909, 2869, 1880, 1629, 1446, 1368, 1333, 1323, 1293, 1260, 1234, 1210, 1184, 1158, 1132, 1101, 1070, 1042, 992, 936, 903, 891, 878, 837, 807, 777, 766, 754, 734, 662, 626. HRMS (ESI): Mass calculated for C16H18F3NNaO [M+Na]+: 320.1233; found 320.1238.

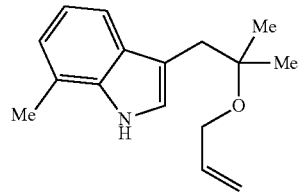

7h 3-(2-(allyloxy)-2-methylpropyl)-7-methyl-1H-indole (7h). Prepared according to General Procedure A from 6h, isolated as a pale yellow oil (1.6 g, 66%). Analytical data for 7h: 1H NMR (500 MHz, CDCl3) δ 7.96 (s, 1H), 7.11 (d, J=2.6 Hz, 1H), 7.08 (dd, J=7.7, 3.0 Hz, 1H), 7.02 (d, J=7.0 Hz, 1H), 6.02 (ddt, J=17.3, 10.5, 5.2 Hz, 1H), 5.36 (dq, J=17.2, 1.9 Hz, 1H), 5.18 (dq, J=10.4, 1.8 Hz, 1H), 4.07 (dt, J=5.3, 1.7 Hz, 2H), 3.01 (d, J=3.7 Hz, 2H), 2.51 (d, J=3.5 Hz, 3H), 1.28 (d, J=3.3 Hz, 6H). 13C NMR (126 MHz, CDCl3) δ 136.3, 135.3, 128.1, 123.1, 122.1, 120.0, 119.4, 117.1, 115.7, 112.9, 76.2, 63.0, 36.1, 25.4, 16.6. FTIR (ATR) cm−1 3413, 2956, 2923, 2865, 2161, 2051, 1722, 1603, 1582, 1460, 1380, 1364, 1304, 1240, 1200, 1163, 1032, 908, 860, 778, 741, 646. HRMS (ESI): Mass calculated for C16H21NNaO [M+Na]+: 266.1515; found 266.1522.

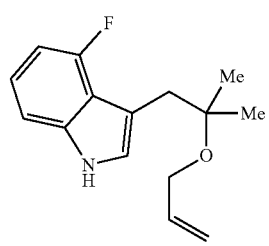

7i 3-(2-(allyloxy)-2-methylpropyl)-4-fluoro-1H-indole (7i). Prepared according to General Procedure A from 6i, isolated as a pale yellow-orange oil (1.6 g, 67%). Analytical data for 7i: 1H NMR (500 MHz, CDCl3) δ 8.42 (s, 1H), 7.29-7.18 (m, 2H), 7.18 (d, J=2.3 Hz, 1H), 6.91 (ddd, J=11.6, 7.5, 1.1 Hz, 1H), 6.15 (ddt, J=17.2, 10.5, 5.3 Hz, 1H), 5.49 (dq, J=17.2, 1.8 Hz, 1H), 5.32 (dq, J=10.4, 1.6 Hz, 1H), 4.22 (dt, J=5.4, 1.6 Hz, 2H), 3.29 (s, 2H), 1.42 (s, 6H). 13C NMR (126 MHz, CDCl3) δ 157.3 (d, JC-F=246.1 Hz), 138.4 (d, JC-F=11.6 Hz), 136.2, 123.7 (d, JC-F=1.5 Hz), 121.9 (d, JC-F=8.0 Hz), 117.3 (d, JC-F=18.5 Hz), 115.7, 110.6 (d, JC-F=3.0 Hz), 107.2 (d, JC-F=3.5 Hz), 104.5 (d, JC-F=20.0 Hz), 76.2, 62.9, 36.1 (d, JC-F=2.6 Hz), 25.2. FTIR (ATR) cm−1 3242, 2978, 2919, 2858, 1889, 1631, 1578, 1540, 1507, 1469, 1425, 1385, 1369, 1348, 1314, 1247, 1226, 1156, 1139, 1127, 1074, 1029, 999, 932, 864, 831, 821, 783, 749, 730, 668. HRMS (ESI): Mass calculated for C15H18FNNaO [M+Na]+: 270.1265; found 270.1270.

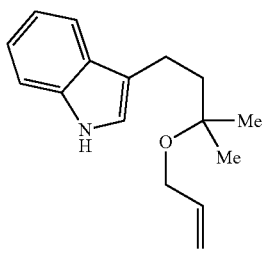

3-(2-(allyloxy)-2-methylbutyl)-5-fluoro-1H-indole (7j). Prepared according to above procedure for the synthesis of 1j/General Procedure A from 6j, isolated as a pale yellow oil (1.0 g, 44%). Analytical data for 7j: 1H NMR (500 MHz, CDCl3) δ 8.21 (s, 1H), 7.91 (d, J=7.6 Hz, 1H), 7.63 (d, J=8.1 Hz, 1H), 7.49 (dd, J=7.7, 7.7 Hz, 1H), 7.42 (dd, J=7.7, 7.7 Hz, 1H), 7.24 (d, J=2.5 Hz, 1H), 6.28 (ddt, J=17.1, 10.5, 5.3 Hz, 1H), 5.63 (dq, J=17.1, 1.8 Hz, 1H), 5.45 (dq, J=10.3, 1.6 Hz, 1H), 4.27 (dt, J=5.5, 1.7 Hz, 2H), 3.38-2.93 (m, 2H), 2.42-2.08 (m, 2H), 1.60 (s, 6H). 13C NMR (126 MHz, CDCl3) δ 136.4, 136.2, 127.5, 121.9, 120.8, 119.1, 118.9, 117.0, 115.8, 111.1, 75.0, 62.8, 40.5, 25.7, 19.5. FTIR (ATR) cm−1 3416, 3304, 3079, 3057, 3013, 2971, 2929, 2859, 1645, 1619, 1456, 1421, 1383, 1363, 1336, 1207, 1132, 1065, 1011, 994, 918, 885, 809, 737. HRMS (ESI): Mass calculated for C16H22NO [M+H]+: 244.1696; found 244.1699.

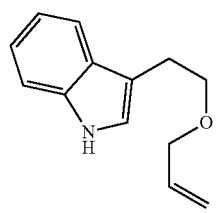

3-(2-(allyloxy)ethyl)-1H-indole (7k). Prepared according to general procedure B; analytical data matches previously published characterization data.ii

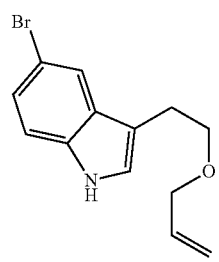

3-(2-(allyloxy)ethyl)-5-bromo-1H-indole (7l). Prepared according to General Procedure B, isolated as a viscous orange oil (0.50 g, 18% over 3 steps). Analytical data for 7l: 1H NMR (500 MHz, CDCl3) δ 7.77 (s, 1H), 7.26 (d, J=2.0 Hz, 1H), 6.75 (dd, J=8.6, 1.9 Hz, 1H), 6.58 (d, J=8.6 Hz, 1H), 6.42 (d, J=2.5 Hz, 1H), 5.46 (ddt, J=17.3, 10.4, 5.6 Hz, 1H), 4.83 (dq, J=17.2, 1.7 Hz, 1H), 4.72 (dq, J=10.4, 1.4 Hz, 1H), 3.55 (dt, J=5.7, 1.5 Hz, 2H), 3.24 (t, J=7.0 Hz, 2H), 2.51 (t, J=7.1 Hz, 2H). 13C NMR (126 MHz, CDCl3) δ 134.8, 134.7, 129.4, 124.6, 123.6, 121.4, 117.3, 112.7, 112.5, 112.4, 71.9, 70.4, 25.7. FTIR (ATR) cm−1 3424, 3282, 2910, 2855, 1721, 1643, 1566, 1459, 1421, 1347, 1276, 1247, 1225, 1080, 989, 927, 881, 862, 759, 717, 657, 604, 581. HRMS (ESI): Mass calculated for C13H13BrNO [M−H]−: 278.019; found 278.019.

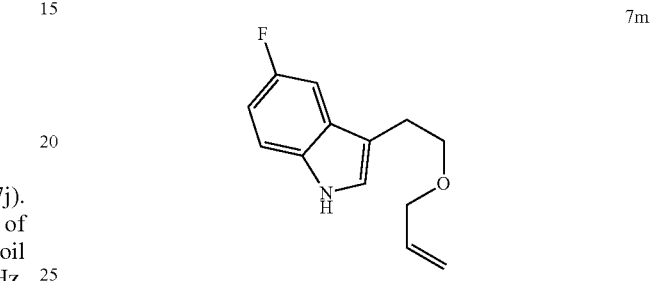

3-(2-(allyloxy)ethyl)-5-fluoro-1H-indole (7m). Prepared according to General Procedure B, isolated as a pale yellow oil (0.43 g, 20% over 3 steps). Analytical data for 7m: 1H NMR (500 MHz, CDCl3) δ 7.95 (s, 1H), 7.24 (dd, J=8.4, 4.3 Hz, 2H), 7.09 (d, J=2.4 Hz, 1H), 6.91 (td, J=9.1, 2.5 Hz, 1H), 5.92 (ddt, J=17.1, 10.5, 5.3 Hz, 1H), 5.27 (dq, J=17.3, 1.7 Hz, 1H), 5.16 (dq, J=10.4, 1.5 Hz, 1H), 4.01 (dt, J=5.7, 1.5 Hz, 2H), 3.70 (t, J=7.1 Hz, 2H), 2.99 (t, J=7.2 Hz, 2H). 13C NMR (126 MHz, CDCl3) δ 157.7 (d, JC-F=234.3 Hz), 134.8, 132.6, 128.0 (d, JC-F=9.5 Hz), 123.7, 116.9, 113.4 (d, JC-F=4.7 Hz), 111.6 (d, JC-F=9.8 Hz), 110.3 (d, JC-F=26.4 Hz), 103.8 (d, JC-F=23.4 Hz), 71.9, 70.3, 25.7. FTIR (ATR) cm−1 3468, 3422, 3317, 3081, 3012, 2908, 2861, 1646, 1583, 1486, 1457, 1426, 1348, 1297, 1243, 1171, 1090, 993, 934, 850, 795, 710, 668. HRMS (ESI): Mass calculated for C13H13FNO [M−H]−: 218.099; found 218.099.

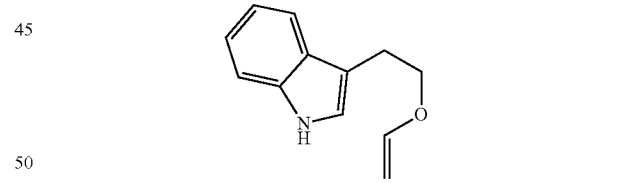

3-(2-(vinyloxy)ethyl)-1H-indole (7n). Prepared according to General Procedure C; analytical data matches previously published characterization data.iii

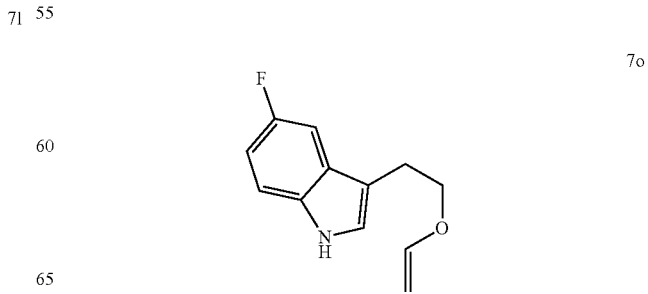

3-(2-(vinyloxy)ethyl)-5-fluoro-1H-indole (7o). Prepared according to General Procedure C, isolated as a pale yellow oil (4.0 g, 65%). Analytical data for 7o: 1H NMR (500 MHz, CD3OD) δ 10.23 (s, 1H), 7.27 (ddd, J=8.9, 4.5, 1.4 Hz, 2H), 7.21 (dd, J=9.9, 2.5 Hz, 2H), 7.10 (t, J=2.8 Hz, 2H), 6.86 (td, J=9.1, 2.5 Hz, 2H), 6.46 (ddd, J=14.5, 6.9, 2.0 Hz, 1H), 4.19 (dt, J=14.3, 1.6 Hz, 2H), 3.96 (dt, J=6.8, 1.4 Hz, 2H), 3.88 (td, J=7.0, 3.0 Hz, 3H), 3.00 (td, J=6.9, 2.8 Hz, 3H). 13C NMR (126 MHz, CD3OD) δ 157.4 (d, JC-F=232.0 Hz), 151.5, 133.3, 133.1, 127.8 (d, JC-F=9.7 Hz), 127.7 (d, JC-F=9.5 Hz), 124.5, 124.3, 111.6 (d, JC-F=2.2 Hz), 111.5 (d, JC-F=7.0 Hz), 108.9 (d, JC-F=26.7 Hz), 102.6 (dd, JC-F=23.4, 3.3 Hz), 86.4-84.7 (m), 68.1, 24.7. FTIR (ATR) cm−1 3420, 3420, 3117, 3060, 2924, 2874, 1617, 1582, 1484, 1453, 1320, 1291, 1228, 1193, 1170, 1120, 1060, 991, 931, 850, 821, 793, 758, 707, 673. HRMS (ESI): Mass calculated for C12H11FNO [M−H]−: 204.083; found 204.083.

Indole Carboxamide Substrates (1x)

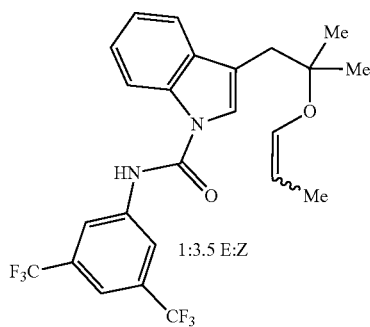

1a

1:3.5 E:Z

N-(3,5-bis(trifluoromethyl)phenyl)-3-(2-methyl-2-(prop-1-en-1-yloxy)propyl)-1H-indole-1-carboxamide (1a). Prepared according to General Procedure A, isolated as a white solid; E:Z ratio: 1:3.5 (1.6 g, 70% over two steps). Analytical data for 1a: major (Z): 1H NMR (500 MHz, tol-d8) δ 8.27 (d, J=8.2 Hz, 1H), 7.69 (s, 2H), 7.65 (s, 1H), 7.55 (s, 1H), 7.53-7.49 (m, 1H), 7.28 (t, J=7.1 Hz, 1H), 7.23 (t, J=7.5 Hz, 1H), 6.55 (s, 1H), 6.15 (dq, J=6.3, 1.8 Hz, 1H), 4.54 (p, J=6.7 Hz, 1H), 2.81 (s, 2H), 1.73 (dd, J=6.7, 1.7 Hz, 3H), 1.17 (s, 6H). minor (E): 1H NMR (500 MHz, tol-d8) δ 8.33 (d, J=8.1 Hz, 1H), 7.53 (d, J=1.1 Hz, 1H), 7.29 (t, J=8.1 Hz, 1H), 7.24 (t, J=7.5 Hz, 1H), 7.19 (s, 1H), 7.16 (s, 2H), 6.63 (s, 1H), 6.25 (dq, J=11.9, 1.6 Hz, 1H), 5.22 (dq, J=11.9, 6.8 Hz, 1H), 2.83 (s, 2H), 1.56 (dd, J=6.8, 1.6 Hz, 3H), 1.18 (s, 6H). 13C NMR (126 MHz, tol-d8) δ 148.4, 148.3, 146.5, 140.4, 139.3, 139.3, 139.2, 137.3, 136.8, 135.6, 135.4, 132.0 (q, JC-F=33.4 Hz), 131.9 (q, JC-F=33.3 Hz), 131.3, 131.3, 128.7, 127.8, 125.0, 122.7, 122.3, 122.2, 122.2, 119.7, 119.7, 119.4 (q, JC-F=3.3 Hz), 119.3 (q, JC-F=3.1 Hz), 117.5, 117.5, 116.8-116.6 (m), 115.0, 114.8, 104.2, 102.1, 77.1, 77.0, 36.1, 35.9, 25.5, 25.5, 20.6, 12.3, 9.5. FTIR (ATR) cm−1 3246, 2976, 2921, 1737, 1546, 1467, 1454, 1384, 1367, 1337, 1276, 1231, 1174, 1137, 1113, 1030, 1009, 996, 930, 908, 885, 746, 681, 625. HRMS (ESI): Mass calculated for C24H21F6N2O2 [M−H]−: 483.151; found 483.152.

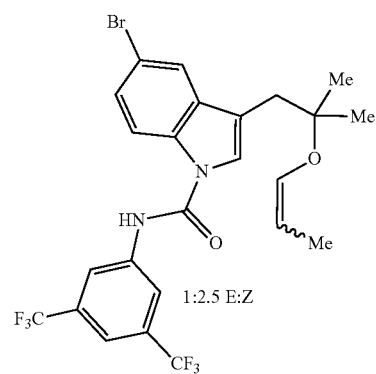

1b

1:2.5 E:Z

N-(3,5-bis(trifluoromethyl)phenyl)-5-bromo-3-(2-methyl-2-(prop-1-en-1-yloxy)propyl)-1H-indole-1-carboxamide (1b). Prepared according to General Procedure A, isolated as a white solid; E:Z ratio: 1:2.5 (1.3 g, 47% over two steps). Analytical data for 1b: 1H NMR: major (Z): 1H NMR (500 MHz, tol-d8) δ 8.06 (d, J=8.8 Hz, 1H), 7.83 (s, 1H), 7.66 (s, 2H), 7.63 (s, 1H), 7.55 (s, 1H), 7.37 (dd, J=8.8, 1.9 Hz, 1H), 6.47 (s, 1H), 6.07 (dt, J=5.8, 1.7 Hz, 1H), 4.52 (p, J=6.7 Hz, 1H), 2.62 (s, 2H), 1.72 (dd, J=6.7, 1.7 Hz, 3H), 1.09 (s, 6H). minor (E): 1H NMR (500 MHz, tol-d8) δ 8.12 (d, J=8.8 Hz, 1H), 7.84-7.83 (m, 2H), 7.63 (s, 2H), 7.37 (dd, J=8.8, 1.9 Hz, 1H), 7.08 (s, 1H), 6.58 (s, 1H), 6.18 (dq, J=12.0, 1.7 Hz, 1H), 5.21 (dq, J=11.9, 6.8 Hz, 1H), 2.63 (s, 2H), 1.56 (dd, J=6.8, 1.6 Hz, 3H), 1.10 (s, 6H). 13C NMR (126 MHz, tol-d8) δ 148.1, 148.0, 140.2, 139.0, 139.0, 139.0, 134.3, 134.2, 132.9, 132.8, 132.1 (q, JC-F=33.2 Hz), 132.0 (q, JC-F=33.3 Hz), 128.7, 127.8, 125.0, 124.4, 123.1, 123.0, 122.7, 122.7, 122.2, 119.5 (q, JC-F=3.6 Hz), 119.3 (q, JC-F=4.0 Hz), 117.1-116.8 (m), 116.5, 116.5, 116.4, 116.4, 104.3, 102.2, 76.8, 76.8, 35.9, 35.9, 25.4, 25.4, 12.3, 9.6. FTIR (ATR) cm−1 3279, 2977, 2932, 1687, 1673, 1650, 1626, 1585, 1563, 1547, 1537, 1474, 1445, 1357, 1330, 1276, 1251, 1172, 1122, 1085, 1055, 1019, 948, 887, 864, 841, 807, 778, 740, 700, 682, 621. HRMS (ESI): Mass calculated for C24H21BrF6N2NaO2 [M+Na]+: 585.058; found 585.059.

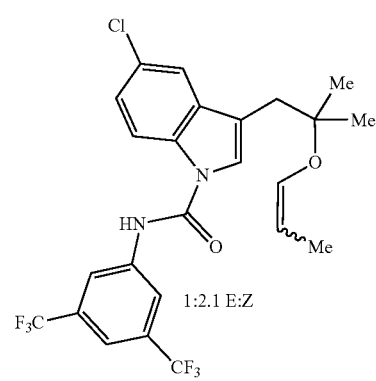

1c

1:2.1 E:Z

N-(3,5-bis(trifluoromethyl)phenyl)-5-chloro-3-(2-methyl-2-(prop-1-en-1-yloxy)propyl)-1H-indole-1-carboxamide (1c). Prepared according to General Procedure A, isolated as a white solid; E:Z ratio: 1:2.1 (1.5 g, 60% over two steps). Analytical data for 1c: 1H NMR: major (Z): 1H NMR (500 MHz, tol-d8) δ 8.13 (d, J=8.8 Hz, 1H), 7.65 (s, 2H), 7.61 (s, 1H), 7.55 (s, 1H), 7.25 (dd, J=8.9, 2.1 Hz, 1H), 7.05 (s, 1H), 6.41 (s, 1H), 6.13-5.99 (m, 1H), 4.52 (p, J=6.6 Hz, 1H), 2.64 (s, 2H), 1.72 (dd, J=6.7, 1.5 Hz, 3H), 1.10 (s, 6H). minor (E): 1H NMR (500 MHz, tol-d8) δ 8.18 (d, J=8.8 Hz, 1H), 7.66 (s, 2H), 7.61 (s, 2H), 7.42 (s, 1H), 7.10 (s, 1H), 6.50 (s, 1H), 6.19 (dd, J=12.1, 1.9 Hz, 1H), 5.21 (dq, J=13.3, 6.8 Hz, 1H), 2.65 (s, 2H), 1.55 (dd, J=6.9, 1.5 Hz, 3H), 1.11 (s, 6H). 13C NMR (126 MHz, tol-d8) δ 148.1, 148.0, 140.2, 139.0, 139.0, 137.3, 136.8, 134.0, 133.9, 132.4, 132.4, 132.1 (q, JC-F=33.4 Hz), 132.0 (q, JC-F=33.5 Hz), 127.1, 126.5, 123.2, 123.2, 122.2, 119.6, 119.6, 119.3 (q, JC-F=3.4 Hz), 117.1, 117.1, 117.0-116.8 (m), 116.2, 116.0, 104.3, 102.2, 76.8, 76.8, 36.0, 35.9, 25.4, 25.4, 14.0, 12.3, 9.5. FTIR (ATR) cm−1 3276, 2977, 2935, 1675, 1547, 1473, 1446, 1388, 1356, 1333, 1275, 1253, 1171, 1122, 1059, 1020, 948, 887, 844, 810, 778, 741, 732, 700, 682, 623. HRMS (ESI): Mass calculated for C24H21ClF6N2NaO2 [M+Na]+: 541.109; found 541.110.

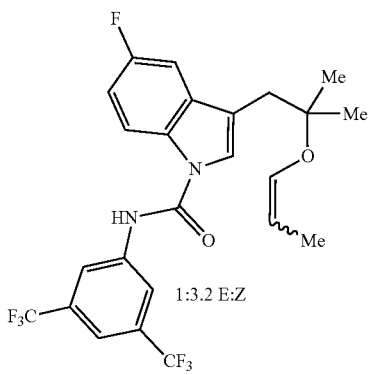

1d

N-(3,5-bis(trifluoromethyl)phenyl)-5-fluoro-3-(2-methyl-2-(prop-1-en-1-yloxy)propyl)-1H-indole-1-carboxamide (1d). Prepared according to General Procedure A, isolated as a white solid; E:Z ratio: 1:3.2 (1.1 g, 46% over two steps). Analytical data for 1d: major (Z): 1H NMR (500 MHz, tol-d8) δ 8.18 (dd, J=9.0, 4.5 Hz, 1H), 7.68 (s, 2H), 7.55 (s, 1H), 7.25 (dd, J=8.8, 2.5 Hz, 1H), 7.16-7.11 (m, 1H), 6.98 (dd, J=8.9, 2.5 Hz, 1H), 6.55 (s, 1H), 6.10 (dq, J=6.3, 1.7 Hz, 1H), 4.52 (p, J=6.7 Hz, 1H), 2.66 (s, 2H), 1.71 (dd, J=6.8, 1.7 Hz, 3H), 1.12 (s, 6H). minor (E): 1H NMR (500 MHz, tol-d8) δ 8.23 (dd, J=9.0, 4.6 Hz, 1H), 7.65 (s, 2H), 7.55 (s, 1H), 7.25 (dd, J=8.8, 2.5 Hz, 1H), 7.13 (s, 1H), 6.98 (dd, J=8.9, 2.5 Hz, 1H), 6.66 (s, 1H), 6.19 (dq, J=12.0, 1.6 Hz, 1H), 5.20 (dq, J=11.9, 6.9 Hz, 1H), 2.67 (s, 2H), 1.55 (dd, J=6.8, 1.6 Hz, 3H), 1.13 (s, 6H). 13C NMR (126 MHz, tol-d8) δ 159.6 (d, JC-F=239.8 Hz), 148.1, 140.2, 139.1, 139.1, 139.1, 132.4, 132.2, 132.2, 132.1, 132.0, 131.9, 131.8, 131.6, 128.7, 127.8, 126.5, 125.0, 124.4, 123.5, 123.4, 122.2, 119.5 (q, JC-F=3.3 Hz), 119.3 (q, JC-F=4.1 Hz), 117.4, 117.4, 117.0-116.7 (m), 116.3 (d, J=9.0 Hz), 116.1 (d, JC-F=9.1 Hz), 112.6 (d, JC-F=25.1 Hz), 105.4 (d, JC-F=23.8 Hz), 105.3 (d, JC-F=23.8 Hz), 104.4, 102.3, 76.9, 76.8, 36.1, 35.9, 25.4, 25.4, 12.3, 9.5. FTIR (ATR) cm−1 3269, 2976, 2917, 1673, 1621, 1596, 1555, 1470, 1446, 1360, 1340, 1276, 1255, 1225, 1168, 1116, 1065, 923, 888, 853, 831, 784, 746, 681, 656, 644. HRMS (ESI): Mass calculated for C24H21F7N2NaO2 [M+Na]+: 525.138; found 525.139.

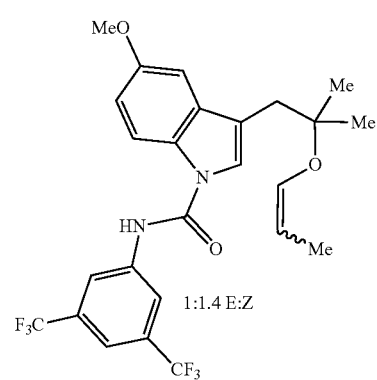

1e

N-(3,5-bis(trifluoromethyl)phenyl)-5-methoxy-3-(2-methyl-2-(prop-1-en-1-yloxy)propyl)-1H-indole-1-carboxamide (1e). Prepared according to General Procedure A, isolated as a tan solid; E:Z ratio: 1:1.4 (1.4 g, 55% over two steps). Analytical data for 1e: major (Z): 1H NMR (500 MHz, tol-d8) δ 8.14 (d, J=9.0 Hz, 1H), 7.66 (d, J=1.5 Hz, 2H), 7.62 (d, J=1.5 Hz, 1H), 7.13 (s, 1H), 7.11 (d, J=1.6 Hz, 1H), 6.96-6.93 (m, 1H), 6.53 (s, 1H), 6.12 (dq, J=6.3, 1.7 Hz, 1H), 4.50 (p, J=6.7 Hz, 1H), 3.52 (s, 3H), 2.76 (s, 2H), 1.68 (dd, J=6.8, 1.7 Hz, 3H), 1.15 (s, 6H). minor (E): 1H NMR (500 MHz, tol-d8) δ 8.18 (d, J=9.0 Hz, 1H), 7.50 (s, 2H), 7.14 (d, J=2.5 Hz, 1H), 7.13 (s, 1H), 7.11 (s, 1H), 6.96 (s, 1H), 6.58 (s, 1H), 6.21 (dq, J=12.0, 1.7 Hz, 1H), 5.17 (dq, J=12.0, 6.8 Hz, 1H), 3.53 (s, 3H), 2.78 (s, 2H), 1.52 (dd, J=6.8, 1.6 Hz, 3H), 1.16 (s, 6H). 13C NMR (126 MHz, tol-d8) δ 156.4, 148.4, 148.3, 140.4, 139.3, 139.2, 136.8, 132.4, 132.3, 132.2, 132.1, 132.0, 131.9, 131.8, 131.6, 131.5, 130.4, 130.2, 128.7, 127.8, 125.0, 122.9, 122.8, 122.3, 120.1, 119.5 (q, JC-F=2.8 Hz), 119.3 (q, JC-F=4.0 Hz), 117.6, 117.5, 116.8-116.4 (m), 115.7, 115.6, 113.2, 113.1, 104.1, 103.1, 103.0, 102.2, 77.1, 77.0, 54.8, 36.5, 36.2, 29.2, 25.5, 25.5, 20.6, 12.3, 9.5. FTIR (ATR) cm−1 3305, 3105, 2973, 2922, 2838, 1678, 1628, 1613, 1595, 1553, 1473, 1362, 1328, 1273, 1171, 1072, 1046, 1016, 936, 918, 885, 843, 811, 782, 759, 701, 681, 648, 635. HRMS (ESI): Mass calculated for C25H24F6N2NaO3 [M+Na]+: 537.158; found 537.159.

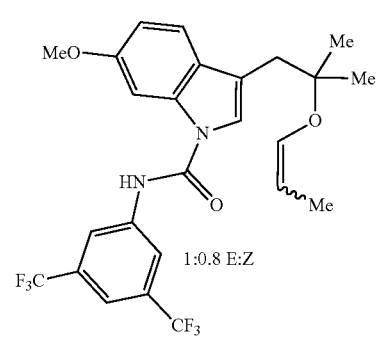

1f

N-(3,5-bis(trifluoromethyl)phenyl)-6-methoxy-3-(2-methyl-2-(prop-1-en-1-yloxy)propyl)-1H-indole-1-carboxamide (1f). Prepared according to General Procedure A, isolated as a white solid; E:Z ratio: 1:0.8 (1.2 g, 48% over two steps). Analytical data for 1f: 1H NMR: major (E): 1H NMR (500 MHz, tol-d8) δ 8.10 (d, J=2.3 Hz, 1H), 7.63 (s, 2H), 7.50 (s, 1H), 7.34 (d, J=8.7 Hz, 1H), 6.99 (d, J=2.1 Hz, 1H), 6.98 (s, 1H), 6.67 (s, 1H), 6.22 (dq, J=11.9, 1.6 Hz, 1H), 5.19 (dq, J=12.0, 6.8 Hz, 1H), 3.51 (s, 3H), 2.78 (s, 2H), 1.53 (dd, J=6.9, 1.6 Hz, 3H), 1.16 (s, 6H). minor (Z): 1H NMR (500 MHz, tol-d8) δ 8.07 (d, J=2.3 Hz, 1H), 7.66 (s, 2H), 7.50 (s, 1H), 7.33 (d, J=8.6 Hz, 1H), 6.99 (d, J=2.1 Hz, 1H), 6.94 (s, 1H), 6.58 (s, 1H), 6.13 (dq, J=5.7, 1.8 Hz, 1H), 4.51 (p, J=6.7 Hz, 1H), 3.51 (s, 3H), 2.77 (s, 2H), 1.70 (dd, J=6.8, 1.7 Hz, 3H), 1.15 (s, 6H). 13C NMR (126 MHz, tol-d8) δ 158.7, 148.6 (d, JC-F=13.0 Hz), 140.4, 139.4, 139.3, 139.3, 137.3, 136.9, 136.8, 132.0 (q, JC-F=33.6 Hz), 131.9 (q, JC-F=33.2 Hz), 127.1, 126.6, 124.2, 122.3, 120.2 (d, JC-F=3.9 Hz), 120.1, 119.4 (dq, JC-F=25.0, 8.8, 3.5 Hz), 117.9, 117.2-116.1 (m), 112.7, 112.7, 104.2, 102.2, 99.2, 99.1, 77.1, 77.1, 54.7, 36.2, 36.1, 29.9, 25.6, 25.5, 20.6, 12.3, 9.6. FTIR (ATR) cm−1 3347, 3129, 2999, 2950, 2923, 2854, 1711, 1666, 1620, 1580, 1552, 1548, 1530, 1485, 1445, 1359, 1324, 1280, 1255, 1237, 1178, 1129, 1039, 922, 820. HRMS (ESI): Mass calculated for C25H25F6N2O3 [M+H]+: 515.176; found 515.177.

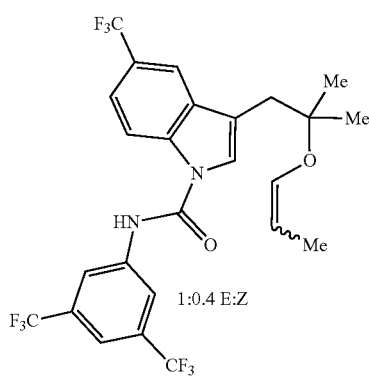

N-(3,5-bis(trifluoromethyl)phenyl)-5-trifluoromethyl-3-(2-methyl-2-(prop-1-en-1-yloxy)propyl)-1H-indole-1-carboxamide (1g). Prepared according to General Procedure A, isolated as a white solid; E:Z ratio: 1:0.4 (30 mmol scale, 0.066 g, 40% over two steps). Analytical data for 1g: major (E): 1H NMR (500 MHz, tol-d8) δ 8.25 (d, J=8.7 Hz, 1H), 8.06-8.02 (m, 1H), 7.66 (s, 1H), 7.64 (s, 2H), 7.50-7.44 (m, 1H), 7.12 (s, 1H), 6.67 (s, 1H), 6.13 (dt, J=12.0, 1.7 Hz, 1H), 5.16 (dq, J=11.8, 6.9 Hz, 1H), 2.64 (s, 2H), 1.51 (dd, J=6.9, 1.6 Hz, 3H), 1.06 (s, 6H). minor (Z): 1H NMR (500 MHz, tol-d8) δ 8.21 (d, J=8.7 Hz, 1H), 8.02-7.99 (m, 1H), 7.66 (s, 2H), 7.48 (d, J=8.5 Hz, 1H), 7.38 (s, 2H), 6.53 (s, 1H), 6.07-5.94 (m, 1H), 4.48 (p, J=6.7 Hz, 1H), 2.63 (s, 2H), 1.64 (dd, J=6.8, 1.7 Hz, 3H), 1.06 (s, 6H). 13C NMR (126 MHz, tol-d8) δ 152.2, 148.0, 147.9, 140.0, 139.7, 138.9, 138.9, 137.3, 136.8, 132.0 (q, JC-F=33.5 Hz), 132.0 (t, JC-F=33.1 Hz), 130.9, 130.8, 128.7, 127.8, 123.7, 123.6, 122.2, 121.7-121.3 (m), 119.6 (q, JC-F=4.1 Hz), 119.4 (q, JC-F=3.4 Hz), 117.9, 117.5 (q, JC-F=4.4 Hz), 117.4 (d, JC-F=4.3 Hz), 117.2-117.0 (m), 115.5, 115.4, 104.4, 102.5, 76.8, 76.7, 61.2, 36.0, 35.8, 32.0, 29.9, 29.5, 25.4, 25.3, 13.9, 12.2, 9.4. FTIR (ATR) cm−1 3287, 3111, 3090, 3054, 2931, 2858, 1679, 1622, 1549, 1473, 1448, 1387, 1349, 1320, 1275, 1240, 1216, 1167, 1130, 1058, 1020, 946, 921, 883, 845, 827, 809, 781, 750, 728, 700, 681, 657. HRMS (ESI): Mass calculated for C25H20F9N2O2 [M−H]−: 551.139; found 551.139.

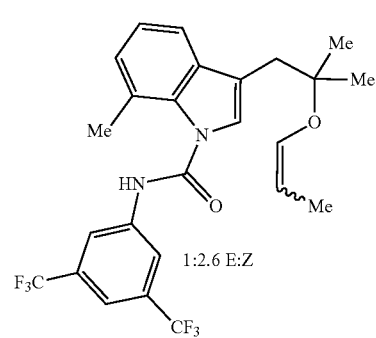

N-(3,5-bis(trifluoromethyl)phenyl)-7-methyl-3-(2-methyl-2-(prop-1-en-1-yloxy)propyl)-1H-indole-1-carboxamide (1h). Prepared according to General Procedure A, isolated as a white solid; E:Z ratio: 1:2.6 (56% over two steps). Analytical data for 1h: 1H NMR: major (Z): 1H NMR (500 MHz, tol-d8) δ 7.62 (d, J=1.5 Hz, 2H), 7.46 (s, 1H), 7.38 (s, 1H), 7.19-7.13 (m, 2H), 7.00 (s, 1H), 6.61 (s, 1H), 6.11 (dq, J=6.3, 1.7 Hz, 1H), 4.48 (p, J=6.7 Hz, 1H), 2.77 (s, 2H), 2.40 (s, 3H), 1.68 (dd, J=6.8, 1.7 Hz, 3H), 1.13 (s, 6H). minor (E): 1H NMR (500 MHz, tol-d8) δ 7.59 (s, 2H), 7.40 (s, 1H), 7.17 (s, 1H), 7.16 (s, 1H), 7.01-6.99 (m, 2H), 6.68 (s, 1H), 6.21 (dq, J=11.8, 1.6 Hz, 1H), 5.16 (dq, J=11.9, 6.8 Hz, 1H), 2.79 (s, 2H), 2.41 (s, 3H), 1.51 (dd, J=6.8, 1.6 Hz, 3H), 1.14 (s, 6H). 13C NMR (126 MHz, tol-d8) δ 148.9, 148.9, 139.2, 139.2, 139.2, 134.6, 134.5, 132.4, 132.2 (q, JC-F=34.0 Hz), 132.1 (q, JC-F=33.5 Hz), 128.9, 128.7, 128.0, 127.8, 127.1, 126.5, 125.6, 125.5, 125.0, 124.3, 123.9, 122.9, 122.2, 120.0, 118.7 (q, JC-F=4.5 Hz), 118.6 (q, JC-F=4.2 Hz), 116.8 (h, JC-F=4.1 Hz), 116.5, 116.5, 103.9, 102.0, 77.1, 77.0, 36.0, 35.9, 25.5 (d, JC-F=3.0 Hz), 20.3, 12.3, 9.5. FTIR (ATR) cm−1 3269, 3092, 3054, 2977, 2862, 2361, 2337, 1718, 1684, 1653, 1617, 1540, 1507, 1473, 1443, 1407, 1383, 1345, 1328, 1274, 1255, 1206, 1175, 1131, 1043, 944, 918, 891, 861, 838, 785, 741, 701, 682. HRMS (ESI): Mass calculated for C25H23F6N2O2 [M−H]−: 497.167; found 497.167.

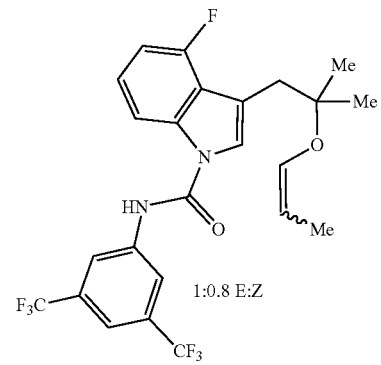

N-(3,5-bis(trifluoromethyl)phenyl)-4-fluoro-3-(2-methyl-2-(prop-1-en-1-yloxy)propyl)-1H-indole-1-carboxamide (1i). Prepared according to General Procedure A, isolated as a white solid; E:Z ratio: 1:0.8 (59% over two steps). Analytical data for 1i: major (E): 1H NMR (500 MHz, tol-d8) δ 8.15 (d, J=8.4 Hz, 1H), 7.64 (s, 1H), 7.61 (s, 2H), 7.10 (s, 1H), 7.00-6.98 (m, 0H), 6.79 (d, J=7.7 Hz, 1H), 6.77 (d, J=8.8 Hz, 1H), 6.73 (s, 1H), 6.19 (dq, J=12.0, 1.7 Hz, 1H), 5.15 (dq, J=11.9, 6.8 Hz, 1H), 3.10 (s, 2H), 1.50 (dd, J=6.8, 1.6 Hz, 3H), 1.18 (s, 6H). minor (Z): 1H NMR (500 MHz, tol-d8) δ 8.09 (d, J=8.3 Hz, 1H), 7.50 (s, 2H), 7.10 (s, 1H), 7.06 (s, 1H), 6.99 (d, J=2.6 Hz, 2H), 6.56 (s, 1H), 6.08 (dq, J=6.1, 1.7 Hz, 1H), 4.46 (p, J=6.7 Hz, 1H), 3.08 (s, 2H), 1.66 (dd, J=6.7, 1.7 Hz, 3H), 1.17 (s, 6H). 13C NMR (126 MHz, tol-d8) δ 157.9, 157.9, 156.0, 155.9, 148.2 (d, JC-F=17.4 Hz), 140.4, 139.3, 139.1, 139.1, 137.9 (d, JC-F=9.6 Hz), 137.7 (d, JC-F=9.8 Hz), 136.8, 132.0 (q, JC-F=33.5 Hz), 131.9 (q, JC-F=33.4 Hz), 127.1, 125.3 (d, JC-F=8.0 Hz), 124.2, 122.7, 122.5, 122.2 (d, JC-F=3.7 Hz), 119.7, 119.6, 119.6-119.4 (m), 119.3 (q, JC-F=3.3 Hz), 117.0-116.7 (m), 115.4 (d, JC-F=3.2 Hz), 115.3 (d, JC-F=3.1 Hz), 111.5 (d, JC-F=3.8 Hz), 111.4 (d, JC-F=3.6 Hz), 108.6 (d, JC-F=19.6 Hz), 108.5 (d, JC-F=19.8 Hz), 104.2, 102.0, 77.2 (d, JC-F=3.8 Hz), 36.6 (d, JC-F=3.7 Hz), 36.5 (d, JC-F=3.1 Hz), 25.2, 25.2, 20.6, 12.3, 9.5. FTIR (ATR) cm−1 3293, 3101, 3044, 2981, 2925, 2857, 1723, 1680, 1628, 1548, 1494, 1473, 1436, 1388, 1353, 1342, 1278, 1244, 1185, 1133, 1089, 1048, 958, 889, 853, 829, 788, 750, 737, 701, 683. HRMS (ESI): Mass calculated for C24H21F7N2NaO2 [M+Na]+: 525.138; found 525.139.

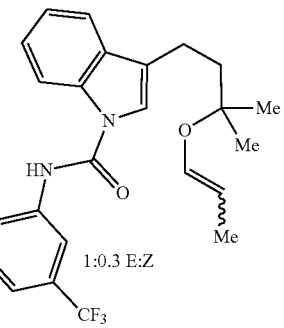

1j

1:0.3 E:Z

N-(3,5-bis(trifluoromethyl)phenyl)-4-fluoro-3-(2-methyl-2-(prop-1-en-1-yloxy)butyl)-1H-indole-1-carboxamide (1j). Prepared according to above procedure for synthesis of 1j/General Procedure A, isolated as an off-white solid; E:Z ratio: 1:0.3 (65% over two steps). Analytical data for 1j: major (E): 1H NMR (500 MHz, tol-d8) δ 8.30 (d, J=8.0 Hz, 1H), 7.74-7.71 (m, 2H), 7.52 (s, 1H), 7.51-7.48 (m, 1H), 7.24 (ddd, J=8.4, 7.2, 1.3 Hz, 1H), 7.17 (t, J=7.3 Hz, 1H), 6.74 (s, 1H), 6.48 (s, 1H), 6.26 (dq, J=11.8, 1.5 Hz, 1H), 5.22 (dq, J=12.0, 6.8 Hz, 1H), 2.86-2.71 (m, 2H), 1.90-1.81 (m, 2H), 1.57 (dd, J=6.7, 1.6 Hz, 3H), 1.18 (s, 6H). minor (Z): 1H NMR (500 MHz, tol-d8) δ 8.29 (s, 1H), 7.75 (s, 1H), 7.69 (d, J=1.6 Hz, 2H), 7.54 (s, 1H), 7.24 (t, J=7.2 Hz, 1H), 7.18 (t, J=6.7 Hz, 1H), 6.77 (s, 1H), 6.42 (s, 1H), 6.17 (dt, J=6.2, 1.7 Hz, 1H), 4.56 (p, J=6.6 Hz, 1H), 2.88-2.68 (m, 2H), 1.89-1.82 (m, 2H), 1.79 (dd, J=6.7, 1.7 Hz, 3H), 1.19 (s, 6H). 13C NMR (126 MHz, tol-d8) δ 148.4, 148.4, 140.4, 139.3, 139.2, 139.2, 139.1, 137.3, 136.8, 136.1, 132.0 (q, JC-F=33.4 Hz), 130.3, 130.3, 128.7, 127.8, 126.6, 125.0, 122.8, 122.8, 122.5, 122.3, 120.1, 119.4, 119.4, 119.3, 116.9-116.5 (m), 115.2, 115.2, 115.1, 103.6, 102.2, 76.2, 41.0, 41.0, 25.5, 25.4, 19.2, 19.1, 12.4, 9.3. FTIR (ATR) cm−1 3367, 2984, 2932, 2864, 1711, 1670, 1629, 1561, 1475, 1452, 1389, 1362, 1337, 1279, 1251, 1215, 1169, 1113, 1075, 1016, 928, 909, 877, 836, 765, 744, 729, 697, 682, 641. HRMS (ESI): Mass calculated for C25H24F6N2NaO2 [M+Na]+: 521.163; found 521.164.

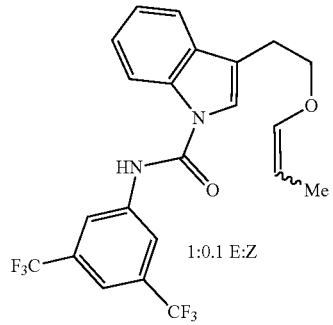

1k

1:0.1 E:Z

N-(3,5-bis(trifluoromethyl)phenyl)-3-(2-(prop-1-en-1-yloxy)ethyl)-1H-indole-1-carboxamide (1k). Prepared according to General Procedure B, isolated as a white solid; E:Z ratio: 1:0.1 (50% over two steps). Analytical data for 1k: 1H NMR: major (E): 1H NMR (500 MHz, tol-d8) δ 8.29 (d, J=8.3 Hz, 1H), 7.68 (s, 2H), 7.50 (s, 1H), 7.32 (d, J=7.8 Hz, 1H), 7.20 (t, J=7.8 Hz, 1H), 7.10 (t, J=5.8 Hz, 1H), 6.90 (s, 1H), 6.66 (s, 1H), 6.20 (dq, J=12.5, 1.6 Hz, 1H), 4.75 (dq, J=13.2, 6.7 Hz, 1H), 3.72 (t, J=6.3 Hz, 2H), 2.80 (t, J=6.3 Hz, 2H), 1.47 (dd, J=6.7, 1.6 Hz, 3H). minor (Z): 1H NMR (500 MHz, tol-d8) δ 8.23 (d, J=8.3 Hz, 1H), 7.70 (s, 3H), 7.34 (d, J=7.3 Hz, 1H), 7.23-7.20 (m, 1H), 7.13 (d, J=7.9 Hz, 1H), 7.09 (s, 2H), 6.88 (s, 1H), 6.62 (s, 1H), 5.83 (dq, J=5.7, 1.8 Hz, 1H), 4.41 (p, J=6.7 Hz, 1H), 2.77 (t, J=6.8 Hz, 2H), 1.69 (dd, J=6.8, 1.7 Hz, 3H). 13C NMR (126 MHz, tol-d8) δ 148.4, 146.3, 145.3, 139.2, 135.9, 135.8, 132.1 (q, JC-F=33.4 Hz), 132.0 (q, JC-F=33.6 Hz), 130.2, 130.0, 128.7, 127.8, 126.6, 124.9, 124.4, 122.8, 122.3, 120.7, 120.1, 119.4 (q, JC-F=4.3 Hz), 119.2, 119.0, 118.6, 118.5, 116.7 (p, JC-F=4.1 Hz), 115.2, 115.0, 101.2, 98.7, 70.9, 67.7, 25.4, 25.0, 12.2, 9.3. FTIR (ATR) cm−1 3392, 3118, 2942, 2926, 2891, 1717, 1684, 1675, 1653, 1617, 1558, 1507, 1473, 1455, 1388, 1361, 1324, 1273, 1254, 1224, 1209, 1163, 1116, 1085, 1030, 1004, 929, 877, 865, 835, 785, 768, 748, 727, 695, 681, 668, 637. HRMS (ESI): Mass calculated for C22H18F6N2NaO2 [M+Na]+: 479.116; found 479.118.

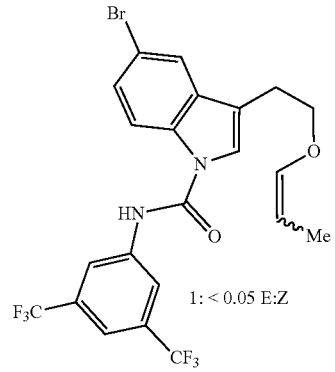

1l

1: < 0.05 E:Z

N-(3,5-bis(trifluoromethyl)phenyl)-5-bromo-3-(2-(prop-1-en-1-yloxy)ethyl)-1H-indole-1-carboxamide (1l). Prepared according to General Procedure B, isolated as a white solid; E:Z ratio: 1:<0.05 (50% over two steps). Analytical data for 1l: 1H NMR (500 MHz, tol-d8) δ 8.14 (d, J=8.8 Hz, 1H), 7.67 (d, J=1.9 Hz, 1H), 7.61 (d, J=1.5 Hz, 2H), 7.56 (s, 1H), 7.37 (dd, J=8.8, 2.0 Hz, 1H), 6.76 (s, 1H), 6.24 (s, 1H), 6.22 (dq, J=12.7, 1.3 Hz, 1H), 4.77 (dq, J=13.2, 6.7 Hz, 1H), 3.66 (t, J=6.1 Hz, 2H), 2.69 (t, J=6.0 Hz, 2H), 1.50 (dd, J=6.7, 1.6 Hz, 3H). 13C NMR (126 MHz, tol-d8) δ 147.9, 146.3, 138.9, 137.3, 136.8, 134.6, 132.0 (q, JC-F=33.5 Hz), 131.7, 128.7, 128.0, 127.8, 122.2, 121.9, 121.6, 119.5 (q, JC-F=3.0 Hz), 118.2, 116.5, 98.6, 67.4, 24.7, 12.2. FTIR (ATR) cm−1 3340, 3264, 3106, 2934, 2885, 1723, 1677, 1550, 1472, 1440, 1385, 1350, 1279, 1247, 1205, 1169, 1049, 924, 885, 838, 813, 743, 700, 682, 666, 654, 594. HRMS (ESI): Mass calculated for C22H17BrF6N2NaO2 [M+Na]+: 557.027; found 557.026.

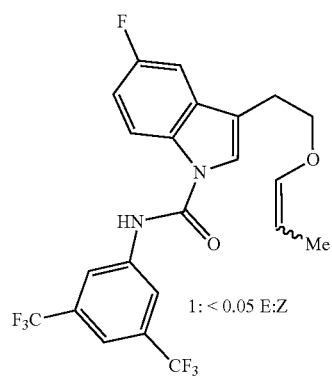

1m
1: < 0.05 E:Z

N-(3,5-bis(trifluoromethyl)phenyl)-5-fluoro-3-(2-(prop-1-en-1-yloxy)ethyl)-1H-indole-1-carboxamide (1m). Prepared according to General Procedure B, isolated as a white solid; E:Z ratio: 1:<0.05 (46% over two steps). Analytical data for 1m: 1H NMR (500 MHz, tol-d8) δ 8.24 (dd, J=9.1, 4.5 Hz, 1H), 7.62 (s, 2H), 7.56 (s, 1H), 7.11 (dd, J=9.0, 2.9 Hz, 1H), 6.98 (ddd, J=9.0, 9.0, 2.6 Hz, 1H), 6.80 (s, 1H), 6.24 (dq, J=12.8, 1.7 Hz, 1H), 6.23 (s, 1H), 4.78 (dq, J=13.2, 6.7 Hz, 1H), 3.69 (t, J=6.2 Hz, 2H), 2.80-2.65 (m, 2H), 1.51 (dd, J=6.7, 1.6 Hz, 3H). 13C NMR (126 MHz, tol-d8) δ 159.5 (d, JC-F=240.3 Hz), 148.0, 146.3, 139.0, 137.3, 136.8, 132.3, 132.1, 131.9, 131.6, 130.9 (d, JC-F=9.4 Hz), 128.7, 127.8, 125.0, 122.2, 122.0, 119.5 (d, JC-F=4.2 Hz), 118.6 (d, JC-F=4.1 Hz), 116.8 (d, JC-F=5.1 Hz), 116.6 (d, JC-F=8.9 Hz), 112.9 (d, JC-F=25.1 Hz), 104.7 (d, JC-F=23.9 Hz), 98.5, 67.4, 24.9, 12.3. FTIR (ATR) cm−1 3336, 3117, 3046, 3019, 2930, 2891, 1721, 1680, 1620, 1599, 1562, 1552, 1472, 1442, 1388, 1356, 1340, 1281, 1250, 1204, 1167, 1122, 1112, 1083, 1057, 1028, 1012, 983, 925, 909, 898, 886, 861, 839, 819, 765, 744, 733, 711, 701, 684, 622. HRMS (ESI): Mass calculated for C22H17F7N2NaO2 [M+Na]+: 497.107; found 497.108.

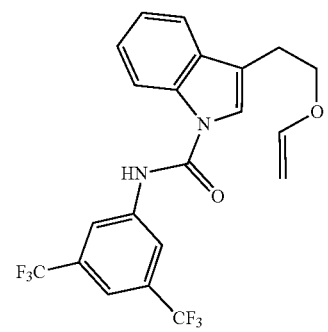

1n

N-(3,5-bis(trifluoromethyl)phenyl)-3-(2-(vinyloxy)ethyl)-1H-indole-1-carboxamide (1n). Prepared according to General Procedure C, isolated as a white solid (55%). Analytical data for 1n: 1H NMR (500 MHz, tol-d8) δ 8.26 (d, J=8.3 Hz, 1H), 7.62 (d, J=1.5 Hz, 2H), 7.50 (s, 1H), 7.33 (dt, J=7.8, 0.9 Hz, 1H), 7.21 (ddd, J=8.4, 7.1, 1.3 Hz, 1H), 7.12 (td, J=7.7, 0.8 Hz, 1H), 6.81 (s, 1H), 6.40 (dd, J=14.4, 6.9 Hz, 1H), 6.37 (s, 1H), 4.18 (dd, J=14.4, 2.1 Hz, 1H), 3.97 (dd, J=6.8, 2.1 Hz, 1H), 3.73 (t, J=6.4 Hz, 2H), 2.81 (td, J=6.4, 1.0 Hz, 2H). 13C NMR (126 MHz, tol-d8) δ 151.4, 148.3, 139.1, 135.9, 132.0 (q, JC-F=33.4 Hz), 130.0, 126.6, 122.8, 122.2, 120.7, 120.1, 119.5 (d, JC-F=3.9 Hz), 119.0, 118.5, 116.8 (p, JC-F=3.9 Hz), 115.2, 86.5, 66.7, 24.7. FTIR (ATR) cm−1 3389, 3120, 3068, 2922, 2853, 1721, 1667, 1630, 1546, 1474, 1453, 1441, 1411, 1390, 1361, 1350, 1325, 1312, 1277, 1249, 1209, 1167, 1121, 1058, 1027, 1015, 1002, 981, 951, 935, 913, 905, 884, 867, 836, 823, 771, 754, 742, 700, 683, 647, 635. HRMS (ESI): Mass calculated for C21H16F6N2NaO2 [M+Na]+: 465.101; found 465.101.

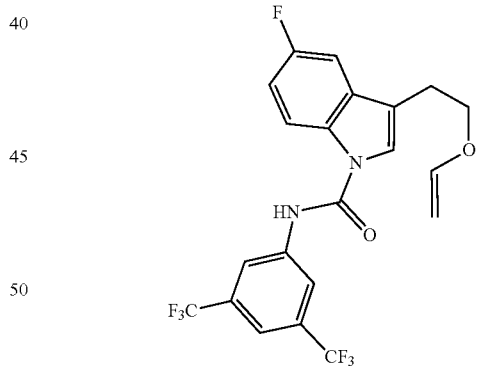

1o

N-(3,5-bis(trifluoromethyl)phenyl)-5-fluoro-3-(2-(vinyloxy)ethyl)-1H-indole-1-carboxamide (1o). Prepared according to General Procedure C, isolated as a white solid (45%). Analytical data for 1o: 1H NMR (500 MHz, tol-d8) δ 8.18 (dd, J=9.1, 4.5 Hz, 1H), 7.59 (s, 2H), 7.51 (s, 1H), 7.04 (dd, J=8.7, 2.6 Hz, 1H), 6.93 (ddd, J=9.0, 9.0, 2.4 Hz, 1H), 6.72 (s, 1H), 6.37 (dd, J=14.4, 6.8 Hz, 1H), 6.22 (s, 1H), 4.16 (dd, J=14.4, 2.1 Hz, 1H), 3.97 (dd, J=6.9, 2.1 Hz, 1H), 3.64 (t, J=6.2 Hz, 2H), 2.67 (t, J=6.2 Hz, 2H). 13C NMR (126 MHz, tol-d8) δ 159.5 (d, JC-F=240.3 Hz), 151.3, 148.0, 139.0, 132.3, 132.0 (q, JC-F=33.5 Hz), 130.9 (d, JC-F=9.4 Hz), 128.7, 127.8, 127.1, 126.6, 125.0, 122.2, 122.0, 120.1, 119.5 (q, JC-F=3.1 Hz), 118.4 (d, JC-F=4.1

Hz), 116.9 (p, JC-F=3.7 Hz), 116.6 (d, JC-F=9.0 Hz), 112.9 (d, JC-F=25.1 Hz), 104.6 (d, JC-F=23.7 Hz), 86.6, 66.5, 24.6. FTIR (ATR) cm−1 3379, 3120, 2986, 2941, 2887, 1717, 1643, 1634, 1598, 1545, 1470, 1441, 1387, 1370, 1357, 1327, 1281, 1250, 1208, 1161, 1084, 1051, 1020, 952, 907, 885, 860, 811, 772, 759, 745, 713, 699, 682, 620. HRMS (ESI): Mass calculated for C21H15F7N2NaO2 [M+Na]+: 483.091; found 483.093.

Pyranoindoles (2)

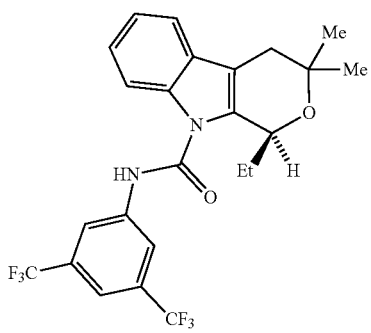

(S)—N-(3,5-bis(trifluoromethyl)phenyl)-1-ethyl-3,3-dimethyl-3,4-dihydropyrano[3,4-b]indole-9(1H)-carboxamide (2a). Prepared according to General Procedure D, isolated as a white solid in 97:3 e.r. (18 mg, 89%). Crystals suitable for X-ray diffraction analysis were grown by slow diffusion of dichloromethane and hexanes. Analytical data for 2a: 1H NMR (500 MHz, CDCl₃) δ 8.08 (s, 2H), 7.71 (s, 2H), 7.63 (d, J=8.2 Hz, 1H), 7.51 (dd, J=7.5, 1.5 Hz, 1H), 7.33 (td, J=8.2, 1.5 Hz, 1H), 7.29 (td, J=7.4, 1.1 Hz, 1H), 5.17 (dq, J=5.4, 2.6 Hz, 1H), 2.76 (dd, J=15.8, 2.5 Hz, 1H), 2.62 (dd, J=15.7, 2.1 Hz, 1H), 1.95 (dqd, J=14.8, 7.4, 3.0 Hz, 1H), 1.79 (ddd, J=14.0, 7.4, 6.2 Hz, 1H), 1.47 (s, 3H), 1.31 (s, 3H), 0.86 (t, J=7.4 Hz, 3H). 13C NMR (126 MHz, CDCl3) δ 149.4, 138.6, 135.4, 135.3, 132.9 (q, JC-F=33.9 Hz), 129.5, 124.0, 122.9 (q, JC-F=273.1 Hz), 122.8, 119.2, 119.1, 119.1, 118.5-117.6 (m), 115.7, 111.3, 71.1, 69.1, 33.6, 30.3, 27.3, 23.0, 9.0. FTIR (ATR) cm−1 3057, 2976, 2940, 2159, 1668, 1629, 1548, 1474, 1455, 1383, 1366, 1336, 1306, 1205, 1170, 1142, 1107, 1016, 945, 884, 846, 740, 71, 681. HRMS (ESI): Mass calculated for C24H22F6N2NaO2 [M+Na]+: 507.1478; found 507.1483.

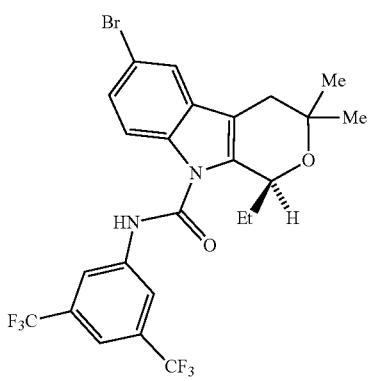

(S)—N-(3,5-bis(trifluoromethyl)phenyl)-5-bromo-1-ethyl-3,3-dimethyl-3,4-dihydropyrano[3,4-b]indole-9(1H)-carboxamide (2b). Prepared according to General Procedure D, isolated as a white solid in 95:5 e.r. (14 mg, 71%). Analytical data for 2b: 1H NMR (500 MHz, CDCl₃) δ 8.05 (s, 2H), 7.70 (s, 1H), 7.60 (d, J=2.0 Hz, 1H), 7.58 (s, 1H), 7.49 (d, J=8.7 Hz, 1H), 7.38 (dd, J=8.8, 2.0 Hz, 1H), 5.23-5.01 (m, 1H), 2.70 (dd, J=15.7, 2.5 Hz, 1H), 2.55 (dd, J=15.7, 2.2 Hz, 1H), 1.91 (dqd, J=14.6, 7.3, 2.8 Hz, 1H), 1.74 (dp, J=14.1, 7.0 Hz, 1H), 1.44 (s, 3H), 1.27 (s, 3H), 0.83 (t, J=7.3 Hz, 3H). 13C NMR (126 MHz, CDCl₃) δ 149.0, 138.3, 136.6, 134.2, 133.0 (q, JC-F=33.9 Hz), 131.1, 126.6, 123.9, 121.9, 121.8, 119.3, 118.5-118.2 (m), 116.0, 115.1, 112.9, 71.1, 69.0, 33.5, 30.2, 27.3, 22.9, 9.0. FTIR (ATR) cm−1 3266, 3229, 3171, 3124, 3099, 2973, 2933, 2910, 2875, 2841, 1676, 1631, 1557, 1475, 1438, 1380, 1368, 1347, 1307, 1275, 1181, 1142, 1125, 1111, 1061, 1017, 1002, 986, 941, 891, 849, 823, 802, 776, 747, 729, 703, 681, 657, 622. HRMS (ESI): Mass calculated for C24H21BrF6N2NaO2 [M+Na]+: 585.058; found 585.058.

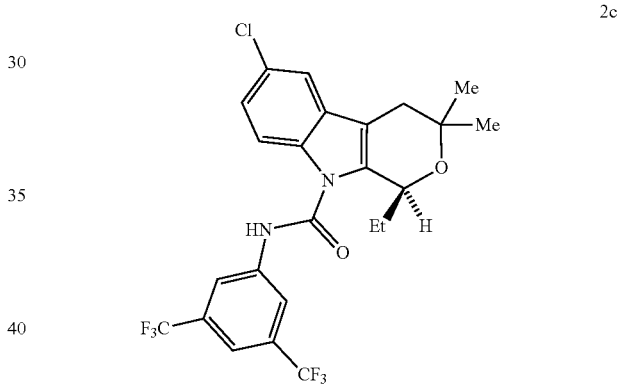

(S)—N-(3,5-bis(trifluoromethyl)phenyl)-5-chloro-1-ethyl-3,3-dimethyl-3,4-dihydropyrano[3,4-b]indole-9(1H)-carboxamide (2c). Prepared according to General Procedure D, isolated as a white solid in 97:3 e.r. (18 mg, 88%). Analytical data for 2c: 1H NMR (500 MHz, CDCl₃) δ 8.17-7.93 (m, 2H), 7.70 (s, 1H), 7.61 (s, 1H), 7.53 (d, J=8.8 Hz, 1H), 7.44 (d, J=2.2 Hz, 1H), 7.24 (s, 0H), 7.24 (dd, J=8.8, 2.2 Hz, 0H), 5.11 (dq, J=5.4, 2.5, 2.5, 2.5 Hz, 1H), 2.70 (dd, J=15.7, 2.5 Hz, 1H), 2.55 (dd, J=15.7, 2.2 Hz, 1H), 1.91 (dqd, J=14.7, 7.4, 3.0 Hz, 1H), 1.82-1.64 (m, 1H), 1.44 (s, 3H), 1.27 (s, 3H), 0.84 (t, J=7.3 Hz, 3H). 13C NMR (126 MHz, CDCl3) δ 149.1, 138.4, 136.8, 133.8, 132.9 (q, JC-F=33.8 Hz), 130.6, 128.5, 123.9, 122.9 (q, JC-F=270.6 Hz), 119.3 (d, JC-F=4.1 Hz), 118.8, 118.3 (p, JC-F=3.8 Hz), 115.2, 112.4, 71.1, 69.0, 33.5, 30.2, 27.3, 22.9, 9.0. FTIR (ATR) cm−1 3244, 3174, 3093, 2976, 2938, 2913, 2877, 2855, 1667, 1567, 1475, 1442, 1380, 1368, 1348, 1306, 1277, 1175, 1145, 1111, 1075, 1019, 946, 890, 802, 736, 682. HRMS (ESI): Mass calculated for C24H21ClF6N2NaO2 [M+Na]+: 541.1090; found 541.1100.

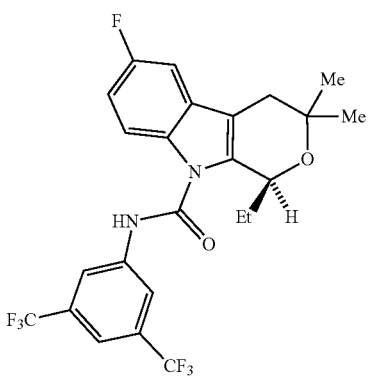

2d (S)—N-(3,5-bis(trifluoromethyl)phenyl)-5-fluoro-1-ethyl-3,3-dimethyl-3,4-dihydropyrano[3,4-b]indole-9(1H)-carboxamide (2d). Prepared according to General Procedure D, isolated as a white solid in 94:6 e.r. (10 mg, 52%). Analytical data for 2d: 1H NMR (500 MHz, CDCl$_3$) δ 8.04 (d, J=1.4 Hz, 2H), 7.69 (s, 1H), 7.58-7.54 (m, 1H), 7.56 (s, 1H), 7.13 (dd, J=8.5, 2.6 Hz, 1H), 7.02 (td, J=8.9, 2.6 Hz, 1H), 5.12 (dq, J=5.4, 2.5 Hz, 1H), 2.70 (dd, J=15.7, 2.5 Hz, 1H), 2.54 (dd, J=15.7, 2.2 Hz, 1H), 1.92 (dqd, J=14.8, 7.4, 3.0 Hz, 1H), 1.75 (dp, J=14.1, 7.2 Hz, 1H), 1.44 (s, 3H), 1.28 (s, 3H), 0.84 (t, J=7.3 Hz, 3H). 13C NMR (126 MHz, CDCl$_3$) δ 159.2 (d, JC-F=240.7 Hz), 149.2, 138.4, 137.1, 132.9 (q, JC-F=33.9 Hz), 131.8, 130.4 (d, JC-F=9.6 Hz), 124.0, 121.8, 119.2 (d, JC-F=3.9 Hz), 118.2, 115.7 (d, JC-F=4.0 Hz), 112.3 (d, JC-F=9.1 Hz), 111.6 (d, JC-F=25.5 Hz), 104.8 (d, JC-F=23.6 Hz), 71.1, 69.1, 33.6, 30.2, 27.3, 22.9, 9.0. FTIR (ATR) cm−1 3270, 3191, 3100, 2975, 2938, 2915, 2877, 2849, 1722, 1672, 1626, 1563, 1556, 1471, 1459, 1445, 1381, 1369, 1351, 1336, 1310, 1275, 1186, 1135, 1107, 1060, 1018, 1002, 944, 892, 863, 855, 831, 802, 703, 682, 663. HRMS (ESI): Mass calculated for C24H21F7N2NaO2 [M+Na]+: 525.138; found 525.138.

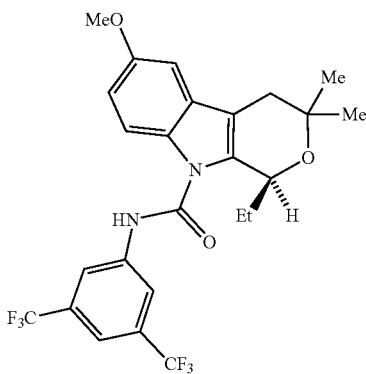

2e (S)—N-(3,5-bis(trifluoromethyl)phenyl)-5-methoxy-1-ethyl-3,3-dimethyl-3,4-dihydropyrano[3,4-b]indole-9(1H)-carboxamide (2e). Prepared according to General Procedure D, isolated as a white solid in 96:4 e.r. (18 mg, 90%). Analytical data for 2e: 1H NMR (500 MHz, CDCl$_3$) δ 8.04 (t, J=2.5 Hz, 2H), 7.65 (dd, J=15.5, 4.3 Hz, 2H), 7.49 (dd, J=8.6, 3.6 Hz, 1H), 6.93 (d, J=2.6 Hz, 1H), 6.92-6.88 (m, 1H), 5.13 (dt, J=5.7, 2.8 Hz, 1H), 3.86 (s, 2H), 2.70 (dd, J=15.6, 2.6 Hz, 1H), 2.56 (dd, J=15.6, 2.2 Hz, 1H), 1.92 (ddp, J=14.8, 7.5, 3.8 Hz, 1H), 1.82-1.70 (m, 1H), 1.44 (s, 2H), 1.28 (s, 2H), 0.84 (t, J=7.3 Hz, 2H). 13C NMR (126 MHz, CDCl3) δ 156.0, 149.4, 138.7, 136.3, 132.8 (q, JC-F=33.7 Hz), 130.5, 129.9, 122.9 (q, JC-F=272.9 Hz), 119.2 (d, JC-F=4.1 Hz), 118.0, 115.7, 112.3 (d, JC-F=24.6 Hz), 101.9, 71.1, 69.3, 55.8, 33.7, 30.3, 27.3, 23.0, 9.0. FTIR (ATR) cm−1 3270, 2982, 2941, 2835, 1668, 1625, 1548, 1471, 1383, 1359, 1275, 1235, 1205, 1170, 1129, 1106, 1041, 1014, 999, 946, 888, 835, 803, 739, 681, 613, 581. HRMS (ESI): Mass calculated for C25H24F6N2NaO3 [M+Na]+: 537.158; found 537.158.

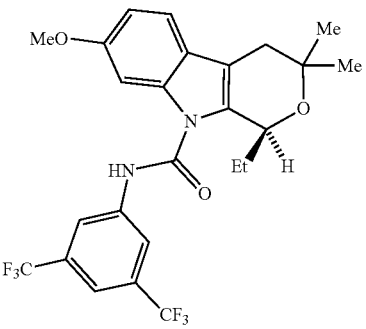

2f (S)—N-(3,5-bis(trifluoromethyl)phenyl)-6-methoxy-1-ethyl-3,3-dimethyl-3,4-dihydropyrano[3,4-b]indole-9(1H)-carboxamide (2f). Prepared according to General Procedure D, isolated as a white solid in 95:5 e.r. (19 mg, 93%). Analytical data for 2f: 1H NMR (500 MHz, CDCl$_3$) δ 8.06 (s, 2H), 7.71 (s, 1H), 7.58 (s, 1H), 7.38 (d, J=8.4 Hz, 1H), 7.25 (d, J=13.8 Hz, 1H), 6.92 (d, J=8.5 Hz, 1H), 5.11 (dd, J=6.0, 3.0 Hz, 1H), 3.87 (d, J=2.1 Hz, 3H), 2.73 (d, J=15.8 Hz, 1H), 2.59 (d, J=15.9 Hz, 1H), 1.98-1.88 (m, 1H), 1.77 (dp, J=14.4, 7.4 Hz, 1H), 1.46 (s, 3H), 1.32 (s, 3H), 0.85 (t, J=7.3 Hz, 3H). 13C NMR (126 MHz, CDCl3) δ 157.6, 149.5, 138.6, 136.5, 133.4, 132.9 (q, JC-F=33.8 Hz), 123.4, 122.9 (q, JC-F=272.8 Hz), 119.4, 119.2, 118.4-117.6 (m), 115.8, 110.1, 98.0, 71.1, 69.2, 56.0, 33.7, 30.3, 27.4, 23.0, 8.9. FTIR (ATR) cm−1 3277, 3096, 2973, 2934, 2875, 2841, 1717, 1684, 1653, 1617, 1576, 1559, 1540, 1507, 1491, 1473, 1437, 1383, 1348, 1308, 1275, 1227, 1170, 1128, 1107, 1041, 1016, 1000, 963, 936, 886, 799, 721, 701, 682, 668, 623. HRMS (ESI): Mass calculated for C25H25F6N2O3 [M+H]+: 515.176; found 515.177.

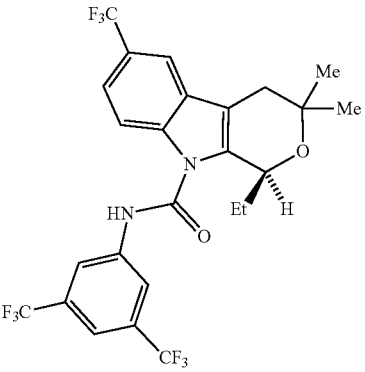

2g (S)—N-(3,5-bis(trifluoromethyl)phenyl)-5-trifluoromethyl-1-ethyl-3,3-dimethyl-3,4-dihydropyrano[3,4-b]indole-9(1H)-carboxamide (2g). Prepared according to General Procedure D, isolated as a white solid in 94:6 e.r. (14 mg, 70%). Analytical data for 2g: 1H NMR (500 MHz, CDCl$_3$) δ 8.08 (d, J=1.5 Hz, 2H), 7.79 (d, J=1.7 Hz, 1H), 7.74 (d, J=7.2 Hz, 1H), 7.74 (s, 1H), 7.61 (s, 1H), 7.57 (dd, J=8.8, 1.8 Hz, 1H), 5.16 (dq, J=5.4, 2.5 Hz, 1H), 2.79 (dd, J=15.8, 2.5 Hz, 1H), 2.66 (dd, J=15.7, 2.2 Hz, 1H), 1.95 (dqd, J=14.7, 7.4, 3.0 Hz, 1H), 1.84-1.71 (m, 1H), 1.48 (s, 3H), 1.31 (s, 3H), 0.86 (t, J=7.4 Hz, 3H). 13C NMR (126 MHz, CDCl3) δ 148.9, 138.2, 137.1, 136.9, 133.2, 132.9, 132.6, 129.0, 123.9, 121.7, 120.7, 119.3, 116.5, 115.9, 111.7, 71.2, 68.9, 33.5, 30.2, 27.2, 22.9, 9.0. FTIR (ATR) cm−1 2924, 2854, 1685, 1622, 1475, 1449, 1406, 1362, 1340, 1324, 1278, 1221, 1184, 1128, 1067, 1003, 889, 846, 824, 773, 743, 702, 683, 657. HRMS (ESI): Mass calculated for C25H21F9N2O2 [M−H]−: 551.1387; found 551.1388.

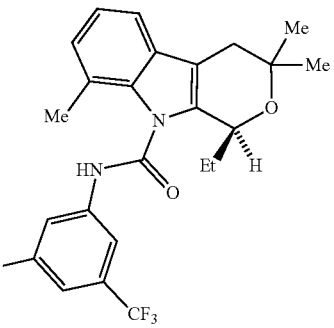

2h (S)—N-(3,5-bis(trifluoromethyl)phenyl)-7-methyl-1-ethyl-3,3-dimethyl-3,4-dihydropyrano[3,4-b]indole-9(1H)-carboxamide (2h). Prepared according to General Procedure D, isolated as a white solid in 80:20 e.r. (18 mg, 89%). Analytical data for 2h: 1H NMR (500 MHz, CDCl$_3$) δ 8.03 (s, 2H), 7.69 (s, 1H), 7.42 (s, 1H), 7.36 (d, J=7.7 Hz, 1H), 7.21 (t, J=7.5 Hz, 1H), 7.11 (d, J=7.3 Hz, 1H), 4.96 (dt, J=5.8, 2.6 Hz, 1H), 2.74 (dd, J=15.5, 2.5 Hz, 1H), 2.60 (dd, J=15.4, 2.0 Hz, 1H), 2.47 (s, 3H), 2.04 (dqd, J=14.8, 7.4, 3.0 Hz, 1H), 1.97-1.87 (m, 1H), 1.46 (s, 3H), 1.23 (s, 3H), 0.86 (t, J=7.3 Hz, 3H). 13C NMR (126 MHz, CDCl3) δ 150.2, 138.4, 135.5, 135.1, 132.9 (q, JC-F=33.8 Hz), 130.3, 126.7, 122.9, 122.8 (q, JC-F=272.1 Hz), 122.4, 118.7 (d, JC-F=4.2 Hz), 118.3, 116.6, 114.2, 71.2, 69.2, 33.6, 30.2, 29.7, 27.6, 23.1, 19.7, 8.7. FTIR (ATR) cm−1 3356, 2917, 2849, 1720, 1672, 1540, 1472, 1447, 1381, 1353, 1306, 1274, 1184, 1172, 1131, 1087, 1043, 888, 782, 732, 698, 681, 655. HRMS (ESI): Mass calculated for C25H24F6N2NaO2 [M+Na]+: 521.163; found 521.165.

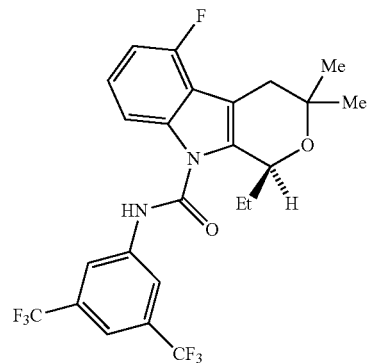

2i (S)—N-(3,5-bis(trifluoromethyl)phenyl)-1-ethyl-5-fluoro-3,3-dimethyl-3,4-dihydropyrano[3,4-b]indole-9(1H)-carboxamide (2i). Prepared according to General Procedure D, isolated as a white solid in 92:8 e.r. (15 mg, 73%). Analytical data for 2i: 1H NMR (500 MHz, CDCl$_3$) δ 8.06 (s, 2H), 7.69 (s, 2H), 7.38 (d, J=8.3 Hz, 1H), 7.20 (td, J=8.2, 5.3 Hz, 1H), 6.92 (dd, J=10.0, 8.0 Hz, 1H), 5.11 (dd, J=5.9, 2.8 Hz, 1H), 2.89 (dd, J=16.3, 2.6 Hz, 1H), 2.82 (dt, J=16.2, 1.7 Hz, 1H), 1.91 (dqd, J=14.7, 7.4, 3.0 Hz, 1H), 1.80-1.67 (m, 1H), 1.43 (s, 3H), 1.30 (s, 3H), 0.84 (t, J=7.3 Hz, 3H). 13C NMR (126 MHz, CDCl3) δ 157.9, 149.2, 138.4, 137.5, 135.1, 132.9 (d, JC-F=33.5 Hz), 124.4 (d, JC-F=7.7 Hz), 119.2, 118.3, 113.6, 108.6, 108.4, 107.4, 71.1, 68.9, 35.1, 30.2, 27.3, 22.9, 8.9. FTIR (ATR) cm−1 3452, 2976, 2936, 1742, 1673, 1552, 1473, 1442, 1412, 1380, 1369, 1336, 1307, 1275, 1242, 1167, 1110, 1056, 1001, 945, 892, 847, 773, 734, 702, 681, 634, 590. HRMS (ESI): Mass calculated for C24H21F7N2NaO2 [M+Na]+: 525.138; found 525.140.

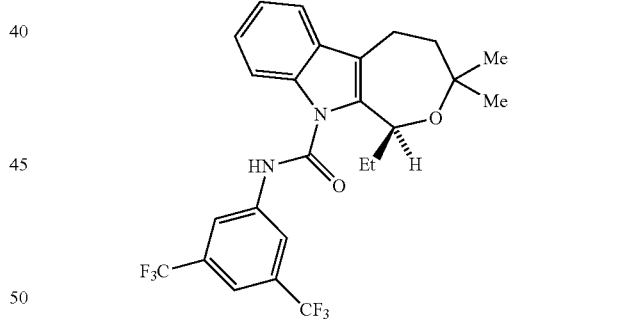

2j (S)—N-(3,5-bis(trifluoromethyl)phenyl)-1-ethyl-3,3-dimethyl-4,5-dihydro-1H-oxepino[3,4-b]indole-10(3H)-carboxamide (2j). Prepared according to General Procedure D, isolated as a white solid in 92:8 e.r. (15 mg, 73%). Analytical data for 2j: 1H NMR (500 MHz, CDCl$_3$) δ 8.05 (s, 2H), 7.70 (d, J=23.9 Hz, 2H), 7.56-7.44 (m, 2H), 7.25 (d, J=7.5 Hz, 1H), 5.13 (dt, J=8.5, 2.4 Hz, 1H), 2.95 (ddt, J=14.8, 12.1, 2.4 Hz, 1H), 2.67 (ddd, J=15.6, 5.7, 2.0 Hz, 1H), 1.99 (ddd, J=13.9, 5.7, 2.2 Hz, 1H), 1.92 (t, J=12.3 Hz, 1H), 1.90-1.83 (m, 1H), 1.68-1.56 (m, 1H), 1.37 (s, 3H), 1.34 (s, 3H), 0.96 (t, J=7.2 Hz, 3H). 13C NMR (126 MHz, CDCl3) δ 150.0, 139.3, 138.7, 135.2, 132.9 (d, JC-F=33.7 Hz), 129.9, 126.2, 124.0, 123.6, 123.0, 122.5, 121.8, 119.1, 118.1, 110.6, 74.7, 70.9, 41.9, 30.0, 29.5, 26.4, 18.6, 10.4. FTIR (ATR) cm−1 3261, 3178, 3093, 3061, 2972, 2932, 2877, 1725, 1670, 1626, 1564, 1474, 1456, 1443, 1381, 1352, 1311, 1274, 1217, 1172, 1133, 1109, 1060, 1027, 946, 891, 840, 786, 735, 720, 701, 682, 653, 635. HRMS (ESI): Mass calculated for C25H25F6N2O2 [M+H]+: 499.181; found 499.182.

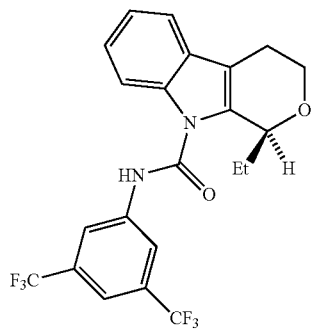

2k (S)—N-(3,5-bis(trifluoromethyl)phenyl)-1-ethyl-3,4-dihydropyrano[3,4-b]indole-9(1H)-carboxamide (2k). Prepared according to General Procedure D, isolated as a white solid in 92:8 e.r. (15 mg, 73%). Analytical data for 2k: 1H NMR (500 MHz, CDCl3) δ 8.04 (s, 2H), 7.87 (s, 1H), 7.67 (s, 1H), 7.62 (d, J=8.2 Hz, 1H), 7.52-7.47 (m, 1H), 7.32 (t, J=7.4 Hz, 1H), 7.27 (t, J=7.4 Hz, 1H), 5.11 (dd, J=8.8, 2.4 Hz, 1H), 4.08 (ddd, J=11.4, 6.6, 4.9 Hz, 1H), 3.88 (dt, J=11.1, 5.3 Hz, 1H), 2.76-2.67 (m, 1H), 2.66-2.56 (m, 1H), 1.96 (dtq, J=14.8, 7.4, 3.7 Hz, 1H), 1.84-1.69 (m, 1H), 0.99 (t, J=7.3 Hz, 3H). 13C NMR (126 MHz, CDCl3) δ 149.1, 138.7, 136.8, 134.6, 132.8 (q, J=33.6 Hz), 129.3, 124.1, 122.9 (q, JC-F=272.8 Hz), 122.9, 119.3, 119.2, 118.0 (p, JC-F=3.7 Hz), 114.6, 111.7, 73.7, 60.4, 26.6, 22.0, 10.0. FTIR (ATR) cm−1 3245, 2969, 2940, 2881, 1705, 1628, 1568, 1473, 1456, 1390, 1372, 1355, 1306, 1274, 1219, 1175, 1109, 1093, 1016, 961, 951, 880, 785, 740, 680, 662, 625, 609, 588. HRMS (ESI): Mass calculated for C22H18F6N2NaO2 [M+Na]+: 479.116; found 479.117.

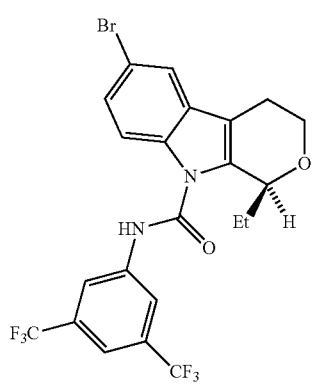

2l (S)—N-(3,5-bis(trifluoromethyl)phenyl)-6-bromo-1-ethyl-3,4-dihydropyrano[3,4-b]indole-9(1H)-carboxamide (2l). Prepared according to General Procedure D, isolated as a white solid in 92:8 e.r. (15 mg, 73%). Analytical data for 2l: 1H NMR (500 MHz, CDCl3) δ 8.02 (s, 2H), 7.69 (s, 1H), 7.63 (dd, J=7.8, 1.9 Hz, 1H), 7.60 (s, 1H), 7.51 (d, J=8.7 Hz, 1H), 7.40 (dd, J=8.7, 2.0 Hz, 1H), 5.12 (d, J=8.5 Hz, 1H), 4.10 (dt, J=11.1, 5.5 Hz, 1H), 3.89 (dt, J=12.7, 5.5 Hz, 1H), 2.78-2.65 (m, 2H), 1.92 (dqd, J=14.7, 7.3, 2.6 Hz, 1H), 1.82-1.71 (m, 1H), 0.99 (t, J=7.3 Hz, 3H). 13C NMR (126 MHz, CDCl3) δ 148.8, 138.4, 138.0, 133.5, 133.1, 131.0, 126.8, 122.1, 119.4, 116.2, 114.3, 113.1, 73.6, 60.6, 29.7, 26.7, 22.1, 9.9. FTIR (ATR) cm−1 3232, 2967, 2928, 2875, 1669, 1562, 1529, 1461, 1377, 1348, 1304, 1273, 1190, 1170, 1109, 1067, 988, 959, 897, 874, 794, 700, 681, 620, 585, 575. HRMS (ESI): Mass calculated for C22H17BrF6N2NaO2 [M+Na]+: 557.027; found 557.028.

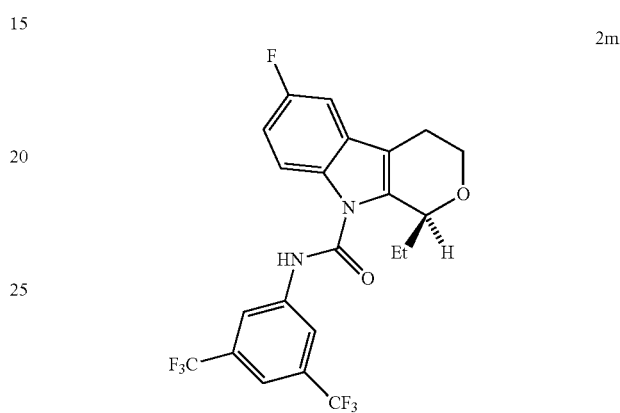

2m (S)—N-(3,5-bis(trifluoromethyl)phenyl)-1-ethyl-6-fluoro-3,4-dihydropyrano[3,4-b]indole-9(1H)-carboxamide (2m). Prepared according to General Procedure D, isolated as a white solid in 92:8 e.r. (15 mg, 73%). Analytical data for 2m: 1H NMR (500 MHz, CDCl$_3$) δ 8.02 (s, 2H), 7.68 (s, 1H), 7.67 (s, 1H), 7.57 (dd, J=8.9, 4.0 Hz, 1H), 7.15 (dd, J=8.5, 2.5 Hz, 1H), 7.04 (td, J=8.9, 2.6 Hz, 1H), 5.12 (d, J=8.6 Hz, 1H), 4.10 (dt, J=11.2, 5.5 Hz, 1H), 3.89 (dt, J=11.3, 5.4 Hz, 1H), 2.81-2.59 (m, 2H), 1.94 (dqd, J=15.0, 7.7, 2.7 Hz, 1H), 1.77 (dp, J=15.0, 7.5 Hz, 1H), 1.00 (t, J=7.3 Hz, 3H). 13C NMR (126 MHz, CDCl3) δ 160.2, 148.9, 138.5, 138.5, 133.0, 132.8, 131.1, 123.9, 121.8, 119.3, 114.7, 112.6, 111.8, 111.6, 105.1, 105.0, 73.7, 60.5, 29.7, 26.7, 22.1, 10.0. FTIR (ATR) cm−1 3244, 3183, 3062, 2967, 2936, 2878, 2848, 1706, 1627, 1565, 1464, 1443, 1409, 1386, 1355, 1307, 1271, 1216, 1169, 1125, 1093, 1067, 1022, 998, 952, 907, 881, 859, 826, 807, 798, 783, 740, 701, 680. C22H17F7N2NaO2 [M+Na]+: 497.107; found 497.107

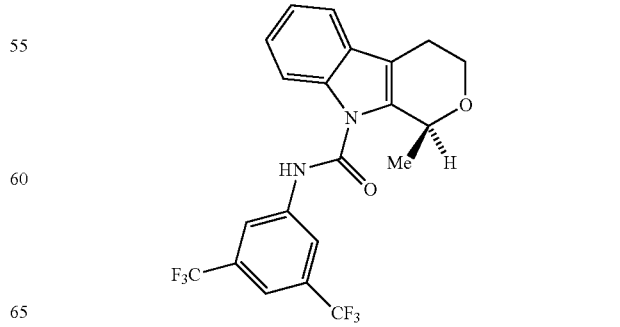

2n (S)—N-(3,5-bis(trifluoromethyl)phenyl)-1-methyl-3,4-dihydropyrano[3,4-b]indole-9(1H)-carboxamide (2n). Prepared according to General Procedure D, isolated as a white solid in 92:8 e.r. (15 mg, 73%). Analytical data for 2n: 1H NMR (500 MHz, CDCl3) δ 8.04 (s, 2H), 7.75 (s, 1H), 7.68 (s, 1H), 7.62 (d, J=8.1 Hz, 1H), 7.54-7.49 (m, 1H), 7.33 (t, J=8.0 Hz, 1H), 7.28 (t, J=7.4 Hz, 1H), 7.24 (s, 1H), 5.35 (dd, J=6.3, 6.3, 6.3 Hz, 1H), 4.13 (ddd, J=11.2, 6.2, 4.9 Hz, 1H), 3.97-3.87 (m, 1H), 2.82-2.74 (m, 1H), 2.74-2.68 (m, 1H), 1.54 (d, J=6.4 Hz, 3H). 13C NMR (126 MHz, CDCl3) δ 149.1, 138.6, 137.9, 134.5, 132.9 (q, JC-F=33.7 Hz), 129.4, 124.2, 124.0, 123.0, 121.8, 119.4, 119.3 (d, JC-F=4.2 Hz), 118.1, 114.3, 111.6, 68.9, 60.9, 22.2, 20.1. FTIR (ATR) cm−1 3295, 3122, 3084, 3066, 2978, 2922, 2875, 2851, 1702, 1674, 1650, 1629, 1572, 1536, 1475, 1451, 1412, 1391, 1371, 1349, 1307, 1283, 1274, 1248, 1216, 1175, 1124, 1113, 1103, 1088, 1049, 1023, 964, 949, 901, 887, 849, 841, 816, 784, 754, 746, 740, 725, 703, 683, 660, 646. C21H16F6N2NaO2 [M+Na]+: 465.101; found 465.102.

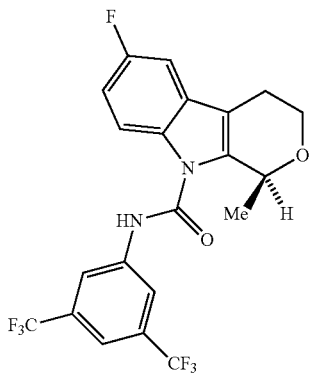

(S)—N-(3,5-bis(trifluoromethyl)phenyl)-6-fluoro-1-methyl-3,4-dihydropyrano[3,4-b]indole-9(1H)-carboxamide (2o). Prepared according to General Procedure D, isolated as a white solid in 92:8 e.r. (15 mg, 73%). Analytical data for 2o: 1H NMR (500 MHz, CDCl$_3$) δ 8.04 (s, 2H), 7.91 (s, 1H), 7.68 (s, 1H), 7.55 (dd, J=9.0, 4.0 Hz, 1H), 7.10 (ddd, J=24.1, 8.5, 2.6 Hz, 1H), 7.02 (td, J=8.9, 2.7 Hz, 1H), 5.28 (dd, J=6.4, 6.2, 6.2 Hz, 1H), 4.11 (dt, J=11.3, 5.9 Hz, 1H), 3.88 (dt, J=11.2, 5.3 Hz, 1H), 2.66 (dt, J=16.0, 5.1 Hz, 1H), 2.56-2.46 (m, 1H), 1.53 (t, J=6.4 Hz, 3H). 13C NMR (126 MHz, CDCl3) δ 160.2, 158.2, 148.9, 139.3, 138.6, 132.9 (q, JC-F=33.7 Hz), 131.0, 130.2 (d, JC-F=9.5 Hz), 122.9 (q, JC-F=273.0 Hz), 119.3 (d, JC-F=4.1 Hz), 118.5-117.9 (m), 113.9 (d, JC-F=3.9 Hz), 112.6 (d, JC-F=9.5 Hz), 111.8, 111.6, 105.1, 104.9, 68.8, 60.6, 21.9, 20.0. FTIR (ATR) cm−1 3243, 3100, 2977, 2928, 2887, 1704, 1626, 1569, 1463, 1443, 1386, 1357, 1347, 1309, 1299, 1270, 1246, 1218, 1177, 1109, 1082, 1017, 979, 947, 913, 903, 878, 861, 804, 702, 680, 606, 580. C21H15F7N2NaO2 [M+Na]+: 483.091; found 483.092.

Coixspirolactam C, Precursors, Miscellaneous Structures

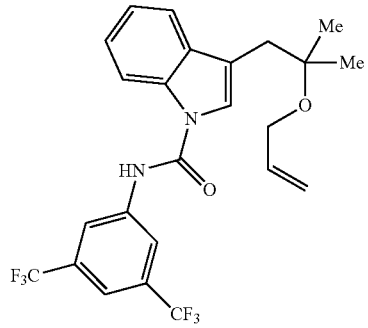

3-(2-(allyloxy)-2-methylpropyl)-N-(3,5-bis(trifluoromethyl)phenyl)-1H-indole-1-carboxamide (3). Prepared according to the above procedure for the synthesis of 5, isolated as a cream solid (71%). Analytical data for 3: 1H NMR (500 MHz, CDCl3) δ 8.20 (d, J=8.2 Hz, 1H), 8.06 (s, 2H), 7.66 (s, 1H), 7.61 (d, J=7.8 Hz, 1H), 7.52 (s, 1H), 7.44 (s, 1H), 7.38 (t, J=7.7 Hz, 1H), 7.30 (t, J=7.5 Hz, 1H), 6.03 (ddt, J=17.6, 10.4, 5.1 Hz, 1H), 5.36 (dd, J=17.2, 2.1 Hz, 1H), 5.20 (dd, J=10.4, 1.8 Hz, 1H), 4.04 (dd, J=5.2, 1.5 Hz, 2H), 2.94 (s, 2H), 1.29 (s, 6H). 13C NMR (126 MHz, CDCl$_3$) δ 148.9, 139.0, 136.4, 135.3, 132.6 (q, JC-F=33.6 Hz), 131.4, 124.9, 123.0 (q, JC-F=272.6 Hz), 122.9, 121.7, 119.8, 119.6, 118.8, 117.7, 115.4, 114.6, 75.4, 62.9, 35.3, 25.6. FTIR (ATR) cm−1 3323, 3116, 3074, 2980, 2930, 2867, 2852, 1714, 1653, 1590, 1559, 1477, 1455, 1443, 1390, 1369, 1351, 1337, 1306, 1276, 1254, 1221, 1195, 1166, 1125, 1072, 1017, 944, 931, 899, 885, 866, 837, 780, 762, 744, 730, 703, 682, 668, 639, 623. HRMS (ESI): Mass calculated for C24H21F6N2O2 [M−H]−: 483.151; found 483.150.

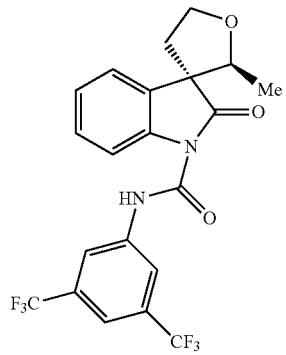

(2S,3S)—N-(3,5-bis(trifluoromethyl)phenyl)-2-methyl-2'-oxo-4,5-dihydro-2H-spiro[furan-3,3'-indoline]-1'-carboxamide (4). Prepared according to Procedure for Spirocyclization (75%). Analytical data for 4: 1H NMR (500 MHz, CDCl3) δ 11.13 (s, 1H), 8.34 (d, J=8.2 Hz, 1H), 8.11 (d, J=1.4 Hz, 2H), 7.65 (s, 1H), 7.40 (ddd, J=8.5, 7.1, 1.9 Hz, 1H), 7.31 (dd, J=7.6, 1.9 Hz, 1H), 7.28 (td, J=7.6, 1.1 Hz, 1H), 4.32 (td, J=8.6, 6.0 Hz, 1H), 4.25 (q, J=6.3 Hz, 1H), 4.21 (td, J=9.3, 6.2 Hz, 1H), 2.78 (ddd, J=12.8, 9.4, 6.0 Hz, 1H), 2.33 (ddd, J=12.8, 8.4, 6.1 Hz, 1H), 0.93 (d, J=6.2 Hz, 3H). 13C NMR (126 MHz, CDCl3) δ 181.1, 149.0, 138.7 (d, JC-F=7.1 Hz), 132.5 (q, JC-F=33.6 Hz), 129.7, 128.7, 125.5, 124.0, 123.0 (q, JC-F=273.4 Hz), 120.0 (q, JC-F=4.1 Hz), 117.7 (p, JC-F=4.0 Hz), 116.4, 83.4, 67.3, 58.9, 39.6, 15.1. FTIR (ATR) cm−1 3192, 3093, 2984, 2895, 1733, 1627, 1576, 1467, 1449, 1388, 1356, 1348, 1310, 1270, 1191, 1165, 1127, 1099, 1053, 1015, 1000, 957, 935, 910, 882, 869, 844, 762, 732, 717, 698, 680. HRMS (ESI): Mass calculated for C21H16F6N2NaO3 [M+Na]+: 481.0957; found 481.0964.

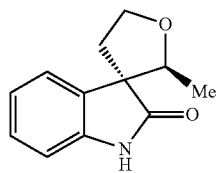

5

(2S,3S)-2-methyl-4,5-dihydro-2H-spiro[furan-3,3'-indolin]-2'-one (5). Prepared according to Procedure for Spirocyclization (60% from 4). Analytical data for 5: 1H NMR (500 MHz, CDCl3) δ 8.53 (s, 1H), 7.24 (t, J=7.1 Hz, 0H), 7.23 (d, J=7.5 Hz, 2H), 7.07 (td, J=7.5, 1.1 Hz, 1H), 6.97-6.91 (m, 1H), 4.26 (td, J=8.4, 6.5 Hz, 1H), 4.22-4.14 (m, 2H), 2.71 (ddd, J=12.8, 9.5, 6.5 Hz, 1H), 2.21 (ddd, J=12.7, 8.3, 5.6 Hz, 1H), 0.92 (d, J=6.2 Hz, 3H). 13C NMR (126 MHz, CDCl3) δ 179.7, 140.0, 131.6, 127.9, 124.6, 122.6, 109.8, 82.2, 67.1, 58.2, 38.1, 15.0. FTIR (ATR) cm−1 3224, 2972, 2949, 2929, 2879, 2849, 1713, 1673, 1620, 1600, 1468, 1447, 1385, 1337, 1319, 1279, 1265, 1225, 1186, 1145, 1119, 1104, 1050, 1015, 984, 954, 867, 828, 758, 717, 696, 677, 624. HRMS (ESI): Mass calculated for C12H13NNaO2 [M+Na]+: 226.0838; found 226.0838.

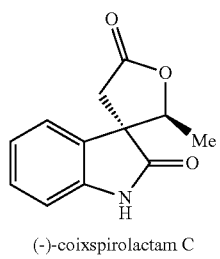

6

(−)-coixspirolactam C (2S,3S)-2-methyl-2H-spiro[furan-3,3'-indoline]-2',5(4H)-dione ((−)-coixspirolactam C, 6). Prepared according to Procedure for Oxidation (46%). Analytical data for 6: 1H NMR (500 MHz, CDCl3) δ 7.78 (s, 1H), 7.32 (td, J=7.7, 1.3 Hz, 1H), 7.23 (dd, J=7.5, 1.2 Hz, 1H), 7.12 (td, J=7.6, 1.0 Hz, 1H), 6.96 (dt, J=7.8, 0.8 Hz, 1H), 4.88 (q, J=6.4 Hz, 1H), 3.33 (d, J=17.1 Hz, 1H), 2.70 (d, J=17.1 Hz, 1H), 1.11 (dd, J=6.6, 2.6 Hz, 3H). 13C NMR (126 MHz, CDCl3) δ 176.0, 173.8, 139.6, 129.4, 128.1, 124.2, 123.3, 110.4, 81.5, 55.7, 40.2, 15.4. FTIR (ATR) cm−1 3260, 2979, 2932, 2876, 1791, 1768, 1715, 1621, 1600, 1472, 1388, 1343, 1279, 1227, 1185, 1084, 987, 943, 755, 676, 625. HRMS (ESI): Mass calculated for C12H11NNaO3 [M+Na]+: 240.0631; found 240.0632. Natural (+)-coixspirolactam C [α]D25=+5.9 (c=0.39, MeOH), iv synthetic (−)-coixspirolactam C [α]D25=−20.1 (c=0.074, MeOH).

REFERENCES

[1] S. Kobayashi, H. Ishitani, Chem. Rev. 1999, 99, 1069-1094.
[2] R. R. Knowles, E. N. Jacobsen, Proc. Natl. Acad. Sci. U.S.A. 2010, 107, 20678-20685.
[3] (a) K. Brak, E. N. Jacobsen, Angew. Chem. Int. Ed. 2013, 52, 534-561; (b) A. Milo, A. J. Neel, F. D. Toste, M. S. Sigman, Science 2015, 347, 737-743.
[4] S. E. Reisman, A. G. Doyle, E. N. Jacobsen, J. Am. Chem. Soc. 2008, 130, 7198-7199.
[5] (a) N. Z. Burns, M. R. Witten, E. N. Jacobsen, J. Am. Chem. Soc. 2011, 133, 14578-14581; (b) C. S. Yeung, R. E. Ziegler, J. A. Porco, Jr., E. N. Jacobsen, J. Am. Chem. Soc. 2014, 136, 13614-13617; (c) C. R. Kennedy, D. Lehnherr, N. S. Rajapaksa, D. D. Ford, Y. Park, E. N. Jacobsen, J. Am. Chem. Soc. 2016, 138, 13525-13528; (d) M. D. Visco, J. Attard, Y. Guan, A. E. Mattson, Tetrahedron Lett. 2017, 58, 2623-2628.
[6] (a) Q. W. Zhang, C. A. Fan, H. J. Zhang, Y. Q. Tu, Y. M. Zhao, P. Gu, Z. M. Chen, Angew Chem Int Ed Engl 2009, 48, 8572-8574; (b) I. Coric, S. Vellalath, B. List, J. Am. Chem. Soc. 2010, 132, 8536-8537; (c) P. N. Moquist, T. Kodama, S. E. Schaus, Angew. Chem. Int. Ed. 2010, 49, 7096-7100; (d) Z. Sun, G. A. Winschel, A. Borovika, P. Nagomy, J. Am. Chem. Soc. 2012, 134, 8074-8077; (e) C. Lu, X. Su, P. E. Floreancig, J. Org. Chem. 2013, 78, 9366-9376; (f) C. C. Hsiao, H. H. Liao, E. Sugiono, I. Atodiresei, M. Rueping, Chemistry 2013, 19, 9775-9779; (g) J. H. Kim, I. Coric, C. Palumbo, B. List, J. Am. Chem. Soc. 2015, 137, 1778-1781; (h) C. D. Gheewala, J. S. Hirschi, W. H. Lee, D. W. Paley, M. J. Vetticatt, T. H. Lambert, J. Am. Chem. Soc. 2018, 140, 3523-3527.
[7] S. Lee, P. S. Kaib, B. List, J. Am. Chem. Soc. 2017, 139, 2156-2159.
[8] (a) M. Rueping, C. M. Volla, I. Atodiresei, Org. Lett. 2012, 14, 4642-4645; (b) P. Maity, H. D. Srinivas, M. P. Watson, J. Am. Chem. Soc. 2011, 133, 17142-17145; (c) H. Zhang, L. Zhu, S. Wang, Z. J. Yao, J. Org. Chem. 2014, 79, 7063-7074; (d) M. Terada, F. Li, Y. Toda, Angew. Chem. Int. Ed. 2014, 53, 235-239; (e) W. Zi, F. D. Toste, J. Am. Chem. Soc. 2013, 135, 12600-12603.
[9] (a) M. H. Wang, D. T. Cohen, C. B. Schwamb, R. K. Mishra, K. A. Scheidt, J. Am. Chem. Soc. 2015, 137, 5891-5894; (b) K. J. R. Murauski, D. M. Walden, P. H.-Y. Cheong, K. A. Scheidt, Adv. Synth. Catal. 2017, 359, 3713-3719.
[10] S. Bhadra, H. Yamamoto, Chem. Rev. 2018, 118, 3391-3446.
[11] E. L. Larghi, T. S. Kaufman, Eur. J. Org. Chem. 2011, 2011, 5195-5231.
[12] (a) C. Zhao, S. B. Chen, D. Seidel, J. Am. Chem. Soc. 2016, 138, 9053-9056; (b) S. Das, L. Liu, Y. Zheng, M. W. Alachraf, W. Thiel, C. K. De, B. List, J. Am. Chem. Soc. 2016, 138, 9429-9432.
[13] (a) V. M. Lombardo, C. D. Thomas, K. A. Scheidt, Angew. Chem. Int. Ed. 2013, 52, 12910-12914; (b) E. Ascic, R. G. Ohm, R. Petersen, M. R. Hansen, C. L. Hansen, D. Madsen, D. Tanner, T. E. Nielsen, Chemistry 2014, 20, 3297-3300.
[14] (a) D. Parmar, E. Sugiono, S. Raja, M. Rueping, Chem. Rev. 2014, 114, 9047-9153; (b) H. Xu, S. J. Zuend, M. G. Woll, Y. Tao, E. N. Jacobsen, Science 2010, 327, 986-990.
[15] N. M. Nasir, K. Ermanis, P. A. Clarke, Org. Biomol. Chem. 2014, 12, 3323-3335.
[16] (a) M. Y. Lee, H. Y. Lin, F. Cheng, W. Chiang, Y. H. Kuo, Food Chem. Toxicol. 2008, 46, 1933-1939; (b) C. P.

Chung, C. Y. Hsu, J. H. Lin, Y. H. Kuo, W. Chiang, Y. L. Lin, J. Agric. Food Chem. 2011, 59, 1185-1194.
[17] Z. Zhang, P. R. Schreiner, Chem. Soc. Rev. 2009, 38, 1187-1198.
[18] for select examples of hydrogen-bond donor catalysis see: (a) A. Borovika, P.-I. Tang, S. Klapman, P. Nagomy, Angew. Chem. Int. Ed. 2013, 52, 13424-13428; (b) W. H. Pace, D.-L. Mo, T. W. Reidl, D. J. Wink, L. L. Anderson, Angew. Chem. Int. Ed. 2016, 55, 9183-9186; (c) C. Palo-Nieto, A. Sau, R. Williams, M. C. Galan, J. Org. Chem. 2017, 82, 407-414; for an example of an HBD-mediated tandem asymmetric Michael addition/oxa-Pictet Spengler process see: (d) W.-T. Fan, N.-K. Li, L. Xu, C. Qiao, X.-W. Wang, Org. Lett. 2017, 19, 6626-6629.
[19] P. R. Schreiner, A. Wittkopp, Org. Lett. 2002, 4, 217-220.
[20] J. Seayad, A. M. Seayad, B. List, J. Am. Chem. Soc. 2006, 128, 1086-1087.
[21] R. M. Beesley, C. K. Ingold, J. F. Thorpe, J. Chem. Soc., Trans. 1915, 107, 1080-1106.
[22] J. Shavel, H. Zinnes, J. Am. Chem. Soc. 1962, 84, 1320-1321.
[23] Z.-H. Gao, L.-M. Kong, X.-S. Zou, Y.-M. Shi, S.-Z. Shang, H.-R. Luo, C.-Q. Liang, X.-N. Li, Y. Li, X. Du, W.-L. Xiao, H.-D. Sun, Nat. Prod. Bioprospect. 2012, 2, 249-254.
[24] C. V. Galliford, K. A. Scheidt, Angew. Chem. Int. Ed. 2007, 46, 8748-8758.
[25] H. M. Davies, J. Du Bois, J. Q. Yu, Chem. Soc. Rev. 2011, 40, 1855-1856.
[26] Y. Zhao, J. Q. L. Ang, A. W. T. Ng, Y. Y. Yeung, RSC Adv. 2013, 3, 19765-19768.
[27] Attempts to obtain pure natural material to assess purity and the absolute value of the reported +5.9° optical rotation were not successful. The original isolation paper only provides numerical values for different NMR spectra and not full spectra to ascertain potential purity issues. Our synthetic material is >95% pure as determine by NMR and HPLC techniques.
[28] (a) C. Zheng, Z.-L. Xia, S.-L. You, Chem 2018, 4, 1952-1966; (b) P. D. Bailey, J. Chem. Research-S 1987, 202-203.

We claim:

1. A compound of the following formula or a salt, or a hydrate thereof:

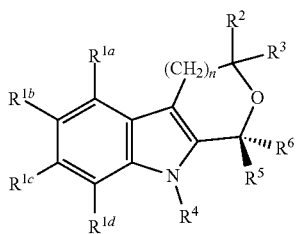

wherein:
$R^{1a}$, $R^{1b}$, $R^{1c}$, and $R^{1d}$ are independently selected from hydrogen, alkyl, halo, haloalkyl, and alkoxy, wherein optionally at least one of $R^{1a}$, $R^{1b}$, $R^{1c}$, and $R^{1d}$ is not hydrogen;
$R^2$ and $R^3$ are independently selected from hydrogen or alkyl, optionally wherein at least one of $R^2$ and $R^3$ is not hydrogen;

$R^4$ is selected from carboxy, carboxyalkyl, carboxamido, and carboxamidoaryl, which aryl substituent optionally is substituted with haloalkyl;
$R^5$ and $R^6$ are independently selected from hydrogen and alkyl, wherein optionally at least one of $R^5$ and $R^6$ is not hydrogen; and
n is an integer selected from 1 and 2.

2. The compound of claim 1, wherein at least one of $R^{1a}$, $R^{1b}$, $R^{1c}$, and $R^{1d}$ is fluoro.

3. The compound of claim 1, wherein at least one of $R^{1a}$, $R^{1b}$, $R^{1c}$, and $R^{1d}$ is bromo.

4. The compound of claim 1, wherein at least one of $R^{1a}$, $R^{1b}$, $R^{1c}$, and $R^{1d}$ is a branched or unbranched $C_{1-6}$-alkyl.

5. The compound of claim 4, wherein at least one of $R^{1a}$, $R^{1b}$, $R^{1c}$, and $R^{1d}$ is methyl.

6. The compound of claim 1, wherein at least one of $R^{1a}$, $R^{1b}$, $R^{1c}$, and $R^{1d}$ is a branched or unbranched $C_{1-6}$-alkoxy.

7. The compound of claim 6, wherein at least one of $R^{1a}$, $R^{1b}$, $R^{1c}$, and $R^{1d}$ is methoxy.

8. The compound of claim 1, wherein at least one of $R^{1a}$, $R^{1b}$, $R^{1c}$, and $R^{1d}$ is haloalkyl.

9. The compound of claim 8, wherein at least one of $R^{1a}$, $R^{1b}$, $R^{1c}$, and $R^{1d}$ is —$CF_3$.

10. The compound of claim 1, wherein at least one of $R^2$ and $R^3$ is branched or unbranched $C_{1-6}$-alkyl.

11. The compound of claim 1, wherein each of $R^2$ and $R^3$ are branched or unbranched $C_{1-6}$-alkyl.

12. The compound of claim 1, wherein each of $R^2$ and $R^3$ is methyl.

13. The compound of claim 1, wherein at least one of $R^5$ and $R^6$ is hydrogen.

14. The compound of claim 1, wherein at least one of $R^5$ and $R^6$ is a branched or unbranched $C_{1-6}$-alkyl.

15. The compound of claim 14, wherein at least one of $R^5$ and $R^6$ is ethyl.

16. The compound of claim 14, wherein at least one of $R^5$ and $R^6$ is methyl.

17. The compound of claim 1, wherein $R^4$ is —C(O)$NR^7(R^8)$, wherein $R^7$ is hydrogen and $R^8$ is aryl optionally substituted at one or more positions with trifluoromethyl.

18. The compound of claim 17, wherein $R^8$ is 3,5-bis(trifluoromethyl)phenyl.

19. The compound of claim 1, wherein the compound is selected from the group consisting of:

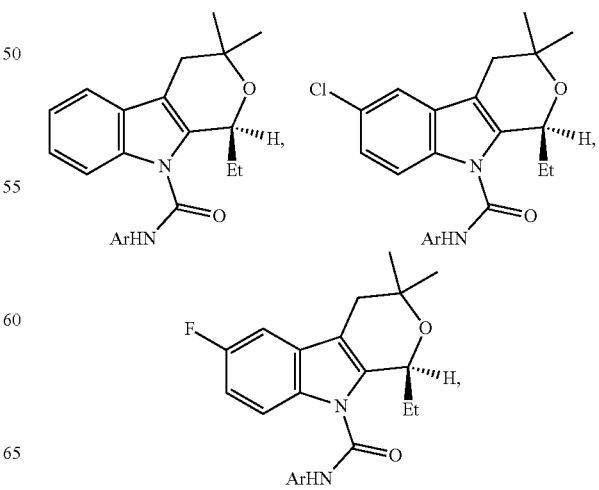

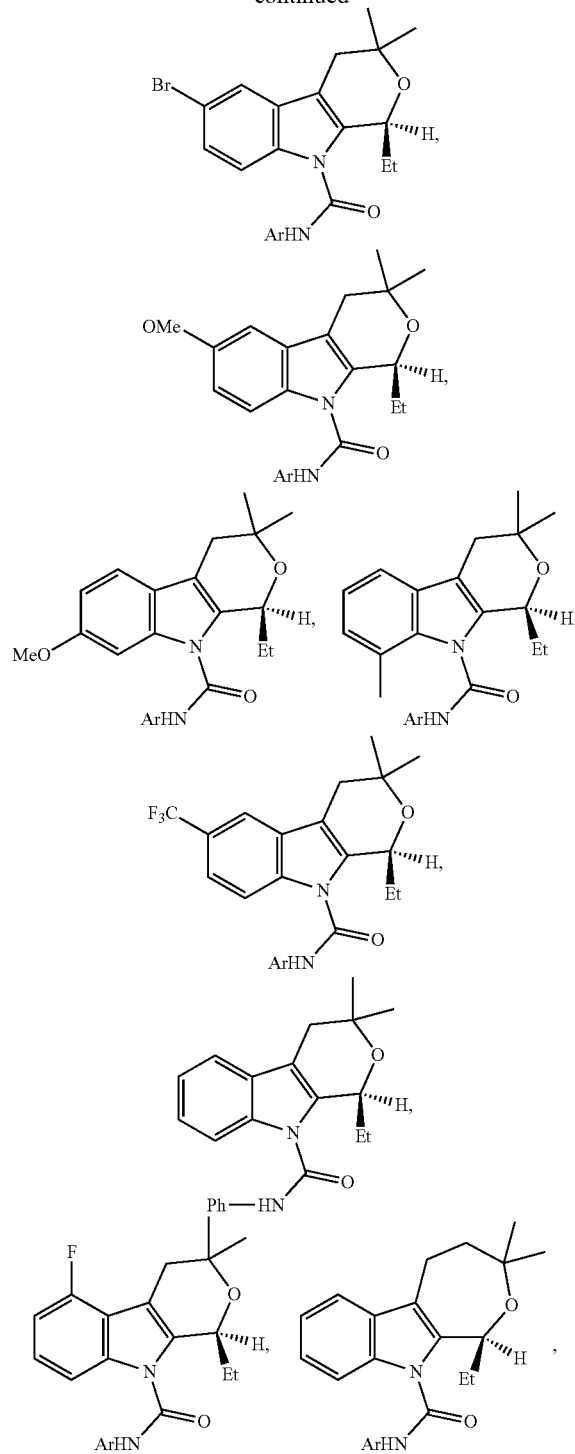

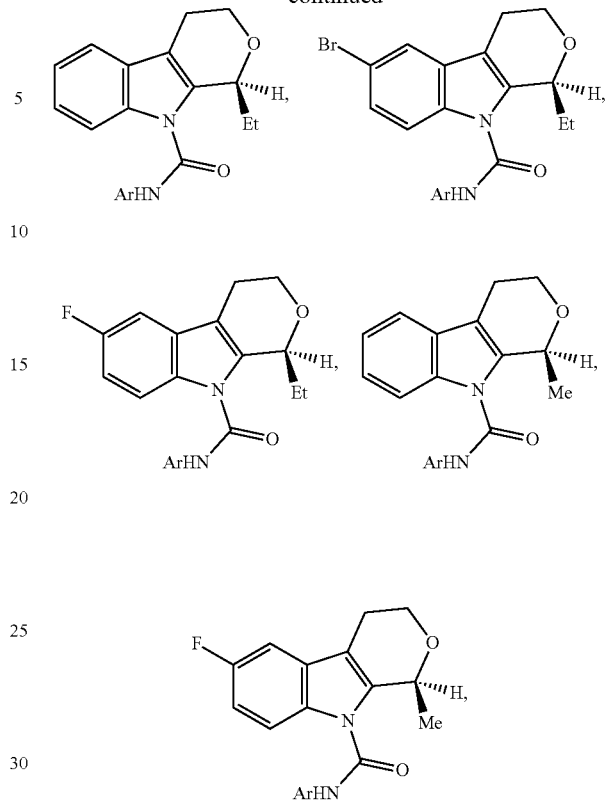

and wherein Ar is 3,5-bis(trifluoromethyl)phenyl.

20. An enantiomerically pure composition comprising or consisting of the compound of claim 1.

21. A racemic mixture of compounds comprising the compound of claim 1, wherein the compound of claim 1 represents at least about 80%, 85%, 90%, 95%, 96%, 97%, 98%, or 99% of the racemic mixture of compounds.

22. A pharmaceutical composition comprising: (a) an effective amount of the compound of claim 1; and (b) at least one of a carrier, excipient, or diluent.

23. The compound of claim 1, wherein n is 1.

24. The compound of claim 1, wherein $R^{1a}$, $R^{1b}$, $R^{1c}$, and $R^{1d}$ are hydrogen.

25. The compound of claim 1, wherein $R^2$ and $R^3$ are hydrogen.

26. The compound of claim 1, wherein $R^4$ is carboxamidoaryl.

27. The compound of claim 1, wherein $R^5$ is ethyl and $R^6$ is hydrogen.

* * * * *